(12) United States Patent
Scholl et al.

(10) Patent No.: US 10,088,481 B2
(45) Date of Patent: *Oct. 2, 2018

(54) METHODS FOR LIQUID DIRECT FLUORESCENT ANTIBODY INTRACELLULAR VIRUS DETECTION

(71) Applicant: Diagnostic Hybrids, Inc., Athens, OH (US)

(72) Inventors: David R. Scholl, Athens, OH (US); James L. Brown, Athens, OH (US); Joseph A. Jollick, Jr., Athens, OH (US); Ronald Lollar, Athens, OH (US)

(73) Assignee: Diagnostic Hybrids, Inc., Athens, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/601,647

(22) Filed: Jan. 21, 2015

(65) Prior Publication Data

US 2015/0192584 A1    Jul. 9, 2015

Related U.S. Application Data

(63) Continuation of application No. 13/166,228, filed on Jun. 22, 2011, now Pat. No. 8,975,016, which is a continuation of application No. 12/425,256, filed on Apr. 16, 2009, now Pat. No. 8,003,314.

(51) Int. Cl.

| | |
|---|---|
| *A61K 39/00* | (2006.01) |
| *A61K 39/395* | (2006.01) |
| *C07K 14/705* | (2006.01) |
| *C07K 16/18* | (2006.01) |
| *C07K 16/28* | (2006.01) |
| *G01N 33/569* | (2006.01) |
| *G01N 33/50* | (2006.01) |
| *G01N 33/543* | (2006.01) |

(52) U.S. Cl.
CPC ... *G01N 33/56983* (2013.01); *G01N 33/5091* (2013.01); *G01N 33/54326* (2013.01); *G01N 2333/075* (2013.01); *G01N 2333/11* (2013.01); *G01N 2333/115* (2013.01); *G01N 2333/135* (2013.01)

(58) Field of Classification Search
CPC .......... A61K 2300/00; A61K 2039/505; A61K 39/12; A61K 45/06; C07K 2317/76
See application file for complete search history.

(56) References Cited

U.S. PATENT DOCUMENTS

| | | | |
|---|---|---|---|
| 3,817,837 A | 6/1974 | Rubenstein | 435/7.9 |
| 3,850,752 A | 11/1974 | Schuurs et al. | 435/7.93 |
| 3,939,350 A | 2/1976 | Kronick et al. | 250/365 |
| 3,992,516 A | 11/1976 | Lim | 435/7.22 |
| 3,996,345 A | 12/1976 | Ullman et al. | 436/537 |
| 4,275,149 A | 6/1981 | Litman | 435/7.91 |
| 4,277,437 A | 7/1981 | Maggio | 422/401 |
| 4,366,241 A | 12/1982 | Tom et al. | 435/7.91 |
| 4,693,972 A | 9/1987 | Mansour et al. | 435/34 |
| 5,186,827 A | 2/1993 | Liberti et al. | 210/222 |
| 5,281,517 A | 1/1994 | Bacus et al. | 435/6.12 |
| 5,466,574 A | 11/1995 | Liberti et al. | 435/5 |
| 5,576,482 A | 11/1996 | Russ et al. | 73/61.43 |
| 5,579,531 A | 11/1996 | Sugita | 710/51 |
| 5,602,234 A | 2/1997 | Sawayanagi | 530/390.5 |
| 5,637,473 A | 6/1997 | Clemmons | 435/7.91 |
| 5,641,072 A | 6/1997 | Otake | 209/524 |
| 5,658,745 A | 8/1997 | Greene et al. | 435/7.24 |
| 5,698,271 A | 12/1997 | Liberti et al. | 427/550 |
| 5,977,081 A | 11/1999 | Marciani | 514/25 |
| 5,985,153 A | 11/1999 | Dolan | 210/695 |
| 5,993,665 A | 11/1999 | Terstappen | 210/695 |
| 6,080,725 A | 6/2000 | Marciani | 514/26 |
| 6,136,182 A | 10/2000 | Dolan | 210/94 |
| 6,136,540 A | 10/2000 | Tsipouras et al. | 435/6.16 |
| 6,221,607 B1 | 4/2001 | Tsipouras et al. | 435/6.16 |
| 6,225,046 B1 * | 5/2001 | Vesey | G01N 33/56911 435/239 |
| 6,262,029 B1 | 7/2001 | Press et al. | 514/26 |

(Continued)

FOREIGN PATENT DOCUMENTS

| | | |
|---|---|---|
| CN | 1372142 | 10/2002 |
| WO | WO/1993/003173 | 2/1993 |

(Continued)

OTHER PUBLICATIONS

Diagnostic Hybrids, D3 Ultra DFA Respiratory Virus Screening & ID Kit, 2006:1-10.*
Diagnostic Hybrids, Diagnostic Hybrids announces release of D3 Duet DFA Kits for simultaneous screening of multiple respiratory viruses in cell culture, 2007: pdf pp. 1-2.*
Baumgarth et al., "Innate and Acquired Humoral Immunities to Influenza Virus are Mediated by Distinct Arms of the Immune System." *PNAS* 96:2250-2255 (1999).
Espy et al., "Rapid detection of influenza virus by shell vial assay with monoclonal antibodies ." *J. Clin. Microbiol* 24:677-679 (1986).
Frank et al., "Comparison of different tissue cultures for isolation and quantitation of influenza and parainfluenxza viruses." *J. Clin. Microbiol* 10:32-36 (1979).

(Continued)

*Primary Examiner* — Barry A Chestnut
(74) *Attorney, Agent, or Firm* — Medlen & Carroll, LLP

(57) ABSTRACT

The present invention describes a liquid direct fluorescence antibody assay that is rapid and sensitive to detect respiratory virus in infected cells. The assay includes centrifugation of the specimen, incubation of sample and reagents in solution, and detection of the absence or presence of respiratory virus. Sapogenin is used as a detergent to permeabilize the cells for entry of the monoclonal antibodies to react with intracellular antigens. The cells are stained with fluorescently labeled monoclonal antibodies against the viral antigens along with a background stain and a fluorescent nuclear stain. This counter staining decreases background and allows co-localization of antigen and nuclear structures for enhanced detection.

14 Claims, 15 Drawing Sheets

(56) References Cited

U.S. PATENT DOCUMENTS

| | | | |
|---|---|---|---|
| 6,320,174 B1 | 11/2001 | Tafas et al. | 250/208.1 |
| 6,355,816 B1 | 3/2002 | Dobbins | 554/14 |
| 6,703,247 B1 | 3/2004 | Chu | 436/180 |
| 6,759,235 B2 | 7/2004 | Empedocle et al. | 435/288.7 |
| 6,890,426 B2 | 5/2005 | Terstappen | 210/94 |
| 6,890,741 B2 | 5/2005 | Fan et al. | 435/91.2 |
| 6,929,953 B1 | 8/2005 | Wardlaw | 436/63 |
| 7,011,794 B2 | 3/2006 | Kagan et al. | 356/246 |
| 7,150,965 B2 * | 12/2006 | Huang | G01N 33/56983 435/325 |
| 7,248,360 B2 | 7/2007 | Horchner et al. | 356/318 |
| 7,329,537 B2 | 2/2008 | Qiu | 435/288.3 |
| 7,341,837 B2 | 3/2008 | Lawton | 435/7.1 |
| 7,399,607 B2 | 7/2008 | Williams et al. | 435/23 |
| 7,408,640 B2 | 8/2008 | Cullum et al. | 356/368 |
| 7,410,769 B2 | 8/2008 | Burroughs-Tencza et al. | 435/7.1 |
| 7,424,165 B2 | 9/2008 | Recht | 382/255 |
| 7,527,924 B2 | 5/2009 | Fleming et al. | 435/2 |
| 7,764,821 B2 | 7/2010 | Coumans et al. | 382/133 |
| 7,943,397 B2 | 5/2011 | Tibbe et al. | 436/526 |
| 8,003,314 B2 * | 8/2011 | Scholl | G01N 33/5091 435/5 |
| 8,975,016 B2 | 3/2015 | Scholl et al. | 435/5 |
| 2004/0023222 A1 | 2/2004 | Russell et al. | 436/100 |
| 2005/0048500 A1 | 3/2005 | Lawton | 435/6.16 |
| 2005/0095601 A1 | 5/2005 | Cullum et al. | 435/6.11 |
| 2006/0024756 A1 * | 2/2006 | Tibbe | G01N 15/1463 435/7.2 |
| 2006/0216696 A1 | 9/2006 | Goguen | 435/5 |
| 2006/0256338 A1 | 11/2006 | Gratton et al. | 356/417 |
| 2007/0042001 A1 | 2/2007 | Weeks-Levy et al. | 424/209.1 |
| 2007/0042002 A1 | 2/2007 | Weeks-Levy et al. | 424/209.1 |
| 2007/0065893 A1 | 3/2007 | Carte et al. | 435/18 |
| 2007/0117158 A1 | 5/2007 | Coumans et al. | 435/7.2 |
| 2007/0172911 A1 | 7/2007 | Farrell et al. | 435/40.5 |
| 2007/0248962 A1 | 10/2007 | Gerna et al. | 435/6.16 |
| 2007/0279626 A9 | 12/2007 | Sun et al. | 356/301 |
| 2008/0008725 A1 | 1/2008 | Weeks-Levy et al. | 424/209.1 |
| 2008/0161324 A1 * | 7/2008 | Johansen | A61K 31/135 514/255.03 |

FOREIGN PATENT DOCUMENTS

| | | |
|---|---|---|
| WO | WO1998/08094 | 2/1998 |
| WO | WO 2000/45169 | 8/2000 |
| WO | WO 2002/065103 | 8/2002 |
| WO | WO2003/019141 | 3/2003 |
| WO | WO2004/076664 | 9/2004 |
| WO | WO 2003/073817 | 12/2004 |

OTHER PUBLICATIONS

Köehler and Milstein "Continuous cultures of fused cells secreting antibody of predefined specicicity," *Nature* 256:495 (1975).

Lonsdale et al., "A rapid method for immunotitration of influenza viruses using flow cytometry." *J. Virol Methods* 110(1):67-71 (2003).

Meguro et al., "canine kidney cell line for isolation of respiratory viruses," *J. Clin. Microbiol* 9:175-179 (1979).

Mills et al., "Detection of Influenza Virus by Centrifugal Inoculation of MDCK Cells and Staining with Monoclonal Antibodies." *J. Clin. Microbiol.* 27(11):2505-2508 (1989).

Schulze-Horsel et al., "Flow Cytometric Monitoring of Influenza A Virus Infection in MDCK Cells During Vaccine Production." *BMC Biotechnol.* 8:45 (2008).

Selleck et al., "Rapid Diagnosis of Highly Pathogenic Avian Influenza Using Pancreatic Impression Smears." *Avian Diseases* 47(s3):1190-1195 (2002).

Shiratsuchi et al., "Phosphatidylserine-Mediated Phagocytosis of Influenza A Virus-Infected Cells by Mouse Peritoneal Macrophages." *J. Virol.* 74(19):9240-9244 (2000).

Stokes et al., "Rapid Diagnosis of Influenza A and B by 24-h Fluorescent Focus Assays." *J. Clin. Microbiol.* 26(7):1263-1266 (1988).

Swenson et al., "Rapid detection of influenza virus in cell culture by indirect immunoperoxidase staining with type-specific monoclonal antibodies" *Diagn. Microbiol. Infect. Dis.* 7:265-268 (1987).

Van Voris et al., "Influenza viruses" p. 267-297. In: R. B. Belshe (ed.), Textbook of Human Virology. PSG Publishing Co., Littleton, Mass. (1984).

Walls et al., "Characterization and evaluation of monoclonal antibodies developed for typing influenza A and influenza B viruses" *J. Clin. Microbiol.* 23:240-245 (1986).

Alex Fluor data sheet.[online],[retreived on Jul. 7, 2010]. Retrieved from the internet <URL:http://www.invitrogen.com/site/us/en/home/brands/molecular-probes/key-molecular-probes-products/alexa-fluor/alexa-fluor-488-secondary-antibodies.html>.

Boonpucknavig et al., "Immunofluorescent staining of the surfaces of lymphocytes in suspendion from patients with dengue hemorrhagic fever," *Am. J. Pathology* 85:37-47 (1976).

Chan et al., "Comparison of chemicon simulfluor direct fluorescent antibody staining with cell culture and shell vial direct immunoperoxidase staining for detection of herpes simplex virus and with cytospin direct immunofluorescence staining for detection of varicella-zoster virus," *Clin Diagn Lab Immun.* 8:909-912 (2001).

Iannelli et al., "Simultaneous detection of cucumber mosaic virus, tomato mosaic virus and potato virus Y by flow cytometry," *J. Virol. Methods* 69:137-145 (1997).

Martins, "Development of internal controls for the luminex instrument as part of a multiplex seven-analyte viral respiratory antibody profile." *Clin Diagn Lab Immun.* 9:41-45 (2002).

Rey Nores et al., "Rinderpest virus infection of bovine peripheral blood monocytes." *J. Gen. Viril* 76:2279-2791 (1995).

Schmid et al., "Simultaneous flow cytometric measurement of viability and lymphocyte subset proliferation," *J. Immun. Methods* 247: 175-186 (2001).

Yan et al., "Microsphere-based duplexed immunoassay for influenza virus typing by flow cytometry." *J. Immun. Methods* 284:27-38 (2004).

Sapogenin, From Wikipedia, Dated Aug. 3, 2010.

Saponin, From Wikipedia, Dated Aug. 3, 2010.

Dahl, et al., "Antigen Detection: The Method of Choice in Comparison with Virus Isolation and Serology for Laboratory Diagnosis of Herpes Zoster in Human Immunodeficiency Virus-Infected Patients." *J Clin Microbiol*, 35(2):347-349 (1997).

Ushijima, et al., "Removal of Hiv Antigens and Hiv-Infected Cells in Vitro Using Immunomagnetic Beads." *J Virol Methods*, 29(1):23-31 (1990).

Gittzus and Rubin "Clinical Evaluation of Commercial Conjugates for Direct Immunofluorescence of Herpes Simplex Virus." *J Clin Microbiol*, 6(6):574-577 (1977).

Judson and Van Le: "Flow Cytometry", Prim Care Update OB/GYNs, vol. 4, No. 3, New York NY USA, pp. 87-91 (1977).

Landry and Ferguson "Simulfluor Respiratory Screen for Rapid Detection of Multiple Respiratory Viruses in Clinical Specimens by Immunofluorescence Staining." *J Clin Microbiol*, 38(2):708-711 (2000).

Light Diagnostics, SimulFluor, HSV/VZV, Immunofluorescence Assay, User Guide, May 2007, [retrieved on Dec. 10, 2013] retrieved from internet <URL: http://ebookily.com/pdf/light-diagnostics-chemicon>.

Yan, et al., Multiplexed Flow Cytometric Immunoassay for Influenza Virus Detection and Differentiation, Analytical Chemistry, 77(23):7673-7678, 2005.

Dako Faramount, Aqueous Mounting Medium, May 2007.

De, et al., "A Two-Component Direct Fluorescent-Antibody Assay for Rapid Identification of Bacillus Anthracis." *Emerg Infect Dis*, 8(10):1060-1065 (2002).

Castro, et al., "Ultrasensitive, Direct Detection of a Specific DNA Sequence of *Bacillus anthracis* in Solution," *Analyst* 125:9-11 (2000).

Eriksson, et al., "Lymphocyte Distribution in the Tonsils Prior to and After Influenza Vaccination," *Vaccine* 22(1):57-63 (2003).

Földes-Papp, et al., "Minireview—A New Dimension for the Development of Fluorescence-Based Assays in Solution: From Physical Principles of FCS Detection to Biological Applications," *Exp. Biol. Med.* 227(5):291-300 (2002).

(56) References Cited

OTHER PUBLICATIONS

Földes-Papp, et al., "A New Concept for Ultrasensitive Fluorescence Measurements of Molecules in Solution and Membrane: 1. Theory and a First Application," *J. Immunol. Methods* 286(1-2):1-11 (2004a).

Földes-Papp, et al., "A New Concept for Ultrasensitive Fluorescence Measurements of Molecules in Solution and Membrane: 2. The Individual Immune Molecule," *J. Immunol. Methods* 286(1-2):13-20 (2004b).

Harlow, et al., "Using Antibodies" See "Antibody Addition and Detection for Staining *Caenorhabditis elegans*," Chapt. 6, pp. 195-196 (1999).

Li, et al., "Molecule by Molecule Direct and Quantitative Counting of Antibody-protein Complexes in Solution," *Anal. Chem.* 76(15):4446-51 (2004).

Shin, et al., "Immunocytochemical Staining of p16(ink4a) Protein as an Adjunct Test in Equivocal Liquid-based Cytology," *Diagn. Cytopathol.* 36(5):311-316 (2008).

Xie, et al., "Measurement of the Functional Affinity Constant of a Monoclonal Antibody for Cell Surface Receptors Using Kinetic Exclusion Fluorescence Immunoassay," *J. Immunol. Methods* 304(1-2):1-14 (2005).

\* cited by examiner

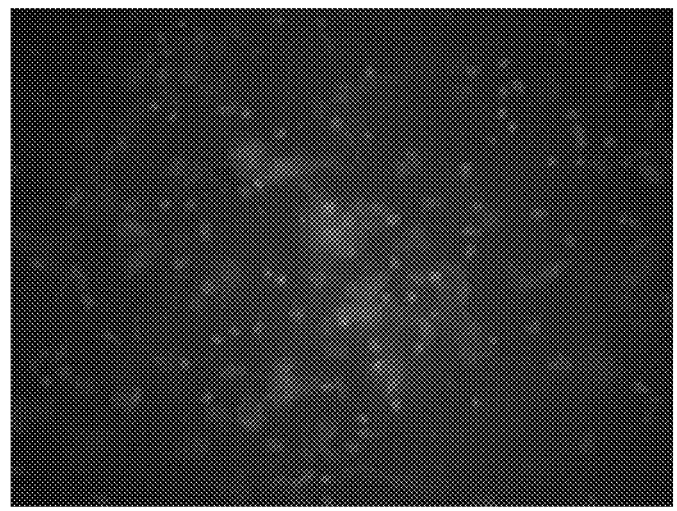
Figure 4

Figure 5

METHODS FOR LIQUID DIRECT FLUORESCENT ANTIBODY INTRACELLULAR VIRUS DETECTION

FIELD OF INVENTION

This invention is related to processing biological samples for direct virus detection in a liquid format. For example, the sample may be derived from the respiratory system. The detection method may use antibodies that directly bind to a viral antigen thereby allowing identification as well as detection. In some instances, the antibodies are labeled monoclonal antibodies. The method may be integrated with a device comprising an algorithm capable of differentiating between a plurality of fluorescent signals.

BACKGROUND

Virus infections (i.e, for exmaple, influenza A and B viruses) are responsible for yearly epidemics in both children and adults. Illnesses caused by influenza A and B viruses are clinically indistinguishable and may cocirculate Van Voris et al., "Influenza viruses" p. 267-297. In: R. B. Belshe (ed.), Textbook Of Human Virology. PSG Publishing Co., Littleton, Mass. (1984). Antiviral chemoprophylaxis and therapy is currently very limited (i.e., for example, influenza A virus-specific agents amantadine and rimantadine). Rapid detection of influenza virus is therefore essential to facilitate patient management and to initiate effective control measures.

Presently known procedures for preparing a specimen for Direct Fluorescence Antibody (DFA) staining are expensive, laborious and time consuming. Usually, a drop of a cell suspension from the specimen is dried on a glass slide and fixed with a precipitating or denaturing fixative such as acetone, methanol and ethanol. These compounds act to reduce the solubility of protein molecules and by disrupt protein tertiary hydrophobic interactions. After fixation, the samples are stained with fluorescent antibodies involving several steps: i) labelling; ii) washing; and iii) adhering a coverslip. Finally, the samples are examined under a fluorescence microscope.

Further problems in DFA techniques are encountered during the microscopic examination because the antibody preparations commonly contain a general protein counter stain, such as Evans Blue, to help in identifying cells. This counter stain also stains non-cellular material which can make identifying cells difficult. Further, if the cells are not completely dry, they can be lost during the processing steps, leading to an inadequate number of cells to make a judgment as to the presence of the virus. Current DFA methods also require a highly skilled technician to prepare, read and interpret results because of the non-specific staining mucus or debris that can be found in the specimen. Cell morphology and staining patterns are also compromised when the cells are dried onto the glass.

What is needed in the art is an improved DFA assay with better accuracy and faster processing time than those currently available.

SUMMARY

This invention is related to processing biological samples for direct virus detection in a liquid format. For example, the sample may be derived from the respiratory system (e.g., a lung aspirate or nasopharyngeal swab sample). The detection method may use antibodies that directly bind to a viral antigen on or in a cell, thereby allowing identification as well as detection. In some instances, the antibodies are labeled monoclonal antibodies. The method may be integrated with a device comprising an algorithm capable of differentiating between a plurality of fluorescent signals.

In one embodiment, the present invention contemplates a method to perform a liquid direct fluorescent assay (LDFA) comprising at least one fluorescent label. In one embodiment, the fluorescent label comprises R-phycoerythrin (PE). In one embodiment, the fluorescent label comprises fluorescein isothiocyanate (FITC). In one embodiment, the fluorescent label is attached to an antibody.

In one embodiment, the present invention contemplates a method, comprising: a) providing: i) a biological sample comprising at least one viral antigen; ii) first and second antibodies, wherein said first antibody reacts with a first viral antigen and does not react with a second viral antigen and is labeled with a first fluorescent tag, and wherein said second antibody reacts with said second viral antigen and does not react with said first viral antigen and is labeled with a second fluorescent tag; b) incubating at least a portion of said sample with said first and second antibodies in a suspension under conditions such that only one of said first and second antibodies bind said antigens; c) identifying a first virus based on detecting said first fluorescent tag. In one embodiment, the method further comprises, step (d) identifying a second virus based on detecting said second fluorescent tag. In one embodiment, the method further comprises identifying said first virus and said second virus based on detecting said first fluorescent tag and said second fluorescent tag. In one embodiment, the first label comprises R-phycoerythrin. In one embodiment, the second label comprises fluorescein isothiocyanate. In one embodiment, the antibody comprises a monoclonal antibody. In one embodiment, the incubating of the first and second antibodies with the suspension is simultaneous. In one embodiment, the incubating of the first and second antibodies with the suspension is serial. In one embodiment, the virus may be selected from the group including, but not limited to, rhinovirus, human papilloma virus, human immunodeficiency virus, hepatitis virus, Newcastle disease virus, cardiovirus, corticoviridae, cystoviridae, epstein-barr virus, filoviridae, hepadnviridae, hepatitis virus, herpes virus, influenza virus, inoviridae, iridoviridae, metapneumovirus, orthomyxoviridae, papovavirus, paramyxoviridae, parvoviridae, polydnaviridae, poxyviridae, reoviridae, rhabdoviridae, semliki forest virus, tetraviridae, toroviridae, varicella zoster virus, vaccinia virus, and vesicular stomatitis virus.

In one embodiment, the present invention contemplates a method, comprising: a) providing: i) a biological sample comprising cells infected with at least one viral antigen; ii) first and second antibodies, wherein said first antibody reacts with a respiratory syncytial viral antigen and does not react with a metapneumovirus viral antigen and is labeled with a first fluorescent tag, and wherein said second antibody reacts with the metapneumovirus viral antigen and does not react with the respiratory syncytial viral antigen and is labeled with a second fluorescent tag; b) incubating at least a portion of said sample with said first and second antibodies in a suspension under conditions such that only one of said first and second antibodies binds said antigens; and c) identifying the viral antigen based on detecting the first or second fluorescent tag. In one embodiment, the method identifies the respiratory viral antigen based on detecting the first fluorescent tag. In one embodiment, the method identifies the metapneumovirus viral antigen based on detecting the second fluorescent tag. In one embodiment, the method identifies the respiratory syncytial viral antigen and the metapneumovirus viral antigen based on detecting the first and second fluorescent tags. In one embodiment, the first label comprises R-phycoerythrin. In one embodiment, the second label comprises fluorescein isothiocyanate. In one embodiment, the antibody comprises a monoclonal antibody. In one embodiment, the incubating of the first and second antibodies with the suspension is simultaneous. In one embodiment, the incubating of the first and second antibodies with the suspension is serial.

In one embodiment, the present invention contemplates a method, comprising: a) providing: i) a biological sample comprising at least one viral antigen; ii) first and second antibodies, wherein said first antibody reacts with an influenza A viral antigen and does not react with an influenza B viral antigen and is labeled with a first fluorescent tag, and wherein said second antibody reacts with said influenza B viral antigen and does not react with said influenza A viral antigen and is labeled with a second fluorescent tag; b) incubating at least a portion of said sample with said first and second antibodies in a suspension under conditions such that only one of said first and second antibodies binds said virus; and c) identifying the at least one viral antigen based on detecting the first or second fluorescent tag. In one embodiment, the method identifies the influenza A viral antigen based on detecting the first fluorescent tag. In one embodiment, the method identifies the influenza B viral antigen based on detecting the second fluorescent tag. In one embodiment, the method identifies the influenza A viral antigen and the influenza B viral antigen based on detecting the first and second fluorescent tags. In one embodiment, the first label comprises R-phycoerythrin. In one embodiment, the second label comprises fluorescein isothiocyanate. In one embodiment, the antibody comprises a monoclonal antibody. In one embodiment, the incubating of the first and second antibodies with the suspension is simultaneous. In one embodiment, the incubating of the first and second antibodies with the suspension is serial.

In one embodiment, the present invention contemplates a method, comprising: a) providing: i) a biological sample comprising at least one viral antigen; ii) first and second antibodies, wherein said first antibody reacts with a parainfluenza viral antigen and does not react with an adenovirus viral antigen and is labeled with a first fluorescent tag, and wherein said second antibody reacts with said adenovirus viral antigen and does not react with said parainfluenza viral antigen and is labeled with a second fluorescent tag; b) incubating at least a portion of said sample with said first and second antibodies in a suspension under conditions such that only one of said first and second antibodies binds said virus; and c) identifying the at least one viral antigen based on detecting the first or second fluorescent tag. In one embodiment, the method identifies the parainfluenza viral antigen based on detecting the first fluorescent tag. In one embodiment, the method identifies the adenovirus viral antigen based on detecting the second fluorescent tag. In one embodiment, the method identifies the parainfluenza viral antigen and the adenovirus viral antigen based on detecting the first and second fluorescent tags. In one embodiment, the first label comprises R-phycoerythrin. In one embodiment, the second label comprises fluorescein isothiocyanate. In one embodiment, the antibody comprises a monoclonal antibody. In one embodiment, the incubating of the first and second antibodies with the suspension is simultaneous. In one embodiment, the incubating of the first and second antibodies with the suspension is serial.

In one embodiment, the present invention contemplates a method, comprising: a) providing; i) a suspension comprising a biological sample, wherein the sample is suspected of comprising at least one viral antigen; ii) at least two fluorescently labeled antibodies, wherein said at least one antigen is capable of interacting with at least one of said fluorescently labeled antibodies, wherein said antibodies are differentially labeled; b) incubating said suspension with said fluorescently labeled antibodies under conditions such that at least one of said fluorescently labeled antibodies binds said at least one viral antigen, thereby forming a labeled antigen-antibody complex; and c) detecting said labeled antigen-antibody complex within said suspension by identifying one fluorescently labeled antibody, thereby identifying the at least one virus antigen. In one embodiment, the biological sample is derived from a patient, thereby diagnosing a virus infection. In one embodiment, the fluorescently labeled antibody comprises a monoclonal antibody. In one embodiment, the viral antigen comprises a respiratory syncytial virus viral antigen. In one embodiment, the fluorescently labeled monoclonal antibody comprises specific affinity for the respiratory syncytial virus viral antigen. In one embodiment, the fluorescently labeled monoclonal respiratory virus antibody comprises a PE fluorescent label. In one embodiment, the viral antigen comprises an influenza virus viral antigen. In one embodiment, the influenza virus viral antigen comprises an influenza A virus viral antigen. In one embodiment, the influenza virus viral antigen comprises an influenza B virus viral antigen. In one embodiment, the fluorescently labeled antibody comprises a monoclonal antibody. In one embodiment, the fluorescently labeled monoclonal antibody comprises specific affinity for the influenza A virus viral antigen. In one embodiment, the fluorescently labeled influenza A monoclonal antibody comprises a PE fluorescent label. In one embodiment, the fluorescently labeled monoclonal antibody comprises specific affinity for the influenza B virus viral antigen. In one embodiment, the fluorescently labeled influenza B monoclonal antibody comprises a FTIC fluorescent label. In one embodiment, the viral antigen comprises an adenovirus viral antigen. In one embodiment, the fluorescently labeled monoclonal antibody comprises specific affinity for the adenovirus viral antigen. In one embodiment, the fluorescently labeled adenovirus monoclonal antibody comprises a FITC fluorescent label. In one embodiment, the viral antigen comprises a parainfluenza virus viral antigen. In one embodiment, the parainfluenza virus viral antigen comprises a parainfluenza 1 virus viral antigen. In one embodiment, the parainfluenza virus viral antigen comprises a parainfluenza 2 virus viral antigen. In one embodiment, the parainfluenza virus viral antigen compries a parainfluenza 3 virus viral antigen. In one embodiment, the fluorescently labeled monoclonal antibody comprises specific affinity for the parainfluenza virus. In one embodiment, the fluorescently labeled parainfluenza monoclonal antibody comprises a PE fluorescent label. In one embodiment, the fluorescently labeled parainfluenza monoclonal antibody comprises specific affinity for the parainfluenza 1 virus viral antigen. In one embodiment, the fluorescently labeled parainfluenza monoclonal antibody comprises specific affinity for the parainfluenza 2 virus viral antigen. In one embodiment, the fluorescently labeled parainfluenza monoclonal antibody comprises specific affinity for the parainfluenza 3 virus viral antigen. In one embodiment, the viral antigen comprises a metapneumovirus viral antigen. In one embodiment, the fluorescently labeled monoclonal antibody comprises a specific affinity for the metapnuemovirus viral antigen. In one embodiment, the fluorescently labeled metapneumovirus monoclonal antibody comprises a FITC fluorescent label. In one embodiment, the viral antigen comprises a varicella zoster viral antigen. In one embodiment, the fluorescently labeled monoclonal antibody comprises a specific affinity for the varicella zoster viral antigen. In one embodiment, the fluorescently labeled varicella zoster monoclonal antibody comprises a PE fluorescent label. In one embodiment, the viral antigen comprises a herpes simplex viral antigen. In one embodiment, the fluorescently labeled monoclonal antibody comprises a specific affinity for a herpes simplex-1 viral antigen. In one embodiment, the fluorescently labeled monoclonal antibody comprises a specific affinity for a herpes simplex-2 viral antigen. In one embodiment, the fluorescently labled herpes simplex monoclonal antibody comprises a FITC fluorescent label. In one embodiment, the suspension includes a staining reagent selected from the group of Evans blue, propidium iodide, acridine orange and combinations thereof. In one embodiment, the suspension includes a detergent. In one embodiment, the detergent is sapogenin. In one embodiment, the incubating of the fluorescently labeled antibodies and suspension is simultaneous. In one embodiment, the incubating of the fluorescently labeled antibodies and suspension is serial.

In one embodiment, the present invention contemplates a method, comprising: a) providing; i) a suspension comprising a biological sample, wherein said sample is suspected of comprising a respiratory syncytial virus viral antigen; ii) at least two fluorescently labeled antibodies, wherein said viral antigen is capable of interacting with at least one of said fluorescently labeled antibodies, wherein antibodies are differentially labeled; b) incubating said suspension with said fluorescently labeled antibodies under conditions such that said respiratory syncytial virus viral antigen binds to at least one of said fluorescently labeled antibodies, thereby forming a labeled antigen-antibody complex; and c) detecting said labeled antigen-antibody complex within said suspension by identifying one fluorescent labeled antibody, thereby identifying said respiratory syncytial virus viral antigen. In one embodiment, the biological sample is derived from a patient, thereby diagnosing a respiratory syncytial virus infection. In one embodiment, the fluorescently labeled antibody comprises a monoclonal antibody. In one embodiment, the fluorescently labeled monoclonal antibody comprises specific affinity for the respiratory syncytial virus viral antigen. In one embodiment, the fluorescently labeled monoclonal respiratory virus antibody comprises a PE fluorescent label. In one embodiment, the suspension includes a staining reagent selected from the group of Evans blue, propidium iodide, acridine orange and combinations thereof. In one embodiment, the suspension includes a detergent. In one embodiment, the detergent is sapogenin. In one embodiment, the respiratory syncytial virus monoclonal antibody is derived from a clone selected from the group comprising clone 3A4D9 or clone 4F9G3. In one embodiment, the incubating of the fluorescently labeled antibodies and suspension is simultaneous. In one embodiment, the incubating of the fluorescently labeled antibodies and suspension is serial.

In one embodiment, the present invention contemplates a method, comprising: a) providing; i) a suspension comprising a biological sample, wherein said sample is suspected of comprising a influenza virus viral antigen; ii) at least two fluorescently labeled antibodies, wherein said viral antigen is capable of interacting with at least one of said fluorescently labeled antibodies, wherein antibodies are differentially labeled; b) incubating said suspension with said fluorescently labeled antibodies under conditions such that at least one of said fluorescently labeled antibodies binds to the influenza virus viral antigen, thereby forming a labeled antigen-antibody complex; and c) detecting said labeled antigen-antibody complex within said suspension by identifying one fluorescently labeled antibody, thereby identifying said influenza virus viral antigen. In one embodiment, the biological sample is derived from a patient, thereby diagnosing an influenza virus infection. In one embodiment, the influenza virus viral antigen comprise an influenza A virus viral antigen. In one embodiment, the influenza virus viral antigen comprise an influenza B virus viral antigen. In one embodiment, the fluorescently labeled antibody comprises a monoclonal antibody. In one embodiment, the fluorescently labeled monoclonal antibody comprises specific affinity for the influenza A virus viral antigen. In one embodiment, the fluorescently labeled influenza A monoclonal antibody comprises a PE fluorescent label. In one embodiment, the fluorescently labeled monoclonal antibody comprises specific affinity for the influenza B virus viral antigen. In one embodiment, the influenza B monoclonal antibody is derived from a clone selected from the group comprising clone 8C7E11 or clone 9B4D9. In one embodiment, the fluorescently labeled influenza B monoclonal antibody comprises a FTIC fluorescent label. In one embodiment, the suspension includes a staining reagent selected from the group of Evans blue, propidium iodide, acridine orange and combinations thereof. In one embodiment, the suspension includes a detergent. In one embodiment, the detergent is sapogenin. In one embodiment, the influenza A monoclonal antibody is derived from a clone selected from the group comprising clone 2H3C5 or clone A(6)B11. In one embodiment, the incubating of the fluorescently labeled antibodies and suspension is simultaneous. In one embodiment, the incubating of the fluorescently labeled antibodies and suspension is serial.

In one embodiment, the present invention contemplates a method, comprising: a) providing; i) a suspension comprising a biological sample, wherein said sample is suspected of having an adenovirus viral antigen; ii) at least two fluorescently labeled antibodies, wherein said viral antigen is capable of interacting with at least one of said fluorescently labeled antibodies, wherein antibodies are differentially labeled; b) incubating said suspension with said fluorescently labeled antibodies under conditions such that said at least one of said fluorescently labeled antibodies binds to said adenovirus viral antigen, thereby forming a labeled antigen-antibody complex; and c) detecting said labeled antigen-antibody complex within said suspension by identifying one fluorescently labeled antibody, thereby identifying said adenovirus viral antigen. In one embodiment, the biological sample is derived from a patient, thereby diagnosing an adenovirus infection. In one embodiment, the fluorescently labeled antibody comprises a monoclonal antibody. In one embodiment, the fluorescently labeled monoclonal antibody comprises specific affinity for the adenovirus viral antigen. In one embodiment, the fluorescently labeled adenovirus monoclonal antibody comprises a FITC fluorescent label. In one embodiment, the suspension includes a staining reagent selected from the group of Evans blue, propidium iodide, acridine orange and combinations thereof. In one embodiment, the suspension includes a detergent. In one embodiment, the detergent is sapogenin. In one embodiment, the adenovirus monoclonal antibody is derived from a clone selected from the group comprising clone 8H2C9, clone 2H10E2, or clone 4H6C9. In one embodiment, the incubating of the fluorescently labeled antibodies and suspension is simultaneous. In one embodiment, the incubating of the fluorescently labeled antibodies and suspension is serial.

In one embodiment, the present invention contemplates a method, comprising: a) providing; i) a suspension comprising a biological sample, wherein the sample is suspected of comprising a parainfluenza virus viral antigen; ii) at least two fluorescently labeled antibodies, wherein said viral antigen is capable of interacting with at least one of said fluorescently labeled antibodies, wherein the antibodies are differentially labeled; b) incubating said suspension with said fluorescently labeled antibody under conditions such that said at least one of said fluorescently labeled antibodies binds to said parainfluenza virus viral antigen, thereby forming a labeled antigen-antibody complex; and c) detecting said labeled antigen-antibody complex by identifying one fluorescently labeled antibody, thereby identifying the parainfluenza virus viral antigen. In one embodiment, the biological sample is derived from a patient, thereby diagnosing a parainfluenza virus infection. In one embodiment, the influenza virus viral antigen comprise a parainfluenza 1 virus viral antigen. In one embodiment, the influenza virus viral antigen comprise a parainfluenza 2 virus viral antigen. In one embodiment, the influenza virus viral antigen comprise a parainfluenza 3 virus viral antigen. In one embodiment, the fluorescently labeled antibody comprises a monoclonal antibody. In one embodiment, the fluorescently labeled monoclonal antibody comprises a PE fluorescent label. In one embodiment, the fluorescently labeled monoclonal antibody comprises specific affinity for a parainfluenza 1 virus viral antigen. In one embodiment, the fluorescently labeled monoclonal antibody comprises specific affinity for a parainfluenza 2 virus viral antigen. In one embodiment, the fluorescently labeled monoclonal antibody comprises specific affinity for a parainfluenza 3 virus viral antigen. In one embodiment, the suspension includes a staining reagent selected from the group of Evans blue, propidium iodide, acridine orange and combinations thereof. In one embodiment, the suspension includes a detergent. In one embodiment, the detergent is sapogenin. In one embodiment, the parainfluenza 1 monoclonal antibody is derived from a clone selected from the group comprising 1D8E10 or 9F61C9. In one embodiment, the parainfluenza 2 monoclonal antibody is derived from a clone selected from the group comprising clone 2E4D7 or clone 5E4E11. In one embodiment, the parainfluenza 3 monoclonal antibody is derived from a clone selected from the group comprising clone 4G5(1)E2H9 or clone 1F6C8. In one embodiment, the incubating of the fluorescently labeled antibodies and suspension is simultaneous. In one embodiment, the incubating of the fluorescently labeled antibodies and suspension is serial.

In one embodiment, the present invention contemplates a method, comprising: a) providing; i) a suspension comprising a biological sample, wherein the sample is suspected of comprising a metapnuemovirus viral antigen; ii) at least two fluorescently labeled antibodies, wherein said viral antigen is capable of interacting with said fluorescently labeled antibodies, wherein antibodies are differentially labeled; b) incubating said suspension with said fluorescently labeled antibodies under conditions such that at least one of said fluorescently labeled antibodies binds to said metapneumovirus viral antigen, thereby forming a labeled antigen-antibody complex; and c) detecting said labeled antigen-antibody complex by identifying one fluorescently labeled antibody, thereby identifying the metapnuemovirus viral antigen. In one embodiment, the biological sample is derived from a patient, thereby diagnosing an metapneumovirus infection. In one embodiment, the fluorescently labeled antibody comprises a monoclonal antibody. In one embodiment, the fluorescently labeled monoclonal antibody comprises a specific affinity for the metapnueovirus viral antigen. In one embodiment, the fluorescently labeled metapneumovirus monoclonal antibody comprises a FITC fluorescent label. In one embodiment, the suspension includes a staining reagent selected from the group of Evans blue, propidium iodide, acridine orange and combinations thereof. In one embodiment, the suspension includes a detergent. In one embodiment, the detergent is sapogenin. In one embodiment, the metapneumovirus monoclonal antibody is derived from a clone selected from the group comprising clone #4, clone #23, or clone #28. In one embodiment, the incubating of the fluorescently labeled antibodies and suspension is simultaneous. In one embodiment, the incubating of the fluorescently labeled antibodies and suspension is serial.

In one embodiment, the present invention contemplates a method, comprising: a) providing; i) a suspension comprising a biological sample, wherein the sample comprises unfixed cells derived from said patient, said suspension further comprising sapogenin and lacking fixatives and non-aqueous solvents; and ii) a fluorescently labeled antibody reactive with a viral antigen; and b) introducing said fluorescently labeled antibody into said cell suspension under conditions such that at least a portion of said antibody reacts with said viral antigen, thereby revealing the viral antigen with said cells. In one embodiment, the sample is derived from a patient suspected of having a virus infection. In one embodiment, the viral antigen is intracellular. In one embodiment, the viral antigen is extracellular. In one embodiment, the viral antigen is attached to a virus. In one embodiment, the viral antigen is displayed on the cell surface.

In one embodiment, the present invention contemplates a cytometer, comprising: a) a sample container configured to reside within a sample tray, wherein said tray is slidably engaged with said cytometer; b) an excitation illumination source positioned to illuminate at least a portion of said container; and c) a detector positioned to collect an emission illumination from said at least a portion of said container. In one embodiment, the sample container comprises a microscope slide having a plurality of wells. In one embodiment, the sample tray slides to serially expose said plurality of containers to said illuminated portion. In one embodiment, the excitation illumination source comprises light emitting diodes. In one embodiment, the emission illumination is derived from a fluorescently labeled monoclonal antibody.

In one embodiment, the present invention contemplates a method, comprising: a) providing: i) a suspension comprising a biological sample, wherein said sample comprises fluorescently labeled biological cells; ii) a cytometer comprising a sample tray, wherein said tray is configured to translate a sample container within said device, wherein said container comprises a plurality of samples; iii) an excitation illumination source targeted to said at least one sample; and b) inserting said sample container into said sample tray under conditions such that a first sample is illuminated by said excitation illumination source; and c) translating said sample container such that a second sample is illuminated by said illumination source. In one embodiment, the fluorescently labeled cell comprises a fluorescent dye. In one embodiment, the fluorescent dye is selected from the group consisting of propidium iodide, ethidium bromide and acridine orange. In one embodiment, the fluorescently labeled cell comprises a fluorescently labeled monoclonal antibody. In one embodiment, the fluorescently labeled antibody comprises R-phycoerythrin. In one embodiment, the fluorescently labeled antibody comprises fluorescein isothiocyanate.

In one embodiment, the present invention contemplates a method, comprising: a) providing: i) a suspension comprising a biological sample, wherein said sample comprises at least two fluorescently labeled viral antigens; and ii) a cytometer capable of differentially detecting the fluorescently labeled viral antigens; b) placing said suspension into said cytometer; and c) detecting at least one of said fluorescently labeled viral antigens. In one embodiment, the detection of a first viral antigen identifies a first virus. In one embodiment, the detection of a second viral antigen identifies a second virus.

In one embodiment, the present invention contemplates a method, comprising: a) providing; i) a suspension comprising a biological sample, wherein the sample is suspected of comprising diseased cells; ii) at least two fluorescently labeled antibodies, wherein said cells are capable of interacting with at least one of said fluorescently labeled antibodies, wherein said antibodies are differentially labeled; and c) incubating said suspension with said fluorescently labeled antibodies under conditions such that at least one of said fluorescently labeled antibodies binds to said cells, thereby forming a labeled cell-antibody complex; and d) detecting said labeled cell-antibody complex within said suspension by identifying one fluorescently labeled antibody, thereby diagnosing said diseased cells. In one embodiment, the biological sample is derived from a patient. In one embodiment, the suspension includes a staining reagent selected from the group of Evans blue, propidium iodide, acridine orange and combinations thereof. In one embodiment, the suspension includes a detergent. In one embodiment, the fluorescently labeled antibody comprises R-phycoerythrin (PE). In one embodiment, the fluorescently labeled antibody comprises fluorescein isothiocyanate (FITC). In one embodiment, the detergent is sapogenin. In one embodiment, the incubating of the fluorescently labeled antibodies and suspension is simultaneous. In one embodiment, the incubating of the fluorescently labeled antibodies and suspension is serial.

Definitions

The term "suspected of" as used herein, refers to a medical condition or set of medical conditions exhibited by a patient that suggest that the patient may contract a particular disease or affliction. For example, these conditions may include, but are not limited to, unusual physical symptoms, unusual emotional symptoms, or unusual biochemical test results.

The term "a liquid cell suspension" or "suspension" as used herein refers to any fluid composition comprising a biological sample, wherein the components of the sample remain mobile relative to any natural or artificial surfaces and/or substrates. The fluid may comprise aqueous components as well as organic components. For example, a liquid cell suspension may comprise phosphate buffered saline.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "derived from" as used herein, refers to the source of an item of interest (i.e., for example, a monoclonal antibody or an energy signature). In one respect, a virus infected cell may be derived from a biological organism (i.e., for example, a human, animal, plant, or patient). In one respect, a monoclonal antibody may be derived from a hybridoma clonal cell line (i.e., for example, a clone). In one respect, an emission illumination may be derived from a fluorescent compound. In one respect, an excitation illumination may be derived from a light source.

The term "based on" as used herein, refers to any process or method, including a mathematical algorithm that results in the ability to quantitate the intensity of a specific excitation source. Further, the process, method, or mathematical algorithm is capable of differentiating between a plurality of excitation sources such that they can be individually quantitated and compared.

The term "detecting" or "detect" or "detected" as used herein, refers to any method and/or device that is capable of identifying an illumination or excitation source.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells. All monoclonal antibodies contemplated herein having specific affinity for a viral antigen are commercially available. (Diagnostics Hybrids, Inc., Athens, Ohio).

The terms "specific affinity", "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "sample" as used herein, is used in its broadest sense and includes environmental and biological samples. Environmental samples include material from the environment such as soil and water. Biological samples may be animal, including, human, fluid (e.g., nasopharyngeal discharge, blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may be collected that is suspected of containing a virus-infected cell, tissue extract, or body fluid.

The term "immunologically active" defines the capability of a natural, recombinant or synthetic peptide (i.e., for example, a collagen-like family protein), or any oligopeptide thereof, to induce a specific immune response in appropriate animals or cells and/or to bind with specific antibodies.

The term "antigenic determinant" as used herein, refers to that portion of a molecule that is recognized by a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody. One such antigenic determinant may be "a viral antigen" wherein an antigen may be displayed on, or within, a virus-infected host cell surface or on a virus coat surface.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The term "label" or "detectable label" are used herein, to refer to any composition detectable by fluorescence, spectroscopic, photochemical, biochemical, immunochemical, electrical, optical or chemical means. For example, such labels may include, but are not limited to, tetramethylrhodamine isothiocyanate (TRITC), Quantum Dots, CY3 and CY5. Other such labels include, but are not limited to, biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "binding" as used herein, refers to any interaction between an infection control composition and a surface. Such as surface is defined as a "binding surface". Binding may be reversible or irreversible. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

The term "fluorescent focus" refers to either one cell or a group of closely adjacent cells that fluoresce when fluorescently labeled antibodies. Some single virus infections produce multi-cell plaques and others result only with infections of one or two cells per viable virus. A viral plaque consisting of many fluorescent staining cells is counted as "one" for viruses such as HSV, VZV, and RSV. Viruses such as influenza A, B, and adenovirus produce only one or a few fluorescent staining cells per viable infectious virus.

The term "virus" refers to obligate, ultramicroscopic, intracellular parasites incapable of autonomous replication (i.e., replication requires the use of the host cell's machinery). Viruses are exemplified by, but not limited to, adenovirus, rhinovirus, human papilloma virus, human immunodeficiency virus, hepatitis virus, Newcastle disease virus, cardiovirus, corticoviridae, cystoviridae, epstein-barr virus, filoviridae, hepadnviridae, hepatitis virus, herpes virus, influenza virus, inoviridae, iridoviridae, metapneumovirus, orthomyxoviridae, papovavirus, parainfluenza virus, paramyxoviridae, parvoviridae, polydnaviridae, poxyviridae, reoviridae, respiratory syncytial virus, rhabdoviridae, semliki forest virus, tetraviridae, toroviridae, vaccinia virus, and vesicular stomatitis virus. "Virus" also includes an animal virus that is not a plus-strand RNA virus as exemplified by, but not limited to, Arenaviridae, Baculoviridae, Birnaviridae, Bunyaviridae, Cardiovirus, Corticoviridae, Cystoviridae, Epstein-Barr virus, Filoviridae, Hepadnviridae, Hepatitis virus, Herpesviridae, Influenza virus, Inoviridae, Iridoviridae, Metapneumovirus, Orthomyxoviridae, Papovaviru, Paramyxoviridae, Parvoviridae, Polydnaviridae, Poxyviridae, Reoviridae, Rhabdoviridae, Semliki Forest virus, Tetraviridae, Toroviridae, Vaccinia virus, Vesicular stomatitis virus.

The term "pathogen" as used herein, refers to any sub-microscopic or microscopic organism comprising at least one antigen. For example, a pathogen comprising an antigen can be detected and identified by a fluorescently labeled monoclonal antibody having specific affinity to the pathogen antigen. Representative examples, of pathogens include, but are not limited to, bacteria, fungi, yeast, viruses, or any microbe.

The term "respiratory virus" as used herein, refers to any virus capable of infecting pulmonary tissues (i.e., for example, lung tissue). For example, a respirator virus includes, but is not limited to, influenza, parainfluenza, adenovirus, rhinovirus, herpes simplex virus, respiratory syncytial virus, hantavirus, or cytomegalovirus.

BRIEF DESCRIPTION OF THE FIGURES

FIG. 4 shows exemplary data of fluorescently labeled FITC MAb incubation in adenovirus-infected cells. Upper Panel: Negative control specimen stained with propidium iodide and Evans blue. Lower Panel: Apple green stain: FITC MAb-labeled adenoirus infected cell.

FIG. 5 shows exemplary data of fluorescently labeled PE MAb incubation in respiratory virus-infected cells. Upper Panel: Negative control specimen stained with propidium iodide and Evans blue. Lower Panel: Gold stain: PE MAb-labeled adenoirus infected cell.

FIGS. 9A-B present exemplary data showing a comparison of LDFA (MAbs: 10B12C11+A(6)B11) versus DFA viral detection for influenza A (FIG. 9A) and influenza B (FIG. 9B).

FIGS. 10A-B present exemplary data showing a comparison of LDFA (MAbs: 10B12C11+A(6)B11) versus DFA viral detection for respiratory virus (FIG. 10A) and metapneumovirus (FIG. 10B).

FIGS. 11A-B present exemplary data showing a comparison of LDFA (MAbs: 10B12C11+A(6)B11) versus DFA viral detection for adenovirus (FIG. 11A) and parainfluenza virus 1 (FIG. 11B).

FIGS. 12A-B present exemplary data showing a comparison of LDFA (MAbs: 10B12C11+A(6)B11) versus DFA viral detection for parainfluenza virus 2 (FIG. 12A) and parainfluenza virus 3 (FIG. 12B).

FIGS. 13A-B present exemplary data showing a comparison of LDFA (MAbs: 10B12C11+A(6)B11) versus DFA viral detection for parainfluenza (1-3) (FIG. 13A); and a combined mixture of viruses in FIGS. 9-13A (FIG. 13B).

DETAILED DESCRIPTION OF THE INVENTION

Figure 1:
FIG. 1 shows exemplary data of fluorescently labeled monoclonal antibody (MAb) incubation in non-influenza A virus infected cells (i.e, a negative control) Yellow stain: Background signal.

This invention is related to processing biological samples for direct virus detection in a liquid format. For example, the sample may be derived from the respiratory system. The detection method may use antibodies that directly bind to a viral antigen, thereby allowing identification as well as detection. In some instances, the antibodies are labeled monoclonal antibodies. The method may be integrated with a device comprising an algorithm capable of differentiating between a plurality of fluorescent signals.

In one embodiment, the present invention contemplates a method for detecting and identifying a viral antigen using an image of a processed biological cell specimen and an algorithm to determine if cells are positive or negative for viral infection. In one embodiment, the method comprises a liquid sample during preparation, processing, and examination.

I. Virus Infections

During epidemics, viruses may be a significant cause of morbidity and mortality, especially in the elderly and in patients with chronic pulmonary and/or cardiovascular disorders Swenson et al., "Rapid detection of influenza virus in cell culture by indirect immunoperoxidase staining with type-specific monoclonal antibodies" *Diagn. Microbiol. Infect. Dis.* 7:265-268 (1987). Appropriate infection control measures and proper patient management may be optimized by rapid detection and identification of virus in clinical specimens.

A virus is a small infectious organism—much smaller than a fungus or bacterium—that must invade a living cell to reproduce (e.g., replicate). The virus attaches to a cell (called the host cell), enters it, and releases its DNA or RNA inside the cell. The virus's DNA or RNA is the genetic material containing the information needed to replicate the virus. The virus's genetic material takes control of the cell and forces it to replicate the virus. The infected cell usually dies because the virus keeps it from performing its normal functions. When it dies, the cell releases new viruses, which go on to infect other cells.

Some viruses do not kill the cells they infect but instead alter the cell's functions. Sometimes the infected cell loses control over normal cell division and becomes cancerous. Some viruses leave their genetic material in the host cell, where the material remains dormant for an extended time (e.g., latent infection). When the cell is disturbed, the virus may begin replicating again and cause disease.

Viruses usually infect one particular type of cell. For example, cold viruses infect only cells of the upper respiratory tract. Additionally, most viruses infect only a few species of plants or animals. Some infect only people. Many viruses commonly infect infants and children.

Viruses are spread (e.g., transmitted) in various ways. Some are swallowed, some are inhaled, and some are spread by the bites of insects and other parasites (i.e., for example, mosquitoes and ticks). Some are spread sexually.

1. Defenses

Most biological organisms have a number of defenses against viruses. For example, physical barriers, such as the skin, discourage easy entry. Infected cells also make interferons, substances that can make uninfected cells more resistant to infection by many viruses.

When a virus enters the body, the virus may trigger the body's immune defenses. These defenses begin with white blood cells, such as lymphocytes and monocytes, which produce antibodies that attack and destroy the virus or the infected cells. Production of antiviral antibodies produces a subsequent state of immunity, wherein the white blood cells are now programmed to immediately respond to re-infection. These states of immunity can be artificially induced by vaccination with non-infectious viral particles. Vaccination initiates the production of antibodies from a variety of white blood cells, thereby producing antibodies that are polyclonal in nature.

2. Types of Viral Infections

Probably the most common viral infections are those of the upper respiratory airway (i.e., for example, nose, throat, etc.). These infections include sore throat, sinusitis, and the common cold. Influenza is a viral respiratory infection. In small children, viruses also commonly cause croup and inflammation of the windpipe (i.e., for example, laryngotracheobronchitis) or other airways deeper inside the lungs. Respiratory infections are more likely to cause severe symptoms in infants, older people, and people with a lung or heart disorder.

Some viruses (i.e., for example, rabies virus, West Nile virus, and several different encephalitis viruses) infect the nervous system. Viral infections also develop in the skin, sometimes resulting in warts or other blemishes.

Other common viral infections are caused by herpes viruses. Eight different herpes viruses infect people, including but not limited to, herpes simplex virus type 1, herpes simplex virus type 2, and varicella-zoster virus cause infections that produce blisters on the skin or mucus membranes. Another herpes virus, Epstein-Barr virus, causes infectious mononucleosis. Cytomegalovirus is a cause of serious infections in newborns and in people with a weakened immune system. Cytomegalovirus can also produce symptoms similar to infectious mononucleosis in people with a healthy immune system. Human herpes viruses 6 and 7 cause a childhood infection called roseola infantum. Human herpes virus 8 has been implicated as a cause of cancer (Kaposi's sarcoma) in people with AIDS.

All of the herpes viruses cause lifelong infection because the virus remains within its host cell in a dormant (latent) state. Sometimes the virus reactivates and produces further episodes of disease. Reactivation may occur rapidly or many years after the initial infection.

3. Diagnosis

Common viral infections are usually diagnosed based on symptoms. For infections that occur in epidemics (i.e., for example, influenza), the presence of other similar cases may help doctors identify a particular infection. For other infections, blood tests and cultures (growing microorganisms in the laboratory from samples of blood, body fluid, or other material taken from an infected area) may be done. Blood may be tested for antibodies to viruses or for antigens (proteins on or in viruses that trigger the body's defenses). Polymerase chain reaction (PCR) techniques may be used to make many copies of the viral genetic material, enabling doctors to rapidly and accurately identify the virus. Tests are sometimes done quickly—for instance, when the infection is a serious threat to public health or when symptoms are severe. A sample of blood or other tissues is sometimes examined with an electron microscope, which provides high magnification with clear resolution.

4. Treatment

Drugs that combat viral infections are called antiviral drugs. Many antiviral drugs work by interfering with replication of viruses, such as drugs used to treat human immunodeficiency virus (HIV) infection. Because viruses replicate inside cells using the cells' own metabolic functions, there are only a limited number of metabolic functions that antiviral drugs can target. Therefore, antiviral drugs are difficult to develop. Further, effective antiviral drugs can be toxic to human cells. Viruses can also develop resistance to antiviral drugs.

Other antiviral drugs strengthen the biological immune response to the viral infection. These drugs include several types of interferons, immunoglobulins, and vaccines. Interferon drugs are replicas of naturally occurring substances that slow or stop viral replication. Immune globulin is a sterilized solution of antibodies (also called immunoglobulins) collected from a group of people. Vaccines are materials that help prevent infection by stimulating the body's natural defense mechanisms. Many immune globulins and vaccines are given before exposure to a virus to prevent infection. Some immune globulins and some vaccines, such as those for rabies and hepatitis B, are also used after exposure to the virus to help prevent infection from developing or reduce the severity of infection. Immune globulins may also help treat some established infections and also prevent infection after future exposures to the virus.

Most antiviral drugs can be given by mouth. Some can also be given by injection into a vein (intravenously) or muscle (intramuscularly). Some are applied as ointments, creams, or eye drops or are inhaled as a powder.

Antibiotics are not effective against viral infections, but if a person has a bacterial infection in addition to a viral infection, an antibiotic is often necessary.

II. Viral Detection Assays

Infectious disease rates and immunization strategies continue to evolve in the United States and worldwide in response to societal needs, national defense, and evolutionary changes in the organisms producing disease. Immunizations are performed to prevent many infections, while prophylactic population screening is utilized for infections lacking effective vaccines and for those diseases having a low enough incidence that mass immunization is not deemed most efficacious.

The current method for diagnosis of disease, determining exposure to biological materials such as pathogens, or monitoring immunization status varies depending on the specific assay. Some methods employ an in vivo assay. Others require a biological sample, such as blood or serum, to be obtained and tested. Tests performed usually are one of the non-homogeneous type diagnostic methods such as enzyme-linked immunosorbant assay (hereinafter "ELISA"), radioimmunoassay (hereinafter "RIA"), or agglutination. All are surface-binding, heterogeneous assays and require the antigen of interest to interact with a surface to achieve success, often at the expense of high non-specific binding and loss of specificity.

The embodiments described herein improve upon previously reported immunoassays by providing a totally liquid environment encompassing all steps of the method.

A. Non-Fluorescent Antibody Assays

A general method believed capable of detecting viruses in solution was reported using composite organic-inorganic nanoclusters displaying antibodies that capture fluorescently labeled infected cells. Sun et al., "Multiplexed Detection of Analytes in Fluid Solution," United States Patent Publication No. 2007/0279626. The nanocluster-antibody-cell complex is then subjected to FACS in conjunction with Raman analysis to determine the number of captured infected cells. A liquid-phase immunodiagnostic assay has been reported that generates a biochemical reporter when antigen/antibody complex is acted upon by a first and second enzyme. Clemmons et al., "Liquid-Phase Immunodiagnostic Assay," U.S. Pat. No. 5,637,473. Suggested antigen/antibody complexes include various virus-related epitopes. Analyte detection from clinical samples of patients suspected of having a disease was reported by reacting a sample with a nucleic acid-labeled binding construct. The binding construct may be an antibody having affinity to an analyte. Once bound, the antibody/analyte complex is isolated and the nucleic acid label is amplified and identified to quantitate the captured analytes. Lawton, "Soluble Analyte Detection and Amplification," U.S. Pat. No. 7,341,837; and United States Patent Publication No. 2005/0048500.

B. Indirect Immunofluorescence

Indirect immunofluorescence represents a method in which a first unlabeled IgG antibody directed against a specific antigen is then detected by use of a labeled (i.e., for example, fluorescently labeled) anti-IgG of the same species as the first antibody. For example, labeled goat anti-rabbit IgG antibody can be used against a specific first antibody that was raised in rabbits.

Flow cytometry by using FACS methodology has been used for monitoring intracellular influenza A replication by using fluorescently labeled monoclonal antibodies directed to matrix protein I and nucleoprotein. In this system, adherent MDCK cells were first inoculated with virus containing sample, then fixed and dehydrated with ethanol and paraformaldehyde/ethanol. Schulze-Horsel et al., "Flow Cytometric Monitoring of Influenza A Virus Infection in MDCK Cells During Vaccine Production," BMC Biotechnol. 8:45 (2008); and Lonsdale et al., "A Rapid Method for Immunotitration of Influenza Viruses Using Flow Cytometry," J. Virol. Methods, 110(1):67-71, (2003)).

In vivo antibody production was studied in mice infected with influenza virus using a FACS immunofluorescence method. The data demonstrated that B cells isolated from infected spleen cells did not undergo isotype switching from natural IgM isotypes to influenza-specific isotypes during the course of the infection. Baumgarth et al., "Innate and Acquired Humoral Immunities to Influenza Virus are Mediated by Distinct Arms of the Immune System," PNAS 96:2250-2255 (1999).

Detection of influenza virus was compared between various processing methods using cell culture-based indirect immunofluorescence staining Chamber slides, shell vials, standard virus isolation, and nasal wash specimens were all tested using monoclonal antibodies specific for antigens of either influenza A virus (i.e., matrix protein or nucleoprotein) or influenza B virus (i.e., nucleoprotein or hemagglutinin) Walls et al., "Characterization and evaluation of monoclonal antibodies developed for typing influenza A and influenza B viruses" J. Clin. Microbiol. 23:240-245 (1986). These comparisons indicated that indirect immunofluorescence tests were difficult to interpret due to an abundance of mucus debris despite vigorous washing and, occasionally, inadequate numbers of intact cells. Stokes et al., "Rapid Diagnosis of Influenza A and B by 24-h Fluorescent Focus Assays," J. Clin. Microbiol. 26(7):1263-1266 (1988). Influenza infections may also be detected by capturing naturally produced antibodies within a clinical sample onto a surface coated with recombinantly produced influenza A M2 protein. Kendal et al., "Improved Expression of Influenza A M2 Protein in Baculovirus and Uses of M2 Protein," WO/1993/003173. Influenza virus infection may also be detected using a sandwich immunofluorescent assay where anti-influenza antiserum recognizing NP, M1, HA and NA protein were reacted with fixed and permeabilized HeLa cells. The resultant protein-antibody complexes were visualized with FITC-labeled anti-rabbit IgG antibody. Shiratsuchi et al., "Phosphatidylserine-Mediated Phagocytosis of Influenza A Virus-Infected Cells by Mouse Peritoneal Macrophages," J. Virol. 74(19):9240-9244 (2000).

Influenza virus was detected on tissue impression smears using unlabeled influenza A group-specific monoclonal antibody detected by an anti-mouse FITC secondary antibody. The method does not teach use of sapogenin, or propidium iodide. Selleck et al., "Rapid Diagnosis of Highly Pathogenic Avian Influenza Using Pancreatic Impression Smears," Avian Diseases 47(s3):1190-1195 (2002).

C. Direct Fluorescent Assays (DFAs)

Direct immunofluorescence comprises the use of a labeled reactant (i.e., for example, an antibody) which both detects and indicates the presence of an unlabeled reactant (i.e., for example, an antigen, viral epitope, or cell epitope). In some cases, the label comprises a fluorescent molecule. In some cases, it is advantageous to use primary antibodies directly labeled with a fluorescent molecule. This direct labeling decreases the number of steps in the staining procedure and, more importantly, often avoids cross-reactivity and high background problems.

1. Non-Liquid Based DFA

Direct detection of viruses has been accomplished by using an immunofluorescence or enzyme-linked immunosorbent assay (ELISA). Direct-smear examinations by immunofluorescence are problematic due to low sensitivity and non-specific background staining. Alternatively, a shell vial centrifugation assay has been adapted for detection of the influenza viruses. Espy et al., "Rapid detection of influenza virus by shell vial assay with monoclonal antibodies" J. Clin. Microbiol. 24:677-679 (1986); and Stokes et al., "Rapid diagnosis of influenza A and B by 24-h fluorescent focus assay" J. Clin. Microbiol. 26:1263-1266 (1988).

Some cell culture based techniques to detect influenza A and influenza B viruses in clinical respiratory specimens use Madin-Darby canine kidney cells, which are very sensitive to infection with influenza virus. Such methods take at least a week of incubation to observe the development of cytopathic effects resulting from viral infection of the cell culture by the sample. Frank et al., "Comparison of different tissue cultures for isolation and quantitation of influenza and parainfluenza viruses" *J. Clin. Microbiol.* 10:32-36 (1979); and Meguro et al., "Canine kidney cell line for isolation of respiratory viruses" *J. Clin. Microbiol.* 9:175-179 (1979). Clinical specimen smears were also examined by using a direct immunofluorescence assay. These smears were subjected to several steps to prepare and dry the sample on a microscope slide before viewing on a microscope. Influenza was detected using FTIC-labeled antibodies along with counter staining with Evan's blue. This method is not enhanced by using sapogenin to improve the detectable signal or using a combination counterstain with propidium iodide. Mills et al., "Detection of Influenza Virus by Centrifugal Inoculation of MDCK Cells and Staining with Monoclonal Antibodies," *J. Clin. Microbiol.* 27(11):2505-2508 (1989).

Currently, there are two (2) general methods (i.e., standard DFA and cytospin DFA) used for staining respiratory specimens directly using fluorescent labeled antibodies to detect the presence of respiratory viruses such as influenza A and B, respiratory syncytial virus, etc. These assay protocols are compared to one embodiment contemplated herein (i.e., for example, liquid DFA; LDFA) that is much faster. See, Table 1.

TABLE 1

Estimated time to results for one specimen using a DFA

| | Standard DFA | Cytospin DFA* |
|---|---|---|
| Drying | 30-60 minutes | 5-10 minutes |
| Fixing | 10 minutes | 10 minutes |
| Incubation | 15-30 minutes | 15-30 minutes |
| Manipulation time | 2 minutes | 2 minutes |
| Total time to result | 47-102 minutes | 32-52 minutes |

*Cytospin is done only for the Screen. If the Cytospin preparation is positive, the lab still has to run the standard 8 well ID slide which takes 47-102 minutes.

The current standard and cytospin DFAs require numerous and lengthy laboratory steps including, i) centrifugation to collect and concentrate the cells from the specimen (this step varies depending on the laboratory. It could range from 10 minutes to up to 30 minutes if multiple rinses are performed); ii) drying the deposited cells on the slide; iii) fixing the cells using a dehydration agent (i.e., for example, Acetone); iv) incubating the adhered, fixed cells with respective fluorescein isothiocyanate (FITC) labeled Ab's at 37° C.; and v) manipulating the labeled/fixed cells for microscope viewing and examination for the presence of fluorescent cells. One significant drawback of the current DFAs is that the microscope viewing and examination for fluorescently labeled cells is done manually (i.e., by visual inspection). Further, as a single fluorescent label is usually used for each antibody, a separate sample must be processed in series in order to detect the presence of each suspected virus.

Fixatives in the DFAs is usually a dehydration agent (i.e., for example, acetone) which immobilizes proteins, adheres cells to a glass slide and permeabilizes the cells for entry of MAb's to react with intracellular antigen. Staining agents in the DFAs are usually directly labeled FITC MAb's for the viral antigens in combination with a protein stain (i.e., for example, Evans Blue) for counter-staining the cells.

2. Liquid DFA (LDFA)

Currently available DFAs would require a different aliquot to detect and identify each virus (i.e., eight aliquots total) using the lengthy and laborious techniques described above. For example, non-liquid DFAs detection of eight (8) viruses require thirty-seven (37) laboratory manipulations. In contrast, an LDFA embodiment contemplated by the present invention comprises only fourteen (14) laboratory manipulations using the serial analysis of three aliquots of a liquid sample. In one embodiment, the method further comprises a fourth aliquot of the liquid sample without any labeled monoclonal antibodies as a control.

Fluorescently labeled ligands (i.e., for example, small molecules, peptides) have been used in solution-based diagnostic assays by detecting antibodies by measuring changes in fluorescence polarization. A fluorescently labeled ligand will undergo an alteration in molecular spin rate, thereby changing its emission pattern when the ligand binds with a binding partner (i.e., for example, a labeled antigen binding with an antibody). For instance, the method may detect naturally produced antibodies in biological samples from patient that are infected with a microorganism (i.e., for example, bacteria or virus). Cullum et al., "Fluorescence Polarization Instruments and Methods For Detection of Exposure to Biological Materials By Fluorescence Polarization Immunoassay of Saliva, Oral or Bodily Fluids," U.S. Pat. No. 7,408,640 (2008); and United States Patent Publication No. 2005/0095601 (both herein incorporated by reference).

Solutions of fluorescently labeled monoclonal antibodies have been stabilized with azo-compounds for use to identify *Mycoplasma pneumonia* in an ELISA format. The infected cells were immobilized to a microwell plate before incubation with the antibodies. These methods do not depend upon improved cell permeability (i.e., for example, by addition of sapogenin) or counterstaining with propidium iodide, and does not contemplate detection of viruses (i.e., for example, influenza). Sawayanagi et al., "Stable Antibody Solution and Method For Preparing the Same," U.S. Pat. No. 5,602,234 (1997)(herein incorporated by reference).

In one embodiment, the present invention contemplates a method to perform LDFA comprising incubating a liquid sample with a permeabilization agent and at least one cell stain. Although it is not necessary to understand the mechanism of an invention, it is believed that this is a distinct advantage over currently available non-liquid DFA's which perform the analogous steps of fixation and staining in two separate steps. In one embodiment, the permeabilization agent comprises acetone. In one embodiment, the cell stain comprises a specific protein stain (i.e., for example, Evans Blue) at approximately one-eigth the amount in currently available DFAs and a non-specific cell nuclei stain (i.e., for example, propidium iodide).

In one embodiment, the present invention contemplates a method to perform LDFA comprising preparing a liquid sample for examination in less than ten (10) minutes. In one embodiment, the method comprises incubating the liquid sample at room temperature with a permeabilization agent (i.e., for example, acetone) and at least one cell stain for approximately five (5) minutes. In one embodiment, the method comprises rinsing and centrifuging the permeabilized and stained liquid sample at room temperature for approximately two (2) minutes. The LDFA has significant advantages over currently known DFA assays by significantly improving the ability of a laboratory technician to quickly identify and enumerate virus-infected cells in a liquid specimen. See, Table 2.

TABLE 2

Estimated time to results for one specimen using LDFA.

|  | Liquid DFA |
| --- | --- |
| Drying | none |
| Fixing | none |
| Incubation | 5 minutes |
| Wash | 2 minutes |
| Manipulation time | 2 minutes |
| Total time to result | 9 minutes |

No fixatives are necessary in LDFAs to adhere cells to a glass slide, but dehydration agents may be useful as a cell permeabilzation agent. Further, a detergent (i.e., for example, sapogenin) may be used to optimally permeabilize the cells for entry of the MAb's to react with intracellular antigen. Staining agents in LDFAs are usually directly labeled fluorescent MAb's for a viral antigen in combination with a low concentration of Evans Blue (i.e., for example, to quench fluorescent background staining) and propidium iodide, a fluorescent nuclear stain, used to help identify what a cell is in relation to the fluorescence from FITC and/or PE with the nuclear stains in cells.

Figure 2:
FIG. 2 shows exemplary data of fluorescently labeled MAb incubation in a 1+ dilution aliquot (low titer) of influenza A virus-infected cells. Apple green stain: MAb-labeled cells. Yellow stain: Background signal.
Figure 3:
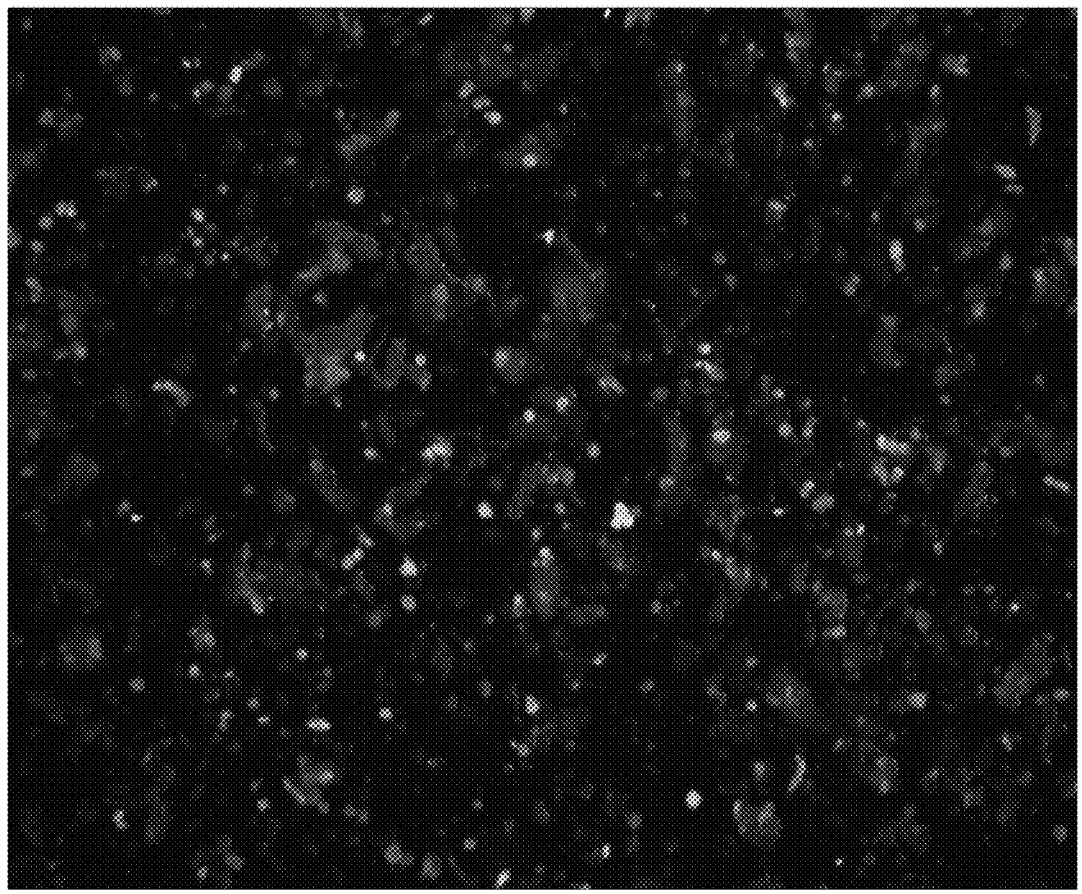
FIG. 3 shows exemplary data of fluorescently labeled MAb incubation in a 4+ dilution aliquot (high titer) of influenza A virus-infected cells. Apple green stain: FITC MAb-labeled virus infected cells. Yellow stain: Background signal.

Such labeling has been observed to be proportional to the number of infected cells (i.e., for example, infected with influenza A) present in the test solution. See, FIGS. 1, 2, and 3 performed in accordance with Example I. Similar data was obtained with HSV-1 infected cells (data not shown). One advantage of the currently disclosed LDFA is that the cell suspensions do not require drying or covering with a mounting fluid to faciliate microscopic examination. Although a wash step is also not required, it is believed that an embodiment of the present invention that comprises a wash step will have a lower background signal. These preliminary studies demonstrated very good sensitivity based on a comparison of the number of MAb-positive cells in the scraped suspension to the stained monolayer.

The present LDFA method was compared to conventional DFA methods demonstrating the specificity and selectivity of the LDFA versus a traditional DFA for: i) Influenza A (Flu A) MAb combination of clone 2H3C5 and clone A(6)B11; ii) influenza B (Flu B) MAb combination of clone 8C7E11 and clone 9B4D9; iii) respiratory virus (RSV) MAb combination of clone 3A4D9 and clone 4F9G; iv) metapneumovirus (MPV) MAb combination of clone #4, clone #23, and clone #28; v) adenovirus (ADV) MAb combination of clone 8H2C9, clone 2H10E2, and clone 4H6C9; vi) parainfluenza (PIV) virus 1 MAb combination of clone 1D8E10 and clone 9F61C9; vii) parainfluenza virus 2 MAb combination of clone 2E4D7 and clone 5E4E11; viii) parainfluenza virus 3 MAb combination of clone 4G5(1)E2H9 and clone 1F6C8; ix) pooled parainfluenza 1-3 MAbs as described above and x) combined mixture of i)-ix). Representative micrographs show MAb-positive signals for LDFA vents DFA results. See, FIG. 4 and FIG. 5, respectively. Further, in a single MAb assay system, LDFA and DFA identification of virus-positive cells versus virus-negative cells are compared. See, Tables 3 through 8 respectively.

TABLE 3

Cross-correlation between LDFA and DFA for Influenza A virus detection and identification using the LDFA Influenza A&B reagent compared to the Individual Influenza A reagent..
TABLE 3: Study Site 4 - $D^3$ Ultra Duet R-PE identification of Influenza A virus positive specimens

| Direct Specimen | | $D^3$ Ultra Final Identification (Influenza A virus) | |
| --- | --- | --- | --- |
| (637 Specimens) | | Pos | Neg |
| $D^3$ Ultra Duet Flu A/Flu B | Pos | 46 | 2 |
| | Neg | 1 | 588 |
| Positive Percent Agreement (PPA) | | 97.6% (46/47) | |
| 95% CI- PPA | | 88.9, 99.6% | |
| Negative Percent Agreement (NPA) | | | 99.7% (588/590) |
| 95% CI- NPA | | | 98.8, 99.9% |

TABLE 4

Cross-correlation between LDFA and DFA for Influenza B virus detection and identification using the LDFA Influenza A&B reagent compared to the Individual Influenza B reagent.
TABLE 4: Study Site 4 - $D^3$ Ultra Duet FITC identification of Influenza B virus positive specimens

| Direct Specimen | | $D^3$ Ultra Final Identification (Influenza B virus) | |
| --- | --- | --- | --- |
| (637 Specimens) | | Pos | Neg |
| $D^3$ Ultra Duet Flu A/Flu B | Pos | 197 | 4 |
| | Neg | 1 | 435 |
| Positive Percent Agreement (PPA) | | 99.5% (197/198) | |
| 95% CI- PPA | | 97.2, 99.9% | |
| Negative Percent Agreement (NPA) | | | 99.1% (435/439) |
| 95% CI- NPA | | | 97.7, 99.7% |

TABLE 5

Cross-correlation between LDFA and DFA for RSV detection and identification using the LDFA Influenza RSV&MPV reagent compared to the Individual RSV reagent.
TABLE 5: Study Site 4 - $D^3$ Ultra Duet R-PE identification of RSV positive specimens

| Direct Specimen | | $D^3$ Ultra Final Identification (RSV) | |
| --- | --- | --- | --- |
| (637 Specimens) | | Pos | Neg |
| $D^3$ Ultra Duet RSV/MPV | Pos | 29 | 0 |
| | Neg | 0 | 608 |
| Positive Percent Agreement (PPA) | | 100% (29/29) | |
| 95% CI- PPA | | 88.3, 100% | |
| Negative Percent Agreement (NPA) | | | 100% (608/608) |
| 95% CI- NPA | | | 99.4, 100% |

TABLE 6

Cross-correlation between LDFA and DFA for MPV detection and identification using the LDFA Influenza RSV&MPV reagent compared to the Individual MPV reagent.
TABLE 6: Study Site 4 -
$D^3$ Ultra Duet FITC identification of MPV positive specimens

| Direct Specimen | | $D^3$ MPV DFA Reagent | |
|---|---|---|---|
| (637 Specimens) | | Pos | Neg |
| $D^3$ Ultra Duet RSV/MPV | Pos | 15 | 0 |
| | Neg | 0 | 622 |
| Positive Percent Agreement (PPA) | | 100% (15/15) | |
| 95% CI-PPA | | 79.6, 100% | |
| Negative Percent Agreement (NPA) | | | 100% (622/622) |
| 95% CI-NPA | | | 99.4, 100% |

TABLE 7

Cross-correlation between LDFA and DFA for Parainfluenza virus detection and identification using the LDFA Parainfluenza pool&Adenovirus reagent compared to the Individual Parainfluenza reagents.
TABLE 7: Study Site 4 -
$D^3$ Ultra Duet R-PE identification of Parainfluenza virus 1, 2, and 3 positive specimens

| Direct Specimen | | $D^3$ Ultra Final Identification (Parainfluenza) | |
|---|---|---|---|
| (637 Specimens) | | Pos | Neg |
| $D^3$ Ultra Duet PIV/Adeno | Pos | 6 | 0 |
| | Neg | 0 | 631 |
| Positive Percent Agreement (PPA) | | 100% (6/6) | |
| 95% CI-PPA | | 56.6, 100% | |
| Negative Percent Agreement (NPA) | | | 100% (631/631) |
| 95% CI-NPA | | | 99.4, 100% |

TABLE 8

Cross-correlation between LDFA and DFA for Adenovirus detection and identification using the LDFA Influenza Parainfluenza pool&Adenovirus reagent compared to the Individual Adenovirus reagent..
TABLE 8: Study Site 4 -
$D^3$ Ultra Duet FITC identification of Adenovirus positive specimens

| Direct Specimen | | $D^3$ Ultra Final Identification (Adenovirus) | |
|---|---|---|---|
| (637 Specimens) | | Pos | Neg |
| $D^3$ Ultra Duet PIV/Adeno | Pos | 1 | 0 |
| | Neg | 0 | 636 |
| Positive Percent Agreement (PPA) | | % (1/1) | |
| 95% CI-PPA | | 20.7, 100% | |
| Negative Percent Agreement (NPA) | | | 100% (636/636) |
| 95% CI-NPA | | | 99.4, 100% |

Figure 9:
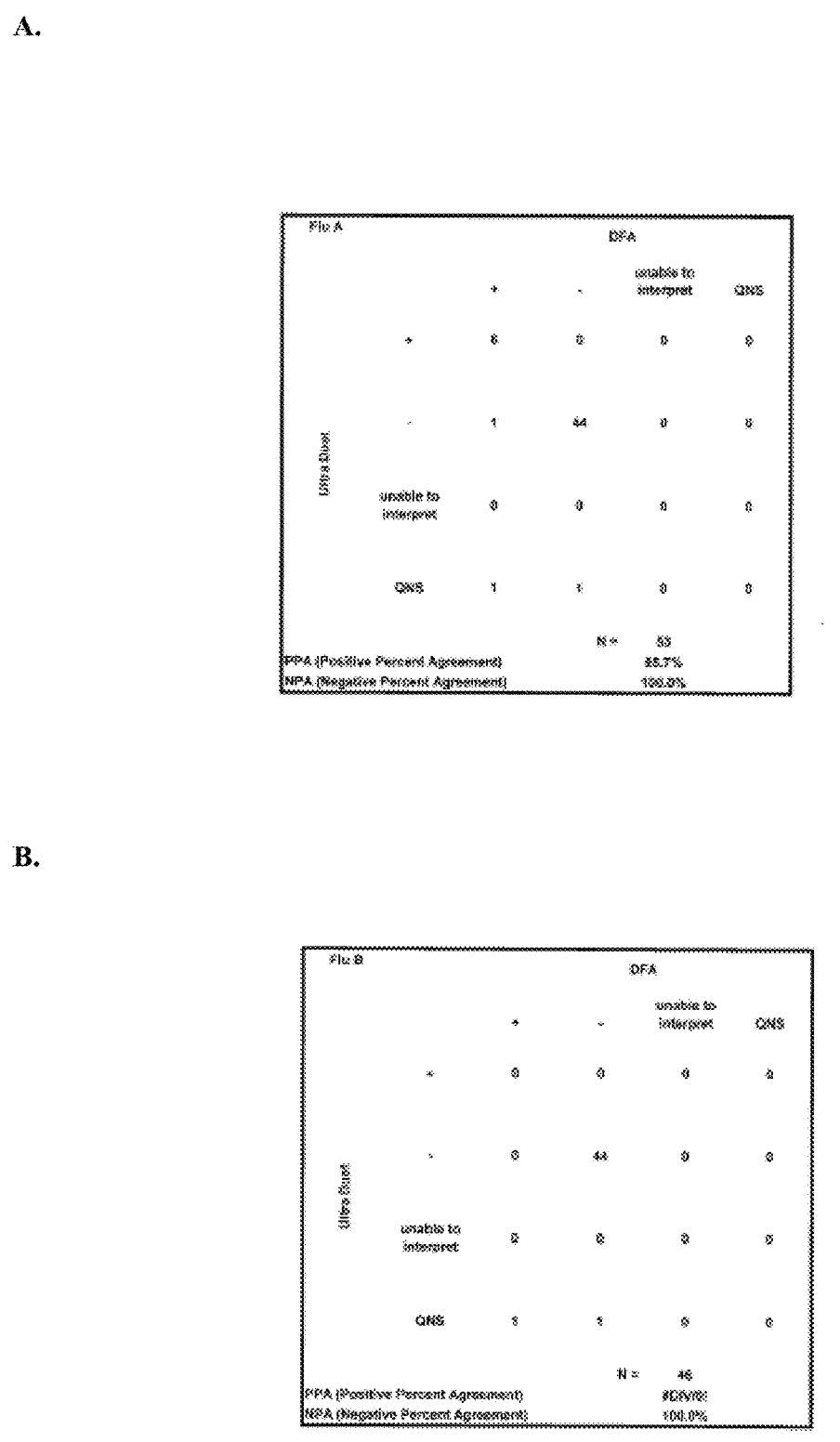
Figure 10:
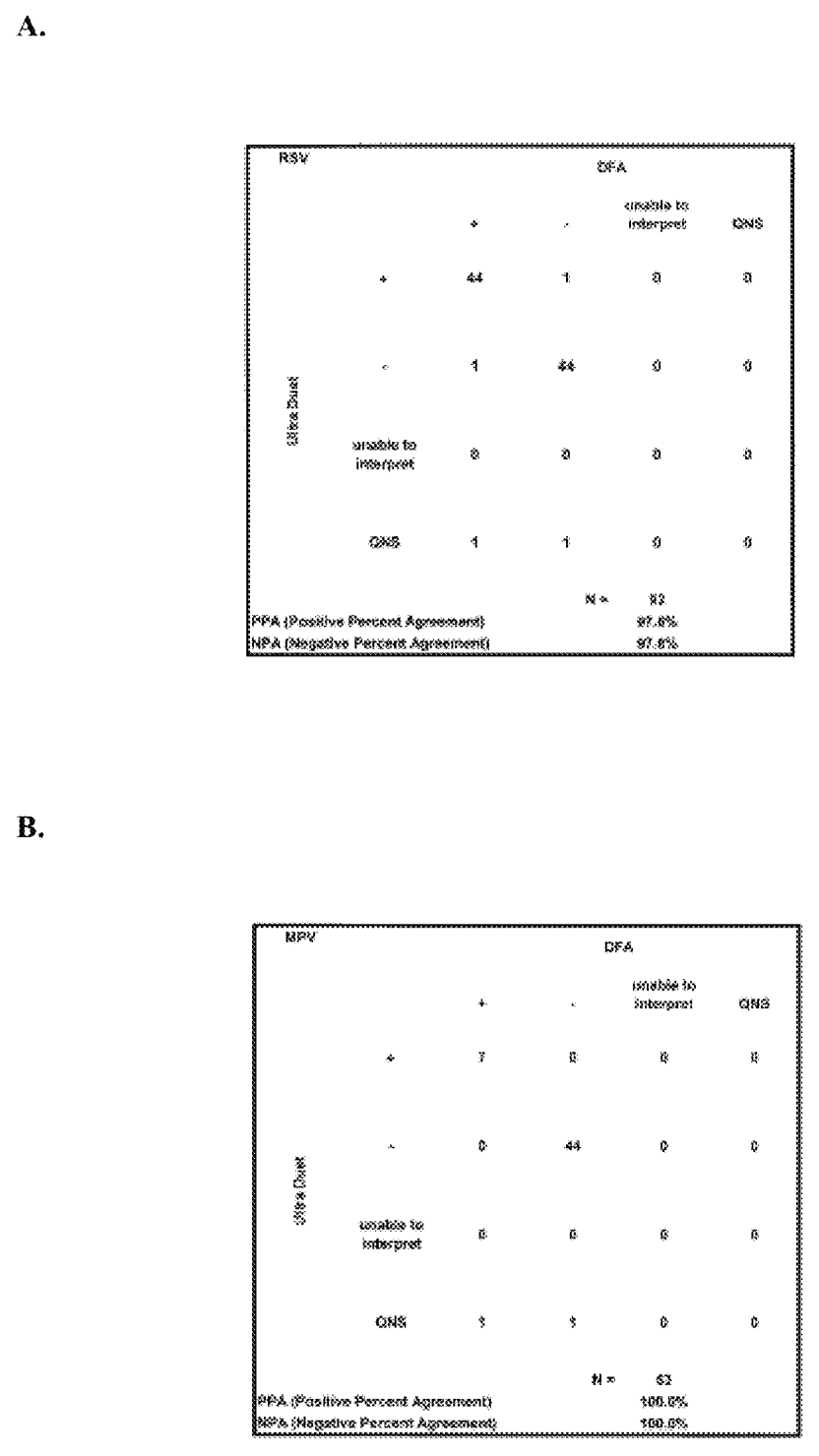
Figure 11:
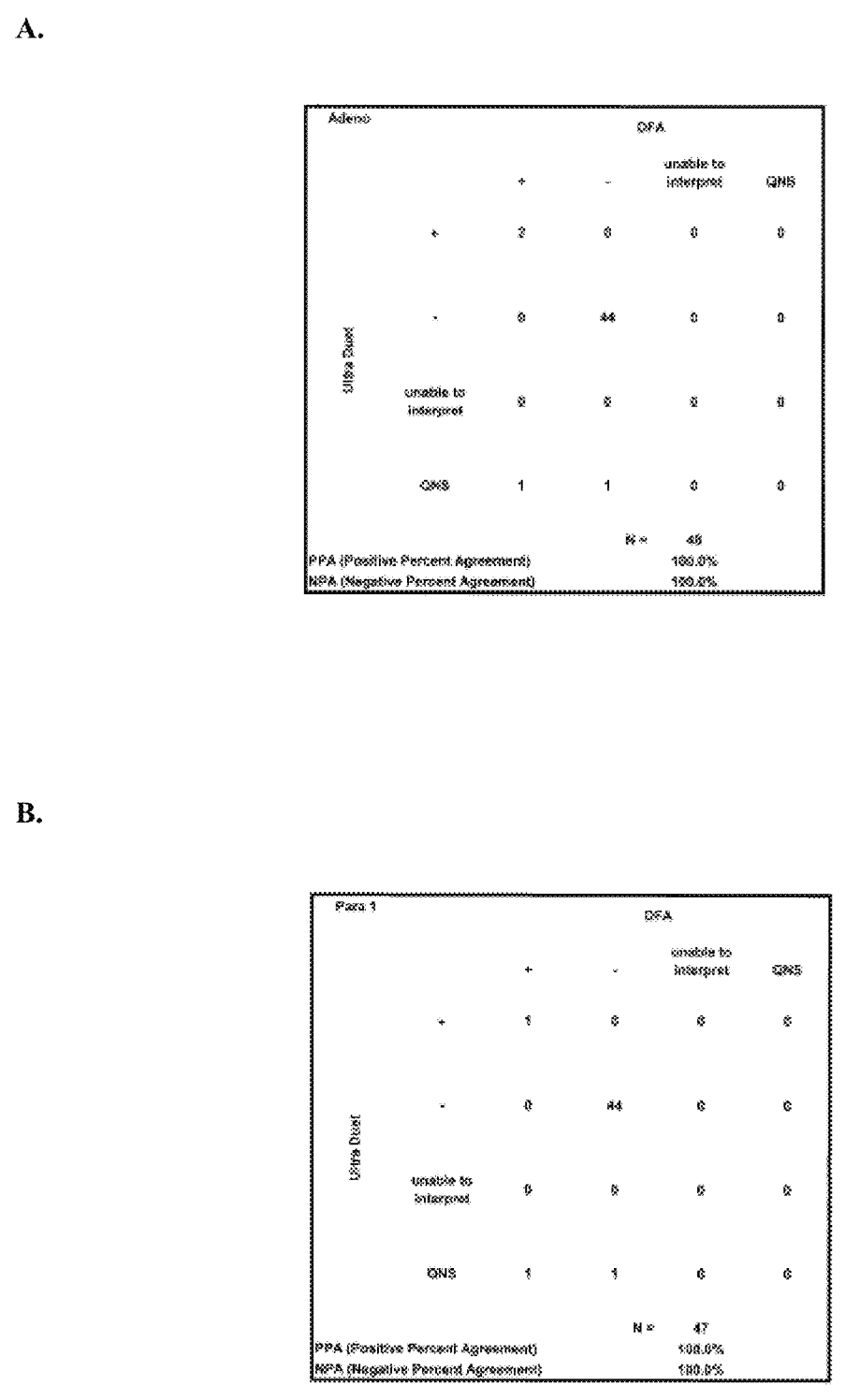
Figure 12:
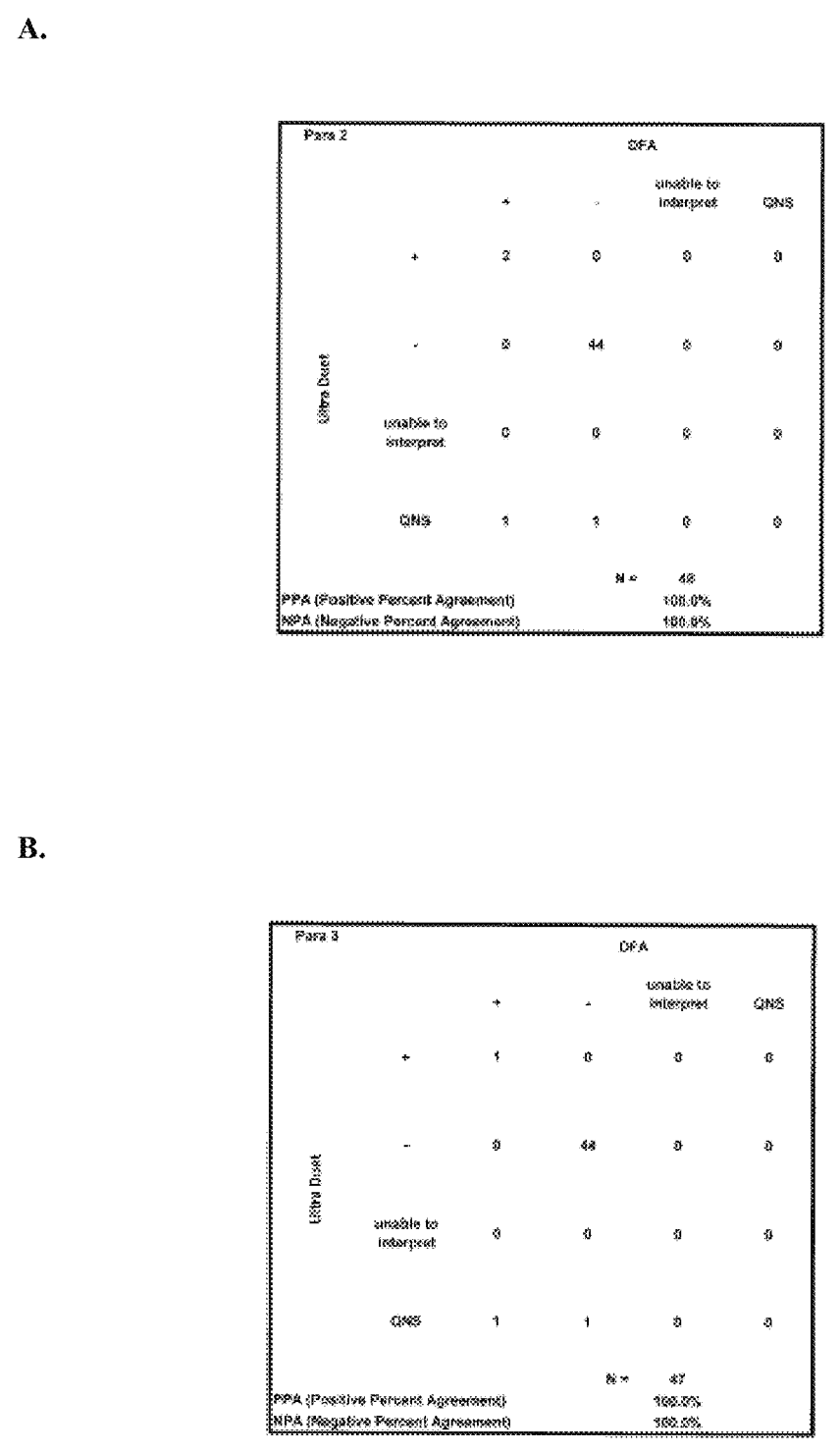
Figure 13:
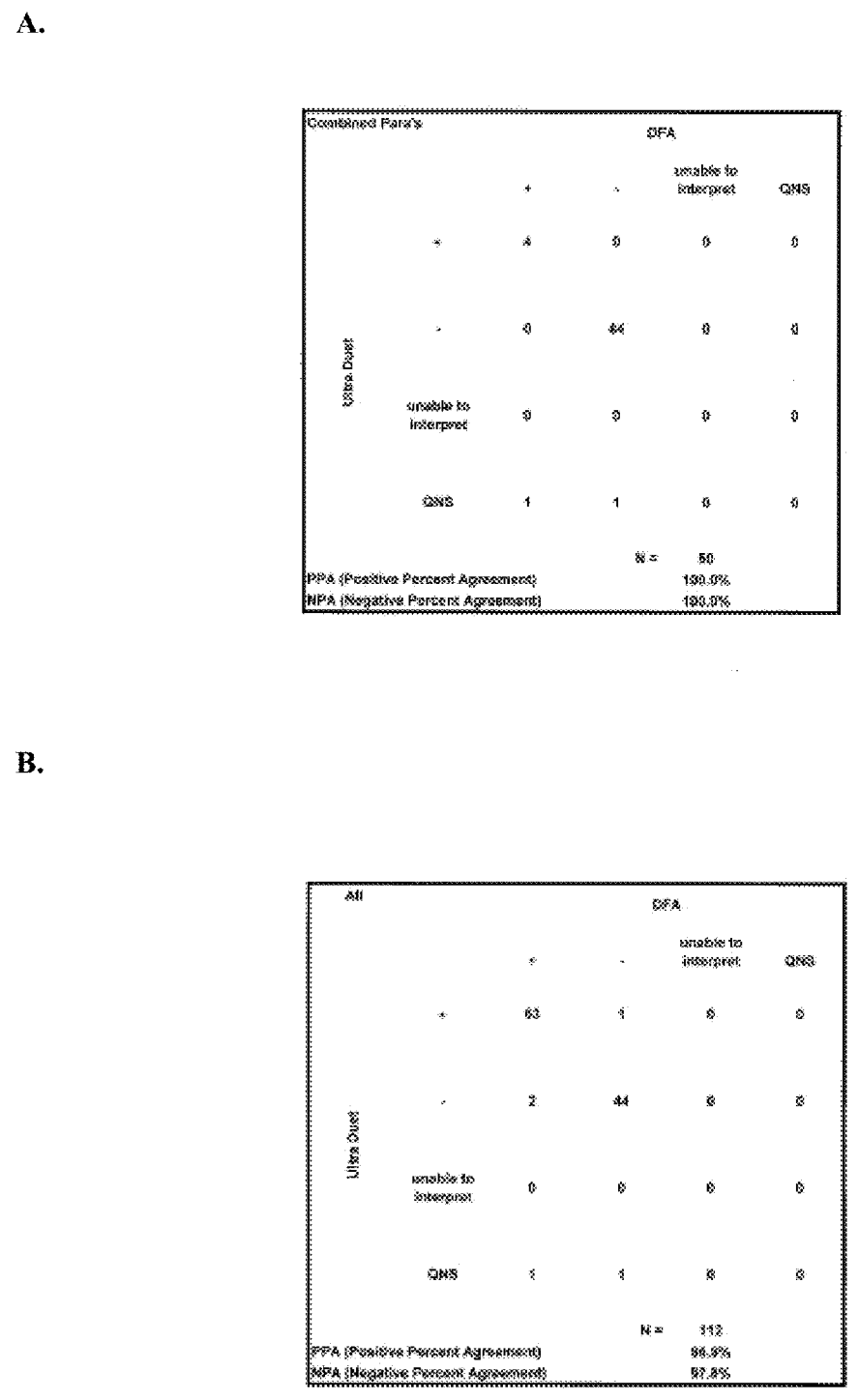

Studies have also demonstrated the specificity and selectivity of the LDFA versus a traditional DFA for: i) Influenza A (Flu A) MAb combination of clone 10B12C11 and clone A(6)B11 (FIG. 9A); ii) influenza B (Flu B) MAb combination of clone 8C7E11 and clone 9B4D9 (FIG. 9B); iii) respiratory syncytial virus (RSV) MAb combination of clone 3A4D9 and clone 4F9G3 (FIG. 10A); iv) metapneumovirus (MPV) MAb combination of clone #4, clone #23, and clone #28 (FIG. 10B); v) adenovirus (ADV) MAb combination of clone 8H2C9, clone 2H10E2, and clone 4H6C9 (FIG. 11A); vi) parainfluenza (PIV) virus 1 MAb combination of clone 1D8E10 and clone 9F61C9 (FIG. 11B); vii) parainfluenza virus 2 MAb combination of clone 2E4D7 and clone 5E4E11 (FIG. 12A); viii) parainfluenza virus 3 MAb combination of clone 4G5(1)E2H9 and clone 1F6C8 (FIG. 12B); ix) pooled parainfluenza 1-3 MAbs as described above (FIG. 13A); and x) combined mixture of i)-ix) (FIG. 13B).

In one embodiment, the present invention contemplates a method to perform LDFA comprising a virus-specific antibody. In one embodiment, the antibody comprises a monoclonal antibody. In one embodiment, the virus-specific monoclonal antibody comprises a fluorescent label. In one embodiment, the fluoresently labeled monoclonal antibody comprises Flu A monoclonal antibody (i.e., for example, with a PE label). In one embodiment, the fluorescently labeled monoclonal antibody comprises Flu B monoclonal antibody (i.e., for example, with a FITC label). In one embodiment, the fluorescently labeled monoclonal antibody comprises a RSV monoclonal antibody (i.e., for example, with a PE label). In one embodiment, the fluorescently labeled monoclonal antibody comprises MPV monoclonal antibody (i.e., for example, with a FITC label). In one embodiment, the fluorescently labeled monoclonal antibody comprises a parainfluenza (i.e., for example, PIV-1, -2 and -3) monoclonal antibody (i.e., for example, with a PE label). In one embodiment, the fluorescently labeled monoclonal antibody comprises an adenvirus monoclonal antibody (i.e., for example, with a FITC label).

In one embodiment, the present invention contemplates a method to detect at least eight (8) and identify at least five (5) viruses comprising incubating a single liquid sample with at least one PE-labeled monoclonal antibody directed to a first virus and at least one FITC-labeled monoclonal antibody is directed to a second virus. In one embodiment, a first aliquot of the liquid sample comprises a PE-labeled Flu A monoclonal antibody and a FITC-labeled Flu B monoclonal antibody. In one embodiment, a second aliquot of the liquid sample comprises a PE-labled RSV monoclonal antibody and a FITC-labeled MPV monoclonal antibody. In one embodiment, a third aliquot of the liquid sample comprises a PE-labeled PIV monoclonal antibody and a FITC-labeled adenovirus monoclonal antibody. The present method has considerable advantages over those DFAs currently available as this method can detect and identify at least eight (8) respiratory viruses using three (3) aliquots from a single biological sample.

a. Sapogenin Enhanced Methods

In one embodiment, the present invention contemplates a liquid direct fluorescence assay to detect virus that do not require incubation in either a fixative or a dehydration agent. These fixative and/or dehydration agents are required in DFAs because the virus-infected cells are adhered to a glass substrate to facilitate microscopic viewing and examiation. In one embodiment, the present method comprises unfixed cells, wherein the liquid does not contain fixatives or non-aqueous solvents (i.e, for example, alcohols, acetone, aldehydes, toluene, etc.). In one embodiment, the invention contemplates a LDFA wherein cells are permeabilized with a detergent agent. In one embodiment, the detergent comprises sapogenin. Although it is not necessary to understand the mechanism of an invention, it is believed that a detergent agent provides improved cell permeability of fluorescently labeled antibodies in comparison to conventional fixatives and dehydration agents. It is further believed that this improved fluorescently labeled antibody permeability results in greater binding with viral antigens, thereby resulting in improved signal strength. It is further believed that the improved signal strength provides equivalent sensitivity and improved accuracy for the present LDFA versus currently available DFAs for virus detection and identification.

Saponins, including sapogenin, have been reported as a lipid-based detergent. Sapogenin has been suggested as being able to enhance the contrast of cells and sub-cellular morphology in histological slide preparations. Such histology preparations typically use dehydration solvents (i.e., for example, toluene) but may employ fluorescent labels. Sapogenin was not used to facilitate the detection of viruses (i.e., for example, influenza). Farrell et al., "Biological Sample Processing Composition and Method," United States Patent Publication No. 2007/0172911 (herein incorporated by reference). Saponins have further been reported to permeabilize cell membranes. Saponin used in conjunction with Evan's blue and propidium iodide staining of influenza virus was not observed to detect the virus in a solution based assay. Johansen et al., "Compositions and Methods for Treatment of Viral Diseases," United States Patent Publication No. 2008/0161324 (herein incorporated by reference).

Saponins have detergent-like properties and have been reported useful as foaming agents. Further, saponins may be used as immunological adjuvants for viral vaccines including influenza and, when fluorescently labeled, is capable of detecting cell surface markers. Marciani et al., "Triterpene Saponin Analogs Having Adjuvant and Immunostimulatory Activity," U.S. Pat. No. 5,977,081 (1999); U.S. Pat. No. 6,262,029; and U.S. Pat. No. 6,080,725 (both herein incorporated by reference). Saponins may also be combined with nutraceuticals and/or pharmaceuticals. For example, saponins may suppress HIV replication. Dobbins et al., "Process For Isolating Saponins From Soybean-Derived Materials," U.S. Pat. No. 6,355,816 (2002) (herein incorporated by reference).

In one embodiment, the present invention contemplates a method to perform a liquid direct flourescent assay (LDFA) comprising sapogenin. Although it is not necessary to understand the mechanism of an invention, it is believed that sapogenin offers significant advantages over currently known DFA methods because the compound permeabilizes the cells instead of fixing the cells. It is further believed that permeabilization has the advantages of: i) treating the infected cells with a mild surfactant, thereby allowing the cells to maintain their three dimensional structure while being stained with a protein counterstain and labeled antibodies; ii) solubilizing the lipid portions of a cell membrane; and iii) allowing larger dye molecules and antibodies access to the cell's interior. In one embodiment, the present invention contemplates a method comprising LDFA, wherein sapogenein treatment improves virus detection and identification by decreasing background noise and improving antibody signal strength.

III. Portable Fluorescent Reader Devices

Fluorescence microscopy has allowed the examination of fluorescently stained specimens by visual inspection. However, automating fluorescently labeled cell counts in conjunction with total cell counts provides an opportunity for fast and reliable diagnostic information (i.e., for example, cytometers having internal alogrithms). In one embodiment, the present invention contemplates a device that generates data that compare favorably with those from a conventional hema-cytometer, yet it eliminates the variability associated with subjective interpretation. In one embodiment, the device is capable of displaying test results in less than one minute per sample. In one embodiment, the device further automatically calculates cell viability.

In one embodiment, the device may be used together with a plurality of staining agents. In one embodiment, the staining agents provide for testing a wide variety of nucleated cell lines, including, but not limited to, mammalian cells, hybridomas and ficoll preparations. In one embodiment, the staining agents are detected by a fluorescent microscopy-based imaging system that streamlines cell counting procedures. For example, the staining agents may include, but are not limited to, a plurality of fluorescently labeled monoclonal antibodies and nucleic acid dyes. In one embodiment, the nucleic acid dyes include but are not limited to, propidium iodide, acridine orange, or ethidium bromide.

In one embodiment, the device comprises an epi-illumination microscope where a charged couple device collected emitted fluorescence that results from illumination by light emitting diodes. In one embodiment, the device comprises a sample drawer configured to accept a sample tray comprising a plurality of samples (i.e., for example, a multi-well sample slide). In one embodiment, the illumination is accomplished by high intensity mercury-arc or quartz-halogen light emitting diodes. Following illumination and collection of the fluorescence, the cell count is generated by image analysis using an internal algorithm. In one embodiment, the device visually displays test results on a touch screen. In one embodiment, the device is capable of exporting the test results to an independent storage device (i.e., for example, a computer).

In one embodiment, the device is compatible a method comprising: a) pipeting a sample into at least one microwell of a multiwell microscope slide; b) loading the slide onto a slide tray; and c) inserting the slide tray into the sample drawer of the device. In one embodiment, the sample comprises a cell suspension and a plurality of staining reagents. Total cells (live and dead) may be counted by staining with, for example, by Thioflavin T, acridine orange, non-specific fluorescent dyes, or any particle attached to an antibody that is detectable by a microscope. Ethidium bromide is further added to identify the dead cells, wherein the number of live cells is then determined by subtraction.

Figure 14:
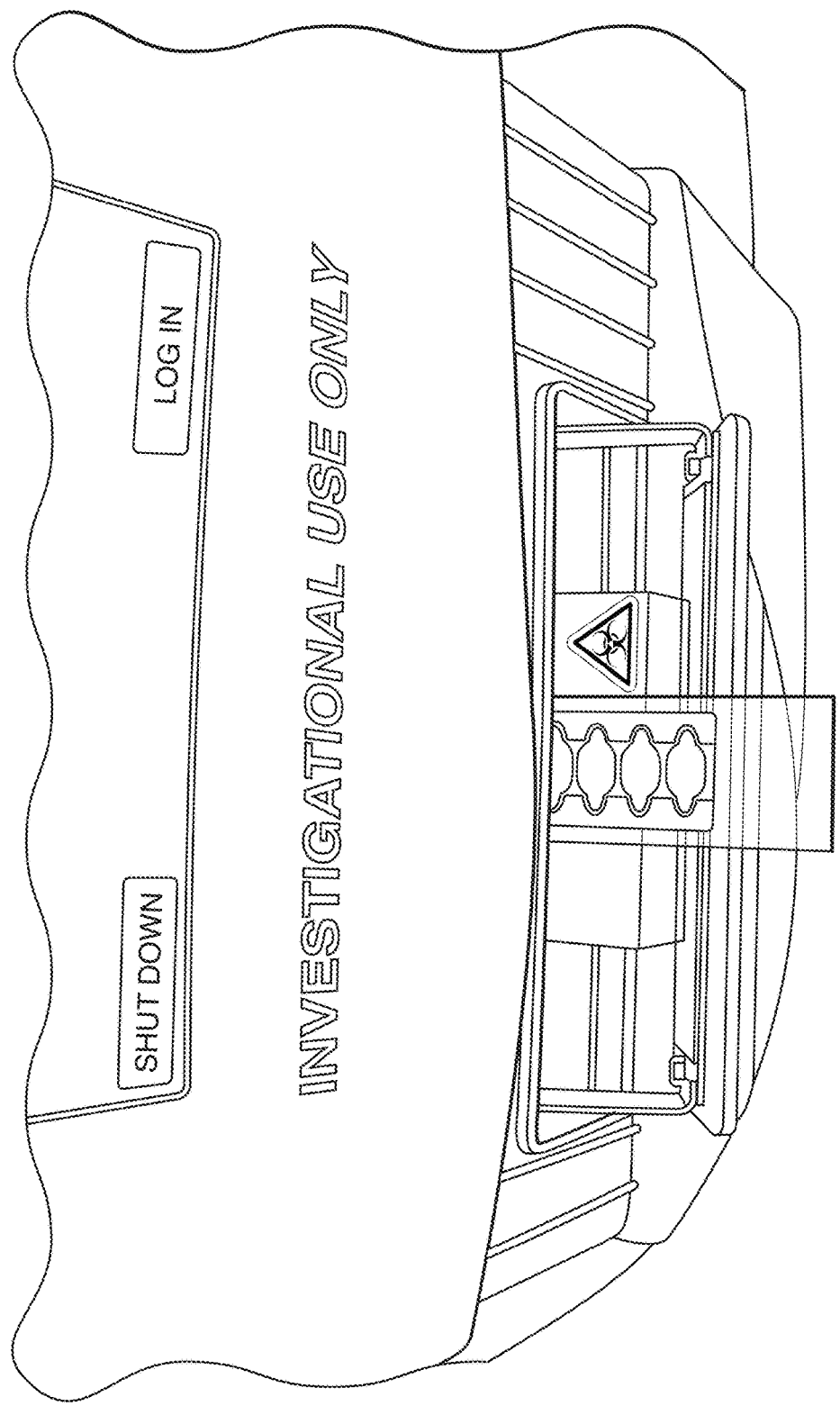
FIG. 14 presents one embodiment of a portable fluorescent reader capable of detecting and measuring emission illuminations from at least two differentially labeled MAbs. Also shown is a multi-well sample slide positioned for entry into the device on a slide tray that is inserted (as a unit) into a sample drawer.

While the present invention contemplates that many different devices that would be compatible with the presently contemplated method, preferred specifications may include, but are not limited to: i) sample volume of approximately 8 $\mu$l sample; ii) dynamic range: $5 \times 10^4$ to $1 \times 10^7$ cells/mL; iii) detectable cell diameter between approximately 8-40 microns; iv) calculation software that determines the labeled cell count and % viability by counting labled cells and total cells in the specified volume of the image fields; v) a fluorescence microscope having, for example, a charge coupled device camera; iv) two light emitting diodes (LEDs) @ 470 & 530 nm respectively; v) total analysis time in approximately 1 minute per test; vi) processing of six (6) images/test; vi) approximate dimensions: 37.5 H×25 D×30 W cm vii) approximate weight: 9 kg (20 lbs); vii) optimal operating temperature between approximately 10-35° C.; viii) optimal operating humidity between approximately 20-80% relative humidity; ix) optimal operating altitude of up to approximately 2,000 meters; and x) power requirements: 100-240 VAC, 50-60 Hz. See, FIG. 14.

Figure 15:
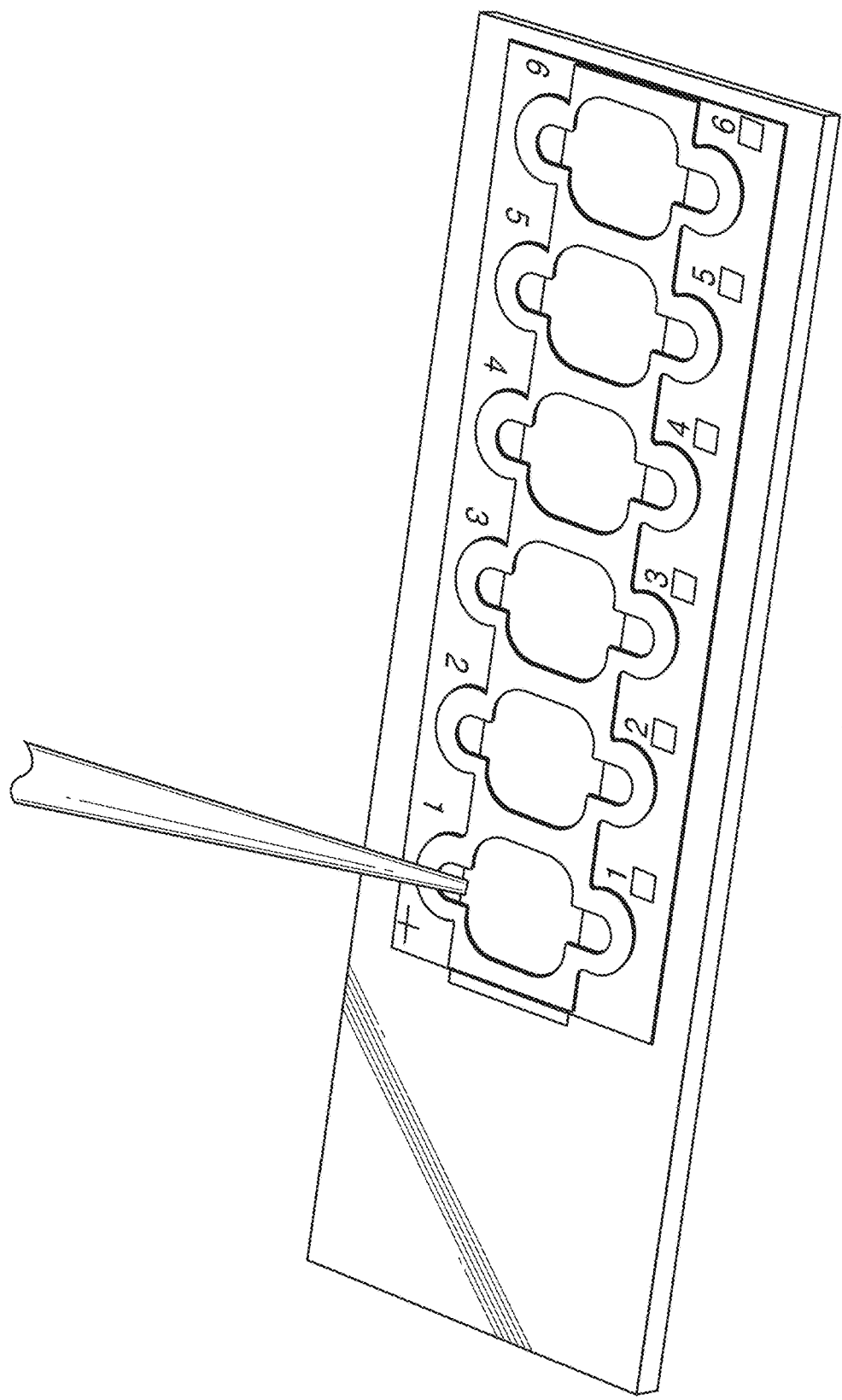
FIG. 15 presents one embodiment of a multi-well sample slide as shown with the device of FIG. 14. Pipet indicates location of entry and exit ports for the introduction and/or withdrawl of a liquid sample.

In one embodiment, the present invention contemplates a microscope slide comprising a plurality of sample wells (~200 $\mu$l). In one embodiment, the microwell comprises an inlet port. In one embodiment, the microwell comprises an outlet port. In one embodiment, the microwell comprises and inlet port and an outlet port. In one embodiment, the microwell is covered by a coverslip. In one embodiment, the ports are compatible with a 10 μl pipet tip. See, FIG. 15.

In one embodiment, the first, second, third, and fourth aliquots are idependently placed on a glass substrate. In one embodiment, the glass substrate comprises at least four (4) sample wells, such that each independent sample is placed within a separate microwell. In one embodiment, each microwell comprises a side inlet port and a side outlet port. In one embodiment, the microwell comprises a permanent cover.

IV. Integration of Device & Method

In one embodiment, the present invention contemplates a method comprising: a) providing; i) a fluorescent cytometer compatible with a sample container comprising a plurality of samples; ii) a biological specimen comprising a plurality of cells; b) labeling the cells with a plurality of fluorescent dyes; c) placing the labeled cells within the sample container; and d) examining the sample container for fluorescence using the cytometer.

In one embodiment, the present invention contemplates a device comprising a microprocessor comprising an algorithm capable of differentiating between a plurality of fluorescent signals. In one embodiment, a first fluorescent signal comprises a PE signal. In one embodiment, the PE signal appears as a golden-yellow fluorescent stain. In one embodiment, a second fluorescent signal comprises an FITC signal. In one embodiment, the FITC signal appears as an apple-green fluorescent stain. In one embodiment, a third fluorescent signal comprises a propidium iodide signal. In one embodiment, the propidium iodide signal appears as a red fluorescent stain.

In one embodiment, the rinsed and centrifuged liquid sample is loaded onto a sample container comprising a glass substrate. In one embodiment, the glass substrate comprises a plurality of independent samples. In one embodiment, the glass substrate is compatible with a device comprising an algorithm capable of detecting and evaluating a plurality of fluorescent signals. In one embodiment, the device detects the signals from each independent sample.

Although there are many different methods of preparing and examining cells, the following protocol is described in detail as but one example that is compatible with the presently disclosed invention. Briefly, the processing of the specimen for reading in the instrument is as follows. A nasopharengeal (NP) swab or aspirated NP specimen is placed in a transport medium (i.e., for example, phosphate buffered saline; PBS). An aliquot (~1 ml) is transferred to a centrifuge tube for pelleting. The cell pellet is resuspended in about 0.1 ml of PBS, vortexed to disperse the cells and then 25 uL of the suspension are transferred to 4 separate tubes, to which are added, respectively, 1 drop of fluorescein-labeled, Non-Immune mouse Ab, Flu A MAb, Flu B MAb and RSV MAb and allowed to stand at room temperature for 10 minutes. Optionally, each of these MAb solutions also contains sapogenin as a cell permeabilization reagent, propidium iodide to counterstain the nuclei of all the virus infected and uninfected NP cells. 1.5 ml of PBS is then added to each tube which is centrifuged and the supernatant of each (which contains the excess MAb, counterstain and permeabilization reagent) is decanted. Each cell pellet is resuspended in a minimal volume of PBS. The Non-Immune mouse Ab is included as a control since there are some specimens that contain cells that bind the Fc portion of murine antibodies. In such cases, all wells that contain fluorescein labeled MAb will show fluorescence and the state of infection of the specimen cannot be determined by this method. About 10 uL of each of the 4 suspensions are pipetted into each of 4 wells of a special slide in the order listed above; the 4 separate wells are covered by a coverslip and each well has an entry port on each side. Each well has a capacity of about 7 uL. The slide containing the cell suspensions is inserted into a slide tray of the cytometer device which automatically moves the slide inside the instrument where its alignment is first checked and then moved to successively position each well beneath a 5× objective. For example, the alignment may take approximately 95 sec. and each microwell may take approximately 2 minutes (i.e., a total of 8 minuntes for four successive microwell reads). The instrument may contain at least 2 LED's. A first LED emits light at a wavelength to excite fluorescein. A second LED that emits light to excite the propidium iodide counterstain. There are narrow band wavelength filters interposed between the emitted light and the CCD. At each well, a predetermined number of fields (9 or 16 out of a possible 27) is excited and imaged separately (first the fluorescein immediately followed by the propidium iodide) at both LED wavelengths which are captured by the CCD. The algorithm is then used to analyze the images, identifying specific virus-infected cells by virtue of size and the co-location of the fluorescein-labeled MAb and propidium iodide and non-infected cells by virtue of size and propidium iodide stain. The algorithm provides the number of infected cells and total number of cells in the fields and wells examined. Upon completion of reading the 4 wells, the slide is ejected from the instrument, ready for the next specimen-containing slide.

In one embodiment, the present invention contemplates detecting and identifying a virus using mixtures of publicly available MAbs. In one embodiment, each virus may be detected using at least one labeled MAb. See Table 9.

TABLE 9

Representative MAb Clones For Virus Identification

| Virus Specificity | Clonal Designation | Fluorescent Label | Source |
| --- | --- | --- | --- |
| Influenza A Virus | 2H3C5 A(6)B11 | PE | Diagnostic Hybrids, Inc. Athens, OH; Cat. No. 01-013102.v2 |
| Influenza B Virus | 8C7E11 9B4D9 | FITC | Diagnostic Hybrids, Inc. Athens, OH; Cat. No. 01-013202.v2 |
| Respiratory Syncytial Virus | 3A4D9 4F9G3 | PE | Diagnostic Hybrids, Inc Athens, OH; Cat. No. 01-013302.v2 |
| Metapneumovirus | Clone #4 C2C10 | FITC | US Patent Application Publication Number 2007/0248962, herein incorporated by reference |
| Metapneumovirus | Clone #23 C2D11 | FITC | US Patent Application Publication Number 2007/0248962, herein incorporated by reference |

TABLE 9-continued

Representative MAb Clones For Virus Identification

| Virus Specificity | Clonal Designation | Fluorescent Label | Source |
| --- | --- | --- | --- |
| Metapneumovirus | Clone #28<br>T3H11 | FITC | US Patent Application Publication Number 2007/0248962, herein incorporated by reference |
| Parainfluenza 1 Virus | 1D8E10<br>9F61C9 | PE | Diagnostic Hybrids, Inc Athens, OH; Cat. No. 01-013502.v2 |
| Parainfluenza 2 Virus | 2E4D7<br>5E4E11 | PE | Diagnostic Hybrids, Inc Athens, OH; Cat. No. 01-013602.v2 |
| Parainfluenza 3 Virus | 4G5(1)E2H9<br>1F6C8 | PE | Diagnostic Hybrids, Inc Athens, OH; Cat. No. 01-013702.v2 |
| Adenovirus | 8H2C9<br>2H10E2<br>4H6C9 | FITC | Diagnostic Hybrids, Inc. Athens, OH; Cat. No. 01-013402.v2 |

In one embodiment, an influenza A reagent comprises at least one PE-labeled MAb selected from the group comprising clone 2H3C5 or clone A(6)B11. In one embodiment, an influenza B reagent comprises at least one FITC-labeled MAb selected from the group comprising clone 8C7E11 or clone 9B4D9. In one embodiment, a respiratory syncytial virus reagent comprises at least one PE-labeled MAb selected from the group comprising clone 3A4D9 or clone 4F9G3. In one embodiment, a metapneumovirus reagent comprises at least one FITC-labeled MAb selected from the group comprising clone #4, clone #23, or clone #28. In one embodiment, a parainfluenza 1 reagent comprises at least one PE-labeled MAb selected from the group comprising clone 1D8E10 or clone 9F61C9. In one embodiment, a parainfluenza 2 reagent comprises at least one PE-labeled MAb selected from the group comprising clone 4G5(1) E2H9 or clone 1F6C8. In one embodiment, a parainfluenza 3 reagent comprises at least one PE-labeled MAb selected from the group comprising clone 4G5(1)E2H9 or clone 1F6C8. In one embodiment, an adenovirus reagent comprises at least one FITC-labeled MAb selected from the group comprising clone 8H2C9, clone 2H10E2, or clone 4H6C9.

Although there are many different methods of detecting and identifying viral infected cells, the following protocol is described in detail as but one example that is compatible with the presently disclosed invention. In one embodiment, a specimen prepared as described above is aliquoted into three (3) independent wells on a glass substrate (i.e., for example, a microscope slice). In one embodiment, the method further comprises contacting an influenza A reagent and an influenza B reagent with the sample in a first well. In one embodiment, the method further comprises contacting a respiratory syncytial virus reagent and a metapnuemovirus reagent with the sample in a second well. In one embodiment, a third well comprises a parainfluenza 1 reagent, a parainfluenza 2 reagent, a parainfluenza 3 reagent and an adenovirus reagent. In one embodiment, the method further comprises detecting influenza A in the first well upon appearance of a golden-yellow fluorescent stain. In one embodiment, the method further comprises detecting the absence of influenza A in the first well upon appearance of only a red stain. In one embodiment, the method further comprises detecting influenza B in the first well upon appearance of an apple-green fluorescent stain. In one embodiment, the method further comprisies detecting the absence of influenza B in the first well upon appearance of only a red stain. In one embodiment, the method further comprises detecting respiratory syncytial virus in the second well upon appearance of a golden-yellow fluorescent stain. In one embodiment, the method further compries detecting the absence of respiratory syncytial virus in the second well upon appearance of only a red stain. In one embodiment, the method further comprises detecting metapneumovirus in the second well upon appearance of an apple-green fluorescent stain. In one embodiment, the method further comprises detecting the absence of metapneumovirus in the second well upon appearance of only a red stain. In one embodiment, the method further comprises detecting at least one parainfluenza virus in the third well upon appearance of a golden-yellow fluorescent stain. In one embodiment, the at least one parainfluenza virus is selected from the group comprising parainfluenza 1, parainfluenza 2, or parainfluenza 3. In one embodiment, the method further comprises detecting the absence of any parainfluenza virus in the third well upon appearance of only a red stain. In one embodiment, the method further comprises detecting an adenovirus in the third well upon appearance of an apple-green fluorescent stain. In one embodiment, the method further comprises detecting the absence of an adenovirus in the third well upon appearance of only a red stain.

V. Antibodies

The present invention provides isolated antibodies (i.e., for example, polyclonal or monoclonal). In one embodiment, the present invention provides monoclonal antibodies that specifically bind to viral epitopes comprised of at least five amino acid residues or lipid residue. These antibodies find use in the detection methods described above.

An antibody against a viral epitope of the present invention may be any monoclonal or polyclonal antibody, as long as it can recognize the epitope. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Various methods may be used for screening for a hybridoma producing the antibody (e.g., against a viral epitope of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a viral epitope of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to a hapten in a weight ratio of about 0.1 parts to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a protein expressed resulting from a virus infection (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

The present invention may be practiced using any antibody. As described above, preferred antibodies comprise monoclonal antibodies that are produce from hybridoma cell cultures. In one embodiment, the present invention contemplates a hybridoma cell culture that produces a monoclonal antibody, wherein said monoclonal antibody has specific affinity for a viral antigen derived from a virus selected from the group including, but not limited to, influenza A, influenza B, adenovirus, parainfluenza 1, parainfluenza 2, parainfluenza 3, parainfluenza 4, respiratory syncytial virus, human metapneumovirus, varicella zoster virus, herpes simplex virus-1, herpes simplex virus-2, cytomegalovirus IE, coronavirus 229E, coronavirus 0C43, severe acute respiratory syndrome virus, coxsackie virus B3 VP1 Pan-EV, Poliovirus 1 VP1 Pan-EV, enterovirus 70 specific, enterovirus 71 specific, enterovirus 71/Coxsackie A16 bispecific, bocavirus, and human papilloma virus. In one embodiment, the present invention contemplates a hybridoma cell culture that produces a monoclonal antibody, wherein the monoclonal antibody has specific affinity for a bacterial antigen derived from a bacteria selected from the group including, but not limited to, *chlamydia*, methicillin resistant *Staphylococcus aureus*, Group A *Streptococcus*, and Group B *Streptococcus*. In one embodiment, the present invention contemplates a hybridoma cell culture that produces a monoclonal antibody, wherein the monoclonal antibody has specific affinity for a small organic molecule selected from the group including, but not limited to, nicotine or cotinine A. Influenza A/Respiratory Virus Monoclonal Antibodies In one embodiment, the present invention contemplates a specific monoclonal antibody capable of qualitatively detecting and identifying influenza A viral antigens. In one embodiment, the present invention contemplates a specific monoclonal antibody capable of screening for viral antigens selected from the group comprising influenza B virus antigens, respiratory syncytial virus antigens, adenovirus antigens, and parainfluenza virus types 1, 2, and 3 antigens. In one embodiment, the detecting and/or screening comprises directly testing cells derived from respiratory biological specimens. In one embodiment, the detecting and/or screening comprises a method performed in a cell culture by immunofluorescence using the monoclonal antibodies (MAbs).

In one embodiment, the MAbs are provided in a kit comprising a plurality of viral antigen-specific murine MAbs. In one embodiment, MAbs for influenza A virus are directly labeled with R-phycoerythrin (i.e., for example, emitting a golden-yellow fluorescence). In one embodiment, MAbs for influenza B virus, respiratory syncytial virus, adenovirus, and parainfluenza virus types 1, 2, and 3, are directly labeled with fluorescein isothiocyanate (i.e., for example, emitting an apple-green fluorescence). Although it is not necessary to understand the mechanism of an invention, it is believed that these MAbs result in the qualitative and quantitative detection of these viruses.

In one embodiment, the present invention contemplates a method comprising isolating cells derived from a clinical and/or biological specimen, or from a cell culture. In one embodiment, the cells are processed, stained and labeled. In one embodiment, the labeling results in a golden-yellow fluorescence from an Influenza A virus infected cell. In one embodiment, the labeling results in an apple-green fluorescence from an influenza B virus, respiratory syncytial virus, adenovirus, or parainfluenza virus types (1-3) infected cell.

1. Hybridoma Development

In one embodiment, the present invention contemplates a composition comprising an MAb 2H3C5. In one embodiment, the composition may further comprise an MAb 10B12C11. In one embodiment, the composition may further comprise an MAb A(6)B11. In one embodiment, the MAbs may be produced in mammalian hybridomas including, but not limited to, murine hybridomas. See, Table 10.

TABLE 10

Representative Hybridoma Clones For Influenza A/Respiratory Virus MAbs

| MAb Clone ID | Antigen for immunizations | Animal for immunizations | Target protein |
|---|---|---|---|
| Influenza A virus 2H3C5 | Influenza A virus (Texas 1/77, H3N2), purified from amniotic fluids | BALB/c mice | Unknown[1] |
| Influenza A virus A(6)B11 | Unknown, the hybridoma purchased from ZymeTx, Inc[2] | Unknown | Unknown[a] |

[1]Target protein denaturation by the sample process for Western blotting precludes the target protein identification.
[2]Oklahoma City, OK.
[a]As disclosed herein.

Although it is not necessary to understand the mechanism of an invention, it is believed that an MAbs having the highest antigen affinity would give the brightest fluorescent staining In one embodiment, the present invention contemplates a method comprising screening MAb producing hybridomas with high affinity MAbs using indirect fluorescent assay (IFA) on infected cell cultures. For example, influenza A viruses were inoculated onto R-Mix® (Diagnostic Hybrids, Inc., Athens, Ohio) cell monolayers in 96-well plates and grown for 24 hours at 35° to 37° C. The cells were then fixed with acetone, washed and incubated at 35° to 37° C. with hybridoma cell supernatant for 30 minutes in a humidified incubator. The cells were again washed and then incubated at 35° to 37° C. in a humidified incubator with FITC-labeled goat anti-mouse antibody for 30 minutes. The resulting stains were used to choose the best clones to take forward to the next step in the development process (i.e., for example, small scale purification and direct labeling).

Hybridomas that were screened and selected in this manner resulted in the identification of specific isotypes. For example, one immunogen that was used for mouse immunization was influenza A antigen (Texas 1/77, H3N2), purified from a commercially available amniotic fluid (R02302; Biodesign). See, Table 11.

TABLE 11

Influenza A Hybridoma Product Candidates

| Clone name | Fluorescence Intensity* | Isotype |
|---|---|---|
| A(6)B11 | ++++ | IgG2a (k) |
| 2H3C5 | ++++ | IgG2b (k) |
| 10B12C11 | +++++ | IgG1 (k) |

*Subjective observed fluorescence intensity: + = weak and ++++++ = brightest.

2. Monoclonal Antibody Purification

Hybridoma monoclonal antibodies as produced above were subsequently purified from cell culture supernatant by Protein G affinity using Fast Protein Liquid Chromatography (FPLC). MAb purity was checked by SDS-PAGE wherein an internal quality control standard ensured a minimum purity of at least 90%.

Figure 6:
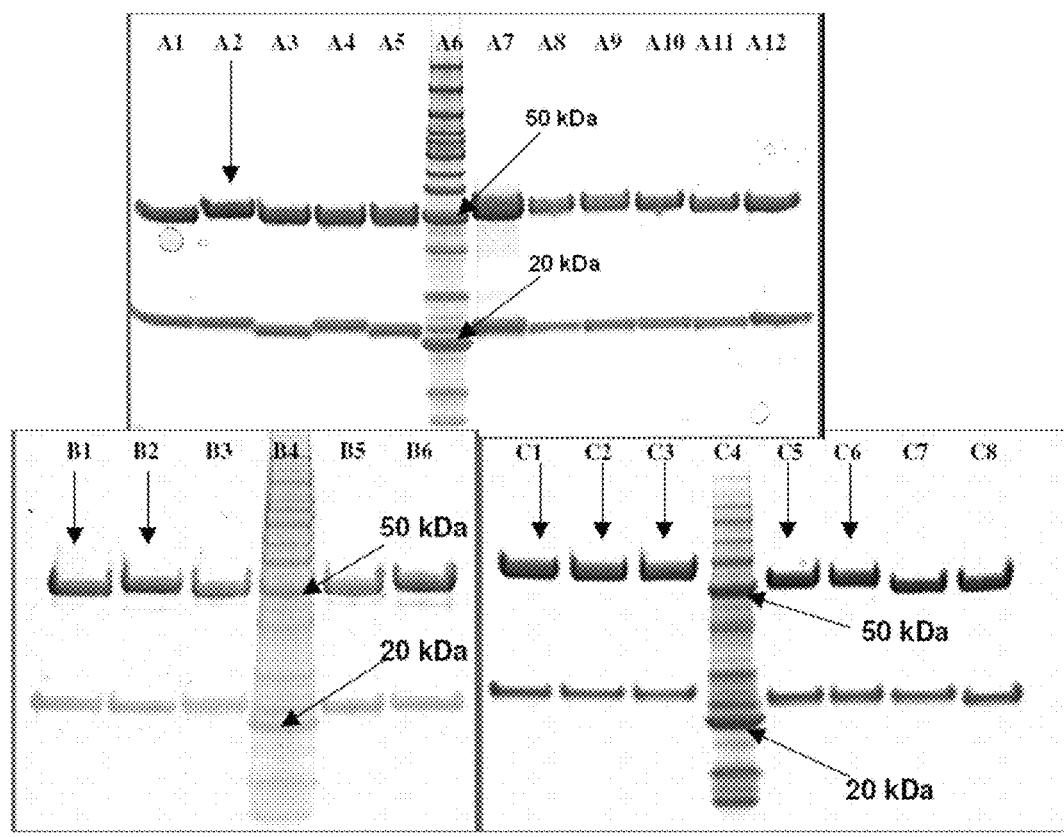
FIG. 6 shows exemplary data of an SDS-PAGE electropherogram isolation of influenza A virus MAbs. 0 MAb A(6)B11: lanes A2, C5, and C6; ii) MAb 10B12C11: lane B1; and iii) MAb 2H3C5: lanes C1, C2, and C3. Molecular weight markers are in lanes A6, B4, and C4; the 2 heavier marker bands represent 50 and 20 kDa. respectively. Other lanes are representative of other viral MAbs. Approximately 5-µg of protein were loaded onto each well.

The resultant purified MAbs were further isolated on a 4%→20% gradient SDS-PAGE electropherogram gel under denaturing conditions. FIG. 6. The purity of each of the MAbs was determined by scanning densitometry. See, Table 12.

TABLE 12

Purity Determination Of Representative mAbs.

| Antibody | Clone | Lot # | Lane Position | MAb Purity (%) |
|---|---|---|---|---|
| Influenza A virus | 2H3C5 | 031806 | C1 | 100 |
| | | 072506A | C2 | 99.9 |
| | | 072506B | C3 | 99.8 |
| Influenza A virus | A(6)B11 | 040506 | A2 | 99.8 |
| | | 080505-2FA | C5 | 100 |
| | | 082106A | C6 | 100 |

The data show that the purity of each representative MAb exceeded the minimal quality control 90% purity requirement, wherein the purity for all the MAbs ranges between approximately 99.7 to 100%.

3. Monoclonal Antibody Binding Affinities

The relative affinities of MAbs for various viral antigens were determined by ELISA assay as follows:

i) Lysates of a virus-infected cell (i.e., for example, influenza A (Texas/1/77 H3N2)) were obtained from Biodesign International were used to coat 96-well microtiter plates.
ii) Two-fold serial dilutions of the MAbs were incubated on each plate.
iii) The binding of each MAb to the immobilized viral antigen was detected by using a goat anti-mouse IgG antibody, conjugated to horseradish peroxidase (HRP).

Figure 7:
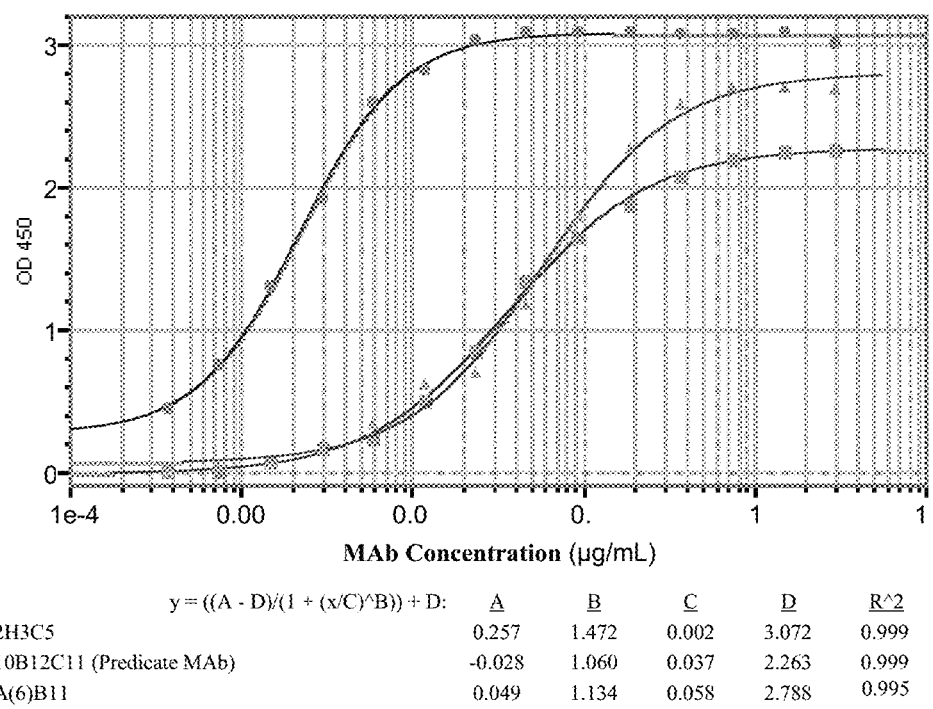
FIG. 7 presents exemplary data of binding affinities of various embodiments for Influenza A virus MAbs to Influenza A (Texas) virus. Red squares: MAb 10B12C11. Blue circles: MAb 2H3C5. Green triangles: MAb ZymeTx A(6)B11.

Results for an assay of: i) MAb (10B12C11); ii) MAbs 2H3C5 and; iii) MAb A(6)B11) to influenza A demonstrate binding affinities corresponding to kDa values of ~0.013 nM for 2H3C5, ~0.36 nM for 10B12C11, and ~0.96 nM for A(6)B11. The binding affinity for influenza A virus MAb 2H3C5 was 2-10 orders of magnitude higher than the 10B12C11 MAb and/or the A(6)B11 MAbs. FIG. 7. In one embodiment, the 2H3C5 MAb comprises a specific affinity for influenza A antigen.

Figure 8A:
FIGS. 8A-B present exemplary data showing detection of influenza A virus infected cells with a yellow-golden fluorescent monoclonal antibody (FIG. 8A) or an apple-green fluorescent monoclonal antibody (FIG. 8B).
Figure 8B:
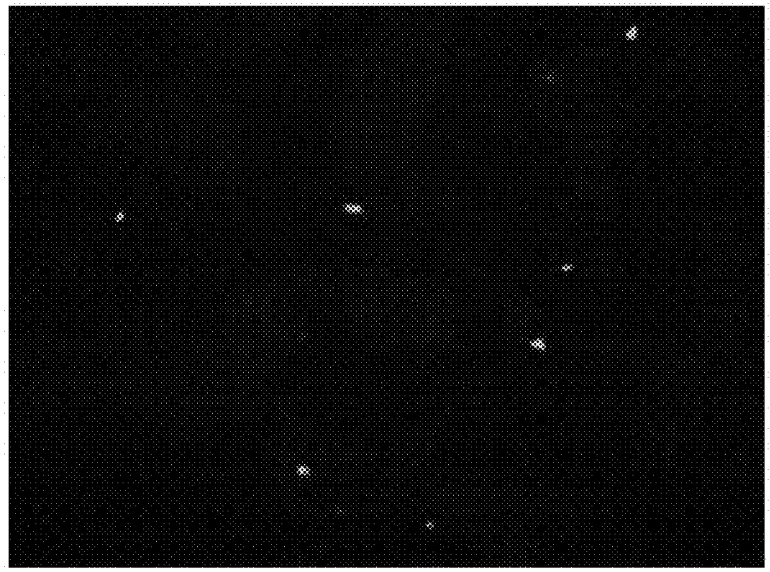

4. Monoclonal Antibody Characterization

A variety of methods were used to characterize influenza A virus MAbs in the present invention. See, Table 13.

TABLE 13

Characterization Assays for the Representative MAbs

| Virus Target | Clone | FPLC Purity | ELISA | Western blotting | In Situ Staining (lab strains) | In Situ Staining (clinical isolates) |
|---|---|---|---|---|---|---|
| Influenza A | 2H3C5 | Yes | Yes | Negative[3] | Positive | Positive |
| Influenza A | A(6)B11 | Yes | Yes | Negative | Positive | Positive |

[3]Negative result due to the epitope specimen treatment denaturing effects

The data show that 2H3C5 and A(6)B11 were both capable of detecting influenza A.

a. Analytical Sensitivity

Analytical sensitivity of representative MAbs were evaluated using influenza A virus. For example, strain Victoria (H3N2; ATCC VR-822) was used. In this determination, two 96-well cell culture plates were inoculated with the influenza A virus diluted to a level of 1.0 50% Tissue Culture Infectious Dose (1.0 $TCID_{50}$) per 0.2-mL inoculum. The plates were incubated at 35° to 37° C. for 24-hours and then stained. The assay was performed four times. An average of 35 positive wells (out of 96) detected with a combination of a MAb 2H3C5 and MAb A(6)B11. Likewise, an average of 35 positive wells (out of 96) was detected with a combination of MAb 10B12C11 and Mab A(6)B11. See, Table 14.

TABLE 14

Analytical Sensitivity of MAb Combinations To Influenza A Virus.

| Test Number | Positive wells | | Mean ± SD | |
|---|---|---|---|---|
| | 2H3C5/ A(6)B11 | 10B12C11/ A(6)B11 | 2H3C5/ A(6)B11 | 10B12C11/ A(6)B11 |
| 1 | 23 | 26 | 34.3 ± 12.0 | 34.8 ± 9.7 |
| 2 | 26 | 27 | | |
| 3 | 39 | 44 | | |
| 4 | 49 | 42 | | |

Paired t-test = 0.86

The data show that at 1.0 $TCID_{50}$, both MAb combinations positively identified influenza A virus infected cells.

b. Detection Limits

The analytical detection limits were determined for each MAb combination. Using the 2H3C5/A(6)B11 MAb combination as an example, the assay conditions were similar to those described above, with results reported in a different manner (numbers of fluorescent cells per cell monolayer). For example, influenza A virus (Victoria) stock virus preparation was diluted to a value of 359 $TCID_{50}$ per inoculum, and serial 2-fold dilutions were then made to a final calculated value of 0.7 $TCID_{50}$. Each dilution of virus was inoculated into six confluent monolayers of R-Mix® cells in shell vials, centrifuged at 700×g for 60 minutes and incubated at 35° to 37° C. for 48 hours.

The 2H3C5/A(6)B11 MAb combination or the 10B12C11/A(6)B11 MAb combination was used to stain 3 shell vials of each viral dilution of a 96-well plate. The determinations were performed in triplicate and the number of positive cells per well was counted. Fluorescent cells were counted on each coverslip at the indicated virus dilutions.

TABLE 15

Analytical Detection Limits of Representative MAbs for influenza A virus (Victoria).

| Influenza A virus (Victoria) | Fluorescent staining cells/cell monolayer (triplicate samplings) | |
|---|---|---|
| $TCID_{50}$ per inoculum | 2H3C5/A(6)B11 | 10B12C11/A(6)B11 |
| 5.60 | 2, 1, 0 | 3, 1, 0 |
| 2.80 | 1, 0, 2 | 1, 0, 1 |
| 1.40 | 0, 1, 2 | 0, 0, 1 |
| 0.70 | 0, 0, 0 | 0, 0, 0 |

The data show that both fluorescent antibody stain combinations performed to comparable limits, with a minimum viral dilution detected between 1.4 and 0.7 $TCID_{50}$.

5. Performance of Viral Monoclonal Antibodies

In one embodiment, the present invention contemplates a viral monoclonal antibody labeled with a fluorescent moiety including, but not limited to, FITC or R-PE. In one embodiment, a fluorescein-labeled MAb exhibits a fluorescent apple-green color. In one embodiment, a phycoerythrin-labeled MAb exhibits a fluorescent golden-yellow color. Although it is not necessary to understand the mechanism of an invention, it is believed that when viewed through a microscope fitted with standard FITC filters; both fluorescent colors may be visualized using the same FITC-filter set on a fluorescence microscope.

In one embodiment, a first MAb having specificity for influenza A virus is labeled with R-PE (golden-yellow) and a second MAb having specificity for influenza B virus, respiratory syncytial virus, adenovirus, parainfluenza viruses types 1, 2, and 3 is labeled with FITC (apple-green). In one embodiment, the present invention contemplates a first DFA kit capable of differentiating between influenza A virus and respiratory virus, wherein cells infected by the influenza A virus stain golden-yellow. FIG. 8A. In one embodiment, the present invention contemplates a second DFA kit capable of differentiating between a influenza A virus focus and respiratory virus focus, wherein cells infected by the influenza virus stain apple-green FIG. 8B. In TABLE 16-continued Viral Cross Reactivity and Specificity Testing

| Organism | Strain or Type | Lot Number | Labeled 2H3C5/A(6)B11MAb Combination | | $TCID_{50}$/Source/ or CFU |
|---|---|---|---|---|---|
| Adenovirus | Type 18, VR-19 | 011702A | − | + | 1,400 |
| Adenovirus | Type 31, VR-1109 | 011702B | − | + | 1,400 |
| Adenovirus | Type 40, VR-931 | 012802 | − | + | 1,400 |
| Adenovirus | Type 41, VR-930 | 012802A | − | + | 1,400 |
| Influenza A | Aichi, VR-547 (H3N2) | 061704O | + | − | 1,400 |
| Influenza A | Mal, VR-98 (H1N1) | 061704D | + | − | 1,400 |
| Influenza A | Hong Kong, VR-544 (H3N2) | 040104 | + | − | 1,400 |
| Influenza A | Denver, VR-546 (H1N1) | 061704P | + | − | 1,400 |
| Influenza A | Port Chalmers, VR-810 (H3N2) | 061704C | + | − | 1,400 |
| Influenza A | Victoria, VR-822 (H3N2) | 080204 | + | − | 1,400 |
| Influenza A | New Jersey, VR-897 (H1N1) | 110404 | + | − | 1,400 |
| Influenza A | WS, VR-1520 (H1N1) | 061704B | + | − | 1,400 |
| Influenza A | PR, VR-95 (H1N1) | 061704Q | + | − | 1,400 |
| Influenza B | Hong Kong, VR-823 | 093004B | − | + | 1,400 |
| Influenza B | Maryland, VR-296 | 041105 | − | + | 1,400 |
| Influenza B | Mass, VR-523 | 093004A | − | + | 1,400 |
| Influenza B | GL, VR-103 | 061704F | − | + | 1,400 |
| Influenza B | Taiwan, VR-295 | 061704E | − | + | 1,400 |
| Influenza B | JH-001 Isolate | 061704R | − | + | 1,400 |
| Influenza B | Russia, VR-790 | 041105 | − | + | 1,400 |
| RSV | Long, VR-26 Group A | 042204L | − | + | 1,400 |
| RSV | Wash, VR-1401 Group B | 042204W | − | + | 1,400 |
| RSV | 9320, VR-955 Group B | 061704I | − | + | 1,400 |
| Parainfluenza 1 | C-35, VR-94 | 061704L | − | + | 1,400 |
| Parainfluenza 2 | Greer, VR-92 | 061704M | − | + | 1,400 |
| Parainfluenza 3 | C 243, VR-93 | 061704N | − | + | 1,400 |
| Parainfluenza 4a | M-25, VR-1378 | 112701U | − | | 1,400 |
| Parainfluenza 4b | CH19503, VR-377 | 112701V | − | | 1,400 |
| Metapneumovirus | Subgroup A1 | 110905 | − | | 1,400 |
| Metapneumovirus | Subgroup A2 | 110805 | − | | 1,400 |
| Metapneumovirus | Subgroup B1 | 111105 | − | | 1,400 |
| Metapneumovirus | Subgroup B2 | 110405 | − | | 1,400 |
| Coronavirus | OC43, VR-1558 | 041204A | − | | 1,400 |
| Coronavirus | 229E, VR-740 | 121903 | − | | 1,400 |
| HSV-1 | 1F, VR-733 | 052405 | − | | 71 |
| HSV-1 | MacIntyre, VR-539 | 071005 | − | | 71 |
| HSV 2 | MS, VR-540 | 112701Y | − | | 71 |
| HSV 2 | Strain G, VR-734 | 052605 | − | | 71 |
| CMV | Towne, VR-977 | 011503 | − | | 430 |
| CMV | Davis, VR-807 | 062005 | − | | 430 |
| CMV | AD169, VR-538 | 052705 | − | | 430 |
| Varicella-zoster | Webster, VR-916 | 040504 | − | | 430 |
| Varicella-zoster | Ellen, VR-1367 | 050903 | − | | 430 |
| Echovirus | 4, Bion | QEC-0008 | − | | Control slide |
| Echovirus | 6, Bion | QEC-0008 | − | | Control slide |
| Echovirus | 9, Bion | QEC-0008 | − | | Control slide |
| Echovirus | 11, Bion | QEC-0008 | − | | Control slide |
| Echovirus | 30, Bion | QEC-0008 | − | | Control slide |
| Echovirus | 34, Bion | QEC-0008 | − | | Control slide |
| Coxsackievirus | B1, Bion | QCB-0011 | − | | Control slide |
| Coxsackievirus | B2, Bion | QCB-0011 | − | | Control slide |
| Coxsackievirus | B3, Bion | QCB-0011 | − | | Control slide |
| Coxsackievirus | B4, Bion | QCB-0011 | − | | Control slide |
| Coxsackievirus | B5, Bion | QCB-0011 | − | | Control slide |
| Coxsackievirus | B6, Bion | QCB-0011 | − | | Control slide |
| Mumps | Bion (CDC V5-004) | QMU-0308 | − | | Control slide |
| Rubeola (Measles) | Bion | QME-0424 | − | | Control slide |
| Rhinovirus 39 | 209 Picornavirus, VR-340 | 112701EE | − | | 1,400 |
| Bacteria | *Acholeplasma laidlawi* | 031404 | − | | ~1.0 × 10⁷ CFU |
| Bacteria | *Acinetobacter calcoaceticus* | 934332 | − | | 9.7 × 10⁵ CFU |
| Bacteria | *Bordetella bronchiseptica* | 031404 | − | | 1.8 × 10⁵ CFU |
| Bacteria | *Bordetella pertussis* | 031404 | − | | 4.7 × 10⁶ CFU |
| Bacteria | *Corynebacterium diphtheriae* | 031404 | − | | 2.5 × 10⁶ CFU |
| Bacteria | *Escherichia coli* | 335472 | − | | 2.6 × 10⁵ CFU |
| Bacteria | *Gardnerella vaginalis* | 3457511 | − | | 5.0 × 10⁵ CFU |
| Bacteria | *Haemophilis influenzae* type A | 031404 | − | | 9.3 × 10⁵ CFU |
| Bacteria | *Klebsiella pneumoniae* | 031404 | − | | 6.4 × 10⁶ CFU |
| Bacteria | *Legionella pneumophila* | 031404 | − | | 6.5 × 10⁴ CFU |
| Bacteria | *Moraxella cartarrhalis* | 031404 | − | | 6.4 × 10⁴ CFU |
| Bacteria | *Mycoplasma hominis* | 031404 | − | | ~1.0 × 10⁴ CFU |
| Bacteria | *Mycoplasma orale* | 031404 | − | | ~1.0 × 10⁴ CFU |
| Bacteria | *Mycoplasma pneumoniae* | 031404 | − | | ~1.0 × 10⁴ CFU |
| Bacteria | *Mycoplasma salivarium* | 031404 | − | | ~1.0 × 10⁷ CFU |
| Bacteria | *Neisseria gonorrhoeae* | 060805 | − | | 1.3 × 10⁶ CFU |
| Bacteria | *Proteus mirabilis* | 440498 | − | | 2.1 × 10⁶ CFU |

TABLE 16-continued

Viral Cross Reactivity and Specificity Testing

| Organism | Strain or Type | Lot Number | Labeled 2H3C5/A(6)B11MAb Combination | $TCID_{50}$/Source/ or CFU |
|---|---|---|---|---|
| Bacteria | Pseudomonas aeruginosa | 031404 | − | $1.0 \times 10^7$ CFU |
| Bacteria | Salmonella enteriditis | 3457511 | − | $2.5 \times 10^6$ CFU |
| Bacteria | Salmonella typhimurium | 363162 | − | $1.8 \times 10^6$ CFU |
| Bacteria | Staphylococcus aureus | 081100 | + | $1.0 \times 10^7$ CFU |
| Bacteria | Streptococcus agalactiae | 370784 | − | $9.6 \times 10^6$ CFU |
| Bacteria | Streptococcus pneumoniae | 031404 | − | $8.0 \times 10^5$ CFU |
| Bacteria | Streptococcus pyogenes | 031404 | − | $2.9 \times 10^7$ CFU |
| Bacteria | Ureaplasma urealyticum | 031404 | − | $\sim 1.0 \times 10^4$ CFU |
| Chlamydia sp. | Chlamydophila pneumoniae | CP-0176 | − | Control slide |
| Chlamydia sp. | Chlamydophila psittaci | FP-12-050218 | − | Control slide |
| Chlamydia sp. | Chlamydia trachomatis | 052705 | − | Control slide |
| Yeast | Candida glabrata | 992206 | − | $8.7 \times 10^6$ CFU |
| Protozoa | Trichomonas vaginalis | 410721 | − | Control slide |

The 2H3C5/A(6)B11 MAb combination was found to be reactive with viral target-specific infected cells. Reactivity with *Staphylococcus aureus* is most probably due to specific binding of the MAbs by the Protein A produced by *Staphylococcus aureus*. No reactivity was noted for all other microorganisms tested or for uninfected cells, as evidenced by no positive fluorescent cells or elevated background fluorescence.

Staining of *Staphylococcus aureus* appear as small points of fluorescence while all other cultures were negative. Although it is not necessary to understand the mechanism of an invention, it is believed that Protein A produced by *S. aureus* may bind the Fc portion of some fluorescein-labeled monoclonal antibodies. It is further believed that such binding can be distinguished from viral antigen binding on the basis of morphology (i.e. for example, *S. aureus*-bound fluorescence appears as small (~1 micron diameter), bright dots). Consequently, false positives may be present in cell cultures with bacterial contamination.

The plates inoculated for the bacteria CFU confirmation yielded the following results. The information is presented as CFU per mL and 0.01-mL is used to dot each slide well that the reagent is tested. The results for the commercially tested slides as well as the *mycoplasma* testing is listed and summarized. Table 17.

TABLE 17

Microorganism Cross-Reactivity And Specificity Testing

| Bacteria | Colonies Counted | Dilution Counted | CFU/ mL | CFU/ well |
|---|---|---|---|---|
| Bordetella bronchiseptica | 175 | $10^{-5}$ | 1.75e7 | 1.75e5 |
| Bordetella pertussis | 465 | $10^{-6}$ | 4.65e8 | 4.65e6 |
| Legionella pneumophila | 65 | $10^{-5}$ | 6.50e6 | 6.50e4 |
| Corynebacterium diphtheriae | 250 | $10^{-6}$ | 2.50e8 | 2.50e6 |
| Klebsiella pneumoniae | 64 | $10^{-7}$ | 6.40e8 | 6.40e6 |
| Streptococcus agalactiae | 96 | $10^{-7}$ | 9.60e8 | 9.60e6 |
| Haemophilis influenzae type A | 93 | $10^{-6}$ | 9.30e7 | 9.30e5 |
| Pseudomonas aeruginosa | 100 | $10^{-7}$ | 1.00e9 | 1.00e7 |
| Streptococcus pneumoniae | 80 | $10^{-6}$ | 8.00e7 | 8.00e5 |
| Streptococcus pyogenes | 293 | $10^{-7}$ | 2.93e9 | 2.93e7 |
| Moraxella cartarrhalis | 64 | $10^{-5}$ | 6.40e6 | 6.40e4 |
| Staphylococcus aureus | 104 | $10^{-7}$ | 1.04e9 | 1.04e7 |
| Neisseria gonorrhoeae | 133 | $10^{-6}$ | 1.33e8 | 1.33e6 |
| Proteus mirabilis | 212 | $10^{-6}$ | 2.12e8 | 2.12e6 |
| Acinetobacter calcoaceticus | 97 | $10^{-6}$ | 9.70e7 | 9.70e5 |
| Escherichia coli | 26 | $10^{-6}$ | 2.6e7 | 2.60e5 |
| Gardnerella vaginalis | 50 | $10^{-6}$ | 5.00e7 | 5.00e5 |
| Salmonella enteriditis | 250 | $10^{-6}$ | 2.50e8 | 2.50e6 |
| Salmonella typhimurium | 177 | $10^{-6}$ | 1.77e8 | 1.77e6 |
| Candida glabrata | 87 | $10^{-7}$ | 8.70e8 | 8.7e6 |
| | Last Dilution with Visible Colonies | | | |
| Mycoplasma hominis | | $10^{-6}$ | | |
| Mycoplasma orale | | $10^{-6}$ | | |
| Mycoplasma pneumoniae | | $10^{-6}$ | | |
| Mycoplasma salivarium | | $10^{-9}$ | | |
| Ureaplasma urealyticum | | $10^{-6}$ | | |
| Acholeplasma laidlawii | | $10^{-9}$ | | |
| Chlamydia trachomatis | All tested on commercially available antigen control slides | | | |
| Chlamydia psittaci | | | | |
| Trichomonas vaginalis | | | | |
| Chlamydia pneumoniae | | | | |

For each of the bacteria tested, there was no fluorescence observed at 200 or 400× magnification with the subject reagent. The *Staphylococcus aureus* exhibits some slight fluorescence but that is expected due to Protein A binding of the MAb.

7. Stability Studies

The shelf life of the 2H3C5/A(6)B11MAb combination has been established as at least 12 months. Stability studies are conducted by storing the MAb combination at a temperature ranging between approximately 2° to 8° C. Various virus-infected R-Mix® cells cultured with human respiratory viruses: Table 18.

TABLE 18

Virus strains used for Stability Studies

| Virus | Source | Other Identification |
|---|---|---|
| Influenza A | ATCC VR-822 | Victoria (H3N2) |
| Influenza B | ATCC VR-295 | Taiwan/2/62 |
| Respiratory Syncytial Virus | ATCC VR-1401 | RSV-B, Wash |
| Adenovirus Type 1 | ATCC VR-1 | |
| Adenovirus Type 14 | ATCC VR-15 | |
| Parainfluenza 1 | ATCC VR-94 | C-35 |
| Parainfluenza 2 | ATCC VR-92 | Greer |
| Parainfluenza 3 | ATCC VR-93 | C-243 |

Performance testing occurred at various time intervals during storage wherein characteristics were monitored including, but not limited to, performance, pH, color, and clarity. Each assay was run with dilution series of each of the MAb Conjugates at "neat" and a 1/16 dilution, then 1/2 dilutions to as far as 1/256. Acceptance criterion is "bright fluorescence" observed in fixed, stained, infected cells using at least a 1/16 dilution. See, Table 19.

TABLE 19

Stability Test Results For 2H3C5/A(6)B11MAb Combination

| Lot number | Manufacture date | Date tested | Maximum Acceptable Dilution | Result | Time elapsed |
|---|---|---|---|---|---|
| 0915065A | Sep. 15, 2006 | Sep. 19, 2006 | 1/256 | Pass | 0-months |
| 1127065A | Nov. 27, 2006 | Nov. 20, 2006 | 1/256 | Pass | |
| 0523075A | May 23, 2007 | Aug. 13, 2007 | 1/256 | Pass | |
| 0915065A | Sep. 15, 2006 | Dec. 19, 2006 | 1/256 | Pass | 3-months |
| 1127065A | Nov. 27, 2006 | Mar. 19, 2007 | 1/256 | Pass | |
| 0523075A | May 23, 2007 | Aug. 23, 2007 | 1/256 | Pass | |
| 0915065A | Sep. 15, 2006 | Mar. 15, 2007 | 1/256 | Pass | 6-months |
| 1127065A | Nov. 27, 2006 | Jun. 05, 2008 | 1/256 | Pass | |
| 0523075A | May 23, 2007 | Mar. 05, 2008 | 1/256 | Pass | |
| 0915065A | Sep. 15, 2006 | Jun. 20, 2007 | 1/256 | Pass | 9-months |
| 1127065A | Nov. 27, 2006 | Aug. 28, 2007 | 1/256 | Pass | |
| 0523075A | May 23, 2007 | Mar. 05, 2008 | 1/256 | Pass | |
| 0915065A | Sep. 15, 2006 | Sep. 18, 2007 | 1/256 | Pass | 12-months |
| 1127065A | Nov. 27, 2006 | Dec. 04, 2007 | 1/256 | Pass | |
| 0523075A | May 23, 2007 | May 20, 2008 | 1/256 | Pass | |
| 0915065A | Sep. 15, 2006 | Dec. 18, 2007 | 1/256 | Pass | 15-months |
| 1127065A | Nov. 27, 2006 | Feb. 27, 2008 | 1/256 | Pass | |
| 0523075A | May 23, 2007 | pending | | | |
| 0915065A | Sep. 15, 2006 | Mar. 18, 2008 | 1/256 | Pass | 18-months |
| 1127065A | Nov. 27, 2006 | pending | | | |
| 0523075A | May 23, 2007 | pending | | | |
| 0915065A | Sep. 15, 2006 | pending | | | 24-months |
| 1127065A | Nov. 27, 2006 | pending | | | |
| 0523075A | May 23, 2007 | pending | | | |

EXPERIMENTAL

Example I

LDFA Detection Of Influenza A Virus

Duplicate R-Mix® sv/cs cell culture monolayers were inoculated with as series of four (4) 10-fold serial dilutions (i.e., designated as samples: 4+, 3+, 2+, and 1+) of either influenza A virus (A/H3N2) or Herpes simplex virus (HSV-1) and compared to a negative control (NC). The infected cultures were cultivated on coverslips within shell vials to allow virus replication for approximately twenty-two (22) hours.

The culture medium was aspirated from the 4+, 1+, and NC shell vials for each virus set. Phosphate buffered saline (PBS; 200 μl) were then added to each shell vial; and the monolayer was scraped off of the coverslip and transferred to a labeled 1.5 ml Eppendorf centrifuge tube Acetone (100%; 800 μl) was added to each centrifuge tube to bring the final volume to 1 ml to create an 80% acetone/cell suspension solution This solution was incubated at room temperature for approximately 10 minutes to permeabilize the cells.

The permeabilized cells were then harvested and centrifuged in a Carl's microtube centrifuge for 6 min @ 4000 rpm. Each tube was then aspirated to remove all liquid. Fluorescently labeled Flu A MAb or fluoresently labeled HSV-1 MAb (200 ul) was added to the appropriate tubes. Each cell pellet was then re-suspended in the MAb solution and incubated at 35-37° C. for 1 hour.

Subsequent to the MAb incubation, the tubes were placed back in the micro-centrifuge for 6 min @ 4000 rpm. Each tube was then aspirated to remove the MAb solution and the cells were resuspended in PBS (20 μl). An aliquot (10 μl) of each cell suspension was placed onto respective slides and then viewed on a widepass band FITC filter (100× magnification).

Example II

Duet MAb Virus Screening In Clinical Aspirates

Nasal discharge specimens were collected from patients. An aliquot of each specimen was placed in an A/B tube; R/M tube; or a P/Ad tube (A—influenza A; B—influenza B; R—respiratory virus; M—metapneumovirus; P—parainfluenza virus; Ad—adenovirus).

1. Add 70 μl of cell suspension to each tube
2. Add 2 drops of corresponding MAb
3. Incubate at 35° C.-37° C. for 5 minutes
4. Wash with 1.5 ml of PBS
5. Centrifuge for 2 minutes at 2000×g
6. Aspirate supernatant with transfer pipette
7. Add 20 μl Resuspension Buffer to each tube
8. Load slide Example III MAb Cross Reactivity: Listing Of Materials The following is a listing of the materials, with lot numbers, used in the described the cross-reactivity studies presented herein in accordance with Examples IV and V.

| Material | Lot Numbers |
|---|---|
| R-Mix Cultures (A549 and Mv1Lu cells) | 960309 |
| MRC-5 Shell Vials | C510328A |
| H & V Mix Cultures (MRC-5 and CV-1 cells) | 980309 |
| RM-03T Refeed Medium | 011206A |

-continued

| Material | Lot Numbers |
|---|---|
| RM02 Refeed Medium | 110905A |
|  | 010306A |
| HSV-1 DFA control stain | 013105 |
| HSV-2 DFA control stain | 013105A |
| Influenza A DFA control stain | 061505A |
| Influenza B DFA control stain | 060205B |
| Adenovirus DFA control stain | 041205D |
| Parainfluenza 1 DFA control stain | 081205P1 |
| Parainfluenza 2 DFA control stain | 040505P2 |
| Parainfluenza 3 DFA control stain | 052705P3 |
| RSV DFA control stain | 052505R |
| CMV IFA control stain | 031804 |
| Chemicon VZV DFA control stain | 24100183CE |
| Adenovirus | |
| ATCC VR-1 Type 1 | 061704J |
| ATCC VR-3 Type 3 | 112701A |
| ATCC VR-5 Type 5 | 070505 |
| ATCC VR-1083 Type 6 | 111201A |
| ATCC VR-7 Type 7 | 112701C |
| ATCC VR-1087 Type 10 | 111201B |
| ATCC VR-14 Type 13 | 112701E |
| ATCC VR-15 Type 14 | 033104 |
| ATCC VR-19 Type 18 | 011702A |
| ATCC VR-1109 Type 31 | 011702B |
| ATCC VR-931 Type 40 | 012802 |
| ATCC VR-930 Type 41 | 012802A |
| Influenza A Virus | |
| ATCC VR-547 A2/Aichi/2/68 strain | 061704O |
| ATCC VR-98 A/MaI/302/54 strain | 061704D |
| ATCC VR-544 A/Hong Kong/8/68 strain | 040104 |
| ATCC VR-546 A1/Denver/1/57 strain | 061704P |
| ATCC VR-810 A/Port Chalmers/1/73 strain | 061704C |
| ATCC VR-822 A/Victoria/3/75 strain | 080204 |
| ATCC VR-897 A/New Jersey/8/76 strain | 110404 |
| ATCC VR-1520 A/WS/33 strain | 061704B |
| ATCC VR-1469 A/PR/8/34 strain | 061704Q |
| Influenza B Virus | |
| ATCC VR-790 B/Russia/69 strain | 041105 |
| ATCC VR-295 B/Taiwan/2/62 strain | 061704E |
| ATCC VR-103 B/GL/1739/54 strain | 061704F |
| ATCC VR-523 B/Mass/3/66 strain | 093004A |
| ATCC VR-296 B/Maryland/1/59 strain | 041105 |
| ATCC VR-823 B/Hong Kong/5/72 strain | 093004B |
| JH-001 Isolate, Cell Culture Adapted | 061704R |
| RSV | |
| ATCC VR-1401 RSV B Wash/18537/'62 strain | 042204W |
| ATCC VR-26 Long strain | 042204L |
| ATCC VR-955 9320 strain | 061704I |
| Parainfluenza 1 Virus | |
| ATCC VR-94 C-35 strain | 061704L |
| Parainfluenza 2 Virus | |
| ATCC VR-92 Greer strain | 061704M |
| Parainfluenza 3 Virus | |
| ATCC VR-243 C 243 strain | 061704N |
| Parainfluenza 4 Virus | |
| ATCC VR-1378 M-25 strain | 112701U |
| ATCC VR-1377 CH 19503 strain | 112701V |
| Metapneumovirus | |
| Subgroup A1 | 110905 |
| Subgroup A2 | 110805 |
| Subgroup B1 | 111105 |
| Subgroup B2 | 110405 |
| Coronavirus | |
| ATCC VR-740 229E strain | 121903 |
| ATCC VR-1558 OC43 strain | 041204B |

-continued

| Material | Lot Numbers |
|---|---|
| Rhinovirus 39 | |
| ATCC VR-340 209 Picornavirus strain | 112701EE |
| HSV-1 | |
| ATCC VR-733 F (1) strain | 052405 |
| ATCC VR-539 MacIntyre strain | 071005 |
| HSV-2 | |
| ATCC VR-540 MS strain | 112701Y |
| ATCC VR-734 G strain | 052605 |
| CMV | |
| ATCC VR-977 Towne strain | 011503 |
| ATCC VR-807 Davis strain | 062005 |
| ATCC VR-538 Ad-169 strain | 052705 |
| VZV | |
| ATCC VR-916 Webster strain | 040504 |
| ATCC VR-1367 Ellen strain | 050903 |
| Echovirus | |
| Bion Enterprises Echovirus Panel Antigen Control Slide with Echo 4, 6, 9, 11, 30, and 34. | QEC-0008 |
| Coxsackie Virus | |
| Bion Enterprises Coxsackie Group B Antigen Control Slide with Coxsackie B1, B2, B3, B4, B5, and B6. | QCB-0011 |
| Mumps Virus | |
| Bion Enterprises Mumps Antigen Control Slide | QMU-0308 |
| Rubeola (Measles) Virus | |
| Bion Enterprises Rubeola Antigen Control Slide | QME-0424 |
| Cell Lines Tested for Cross Reactivity | |
| RD (Human Rhabdomyosarcoma) | C760908 |
| Mv1Lu (Mink Lung) | C580915 |
| LLC-MK2 (Rhesus Monkey Kidney) | C860928S |
| MRHF (Human Foreskin Fibroblast) | C440912 |
| NCI-H292 (Human Pulmonary Muco-Epidermoid Carcinoma) | C590929 |
| BGMK (Buffalo Green Monkey Kidney) | C530914 |
| MDCK (Madin-Darby Canine Kidney) | C830921S |
| pRHMK (Primary Rhesus Monkey Kidney) | CA490922 |
| pRHMK II (pRHMK less than 3 years old) | A490909YS |
| MRC-5 (Human Embryonic Lung Fibroblast) | C510920 |
| HEp-2 (Human Epidermoid Carcinoma) | C570914 |
| pRK (Primary Rabbit Kidney) | 480909 |
| pCMK (Primary Cynomolgus Monkey Kidney) | A470907 |
| A549 (Human Lung Carcinoma) | C560921 |
| R-Mix (Mv1Lu and A549 mixed cells) | C960922 |
| WI-38 (Human Embryonic Lung Fibroblasts) | 850913 |
| Vero (African Green Monkey Kidney) | C840914S |
| Other Microorganisms/Growth Media | |
| ATCC 15531 *Mycoplasma pneumoniae* | 031404 |
| ATCC 23114 *Mycoplasma hominis* | 031404 |
| ATCC 23714 *Mycoplasma orale* | 031404 |
| ATCC 23064 *Mycoplasma salivarium* | 031404 |
| ATCC 27618 *Ureaplasma urealyticum* | 031404 |
| ATCC 23206 *Acholeplasma laidlawii* | 031404 |
| ATCC 10580 *Bordetella bronchiseptica* | 031404 |
| ATCC 10380 *Bordetella pertussis* | 031404 |
| ATCC 33152 *Legionella pneumophila* | 031404 |
| ATCC 8176 *Moraxella cartarrhalis* | 031404 |
| ATCC 19409 *Corynebacterium diphtheriae* | 031404 |
| ATCC 9006 *Haemophilis influenzae* Type A | 031404 |
| ATCC 33495 *Klebsiella pneumoniae* | 031404 |
| ATCC 9027 *Pseudomonas aeruginosa* | 031404 |
| ATCC 10813 *Streptococcus pneumoniae* | 031404 |
| ATCC 9898 *Streptococcus pyogenes* | 031404 |
| *Trichomonas vaginalis* slide | 25030319CE |
| *Chlamydia psittaci* slide | FP-12-050218 |
| *Chlamydia pneumoniae* slide | CP-0176 |
| *Chlamydia trachomatis* slide | 052705 |

| Material | | Lot Numbers |
|---|---|---|
| Gardnerella vaginalis | | 410721 |
| Salmonella minnesota (enteriditis) | | 3457511 |
| Neisseria gonorrhoeae | | 060805 |
| Salmonella typhimurium | | 363162 |
| Acinetobacter calcoaceticus | | 934332 |
| Candida glabrata | | 992206 |
| Escherichia coli | | 335472 |
| Proteus mirabilis | | 440498 |
| Streptococcus agalactiae | | 370784 |
| Staphylococcus aureus | | 081100 |
| BG Sulfa agar | Hardy Diagnostics | G87 |
| Blood agar | Hardy Diagnostics | 5257771 |
| RTF Casman Agar | Hardy Diagnostics | A68 |
| MacConkey agar | Hardy Diagnostics | G35 |
| Nickerson's Agar | Hardy Diagnostics | G17 |
| Trypticase Soy Agar | BD BBL | 292396 |

Example IV

Viral Cross Reactivity Protocols

A. Respiratory Viruses

1. Preparation of Frozen Stocks:

a. Influenza A and B

Amplify Influenza in MDCK T-75 cm$^2$ flasks from the original ATCC cultures as follows:

Thaw and, if necessary, add sterile water to each lyophilized vial of Influenza and vortex for 5 to 10 seconds.

Remove 0.250-mL and add to 10-mL of RM03T Refeed Medium (DHI catalog number 10-330500). Vortex for 5 to 10 seconds.

Aspirate medium from the flask. Rinse the flask using 10-mL RM03T and add the 10-mL of diluted virus from step 2.

Place into a humidified 35° to 37° C. incubator with 5% $CO_2$ for 2 hours. Rock the flask every 10 to 15 minutes.

Add 20-mL of RM03T to the flask and return it to the incubator.

Monitor daily for cytopathic effect (CPE). When monolayer reaches ~80% to 100% CPE, place flask in a −80° C. freezer for at least 24 hours.

Rapidly thaw flask in a 35° to 37° C. water bath.

Transfer virus-infected medium from the flask to 50-mL polypropylene conical centrifuge tubes and vortex.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

b. Respiratory Syncytial Virus (RSV), and Parainfluenza 1, 2, and 4

Amplify RSV in HEp-2 T-75 cm$^2$ flasks from the original ATCC cultures as follows:

Thaw and, if necessary, add sterile water to each lyophilized vial of RSV and vortex for 5 to 10 seconds.

Remove 0.250-mL and add to 10-mL of RM03T Refeed Medium (DHI catalog number 10-330500). Vortex for 5 to 10 seconds.

Aspirate medium from the flask. Rinse the flask using 10-mL RM03T and add the 10-mL of diluted virus from step 2.

Place into a humidified 35° to 37° C. incubator with 5% $CO_2$ for 2 hours. Rock the flask every 10 to 15 minutes.

Add 20-mL of RM03T to the flask and return it to the incubator.

Monitor daily for CPE. When monolayer reaches ~80% to 100% CPE, place flask in a −80° C. freezer for at least 24 hours.

Rapidly thaw flask in a 35° to 37° C. water bath.

Transfer virus-infected medium from the flask to 50-mL polypropylene conical centrifuge tubes and vortex.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

c. Adenovirus

Amplify Adenovirus in A549 T-75 cm$^2$ flasks from the original ATCC cultures as follows:

Thaw and, if necessary, add sterile water to each lyophilized vial of Adenovirus and vortex 5 to 10 seconds.

Remove 0.25-mL and add to 10-mL of RM03T Refeed Medium. Vortex 5 to 10 seconds.

Aspirate medium from flask and add the 10-mL of diluted virus from step 2.

Place in a humidified 35° to 37° C. incubator with 5% $CO_2$ for 2 hours. Rock every 10 to 15 minutes.

Add 20-mL of RM03T Refeed Medium to the flask and return it to the incubator.

Monitor daily for CPE. When monolayer reaches 80% to 100% CPE, place flask in a −80° C. freezer for at least 24 hours.

Rapidly thaw flask in a 35° to 37° C. water bath.

Transfer virus-infected medium from the flask to 50-mL polypropylene conical centrifuge tubes and vortex.

Centrifuge at 300×g for 10 minutes to pellet cell debris.

Remove supernatant, taking care not to disturb pellet, transfer to another centrifuge tube and vortex.

Dispense 1-mL of the virus suspension into 1-mL cryo-vials and freeze at −80° C. or lower.

2. Determination of Respiratory Virus Concentrations

After the respiratory virus stocks are frozen, they are quantified (titered) on R-Mix cell cultures. Each virus is titered using the following method:

Rapidly thaw 1 vial of appropriate virus in a 35° to 37° C. water bath or heating block.

Vortex vial and remove 0.5-mL and transfer to 4.5-mL of RM03T Refeed Medium for a 1:10 dilution.

Continue making 1:10 serial dilutions to yield 1:100, 1:1,000, 1:10,000, 1:100,000, and 1:1,000,000 dilutions.

Aspirate culture medium from R-Mix cultures and add 1-mL of each dilution to duplicate monolayers.

Centrifuge at 700×g for 60 minutes.

Place monolayer in a 35° to 37° C. incubator for 24 hours.

Aspirate medium and fix cells in 80% acetone for 5-10 minutes. Remove acetone and add Phosphate Buffered Saline (PBS) Wash Solution (DHI catalog number 01-001025) to prevent monolayers from drying out.

Stain with specific MAb reagents and examine for fluorescence.

Count fluorescent foci and note the dilution counted. Calculate the titer as follows: average count×the reciprocal of the dilution factor=virus/mL.

These stocks may be cultured and sub-cultured on a routine basis.

Example: 250 fluorescent foci counted at a 1:10,000 dilution in a 1 mL inoculum would yield (250 foci with a 1 mL inoculum×10,000=2.5e6 virus/mL). This is converted to 3. Cross-Reactivity Testing The R-Mix cell line containing both MvlLu and A549 cells is used for virus isolation staining of Influenza A, Influenza B, RSV, Parainfluenza Virus Types 1, 2, 3, 4a, 4b, and Adenovirus. Monolayers in 96-well micro-titer plates are used and processed according to the following procedure:

Rapidly thaw 1 vial of appropriate virus in a 35° to 37° C. water bath or heating block.

Vortex freezer vial then dilute each Respiratory virus strain in RM03T Refeed Medium at a 1,400 $TCID_{50}$ per 0.5-mL inoculum.

Aspirate culture medium from each 48-well plate and add 0.5 mL of inoculum.

Centrifuge at 700×g for 60 minutes.

Place plates in a 35° to 37° C. incubator for 24 hours.

Remove from incubator, aspirate medium and rinse with 1-mL of PBS.

Aspirate PBS then fix monolayers with 1-mL of 80% acetone for 5 minutes. Aspirate then add 0.5-mL of PBS.

Remove PBS and add 0.15-mL of the CMV test reagent to duplicate monolayers. Also add 0.15-mL of the Influenza A, Influenza B, Parainfluenza, RSV, and Adenovirus Positive Control Reagents (DHI catalog numbers 01-013102, 01-013202, 01-013302, 01-013402, 01-013502, 01-013602, and 01-013702, and Light Diagnostics Parainfluenza 4 reagent catalog number 5034) in duplicate monolayers.

Place cultures in a 35° to 37° C. incubator for 30 minutes.

Rinse 2 to 3 times with 1×PBS Solution. Remove each coverslip using a bent tip needle and place on to a drop of Mounting Fluid cell-side down.

Examine for fluorescence at 100-200× total magnification and note wells where fluorescent staining cells or background staining is visible. Only the specific positive control reagents should exhibit fluorescence; there should be no fluorescence from the test MAb Reagent.

B. Herpes Simplex Virus (HSV) 1 and 2 and Cytomegalovirus (CMV)

1. Preparation of Frozen Stocks:

Amplify HSV and CMV in MRC-5 T-75 $cm^2$ flasks from the original ATCC cultures as follows:

Thaw and, if necessary, add sterile water to each lyophilized vial of HSV or CMV and vortex 5 to 10 seconds.

Remove 0.250-mL and add to 10-mL of SR120 Refeed Medium (DHI catalog number 10-200100). Vortex 5 to 10 seconds.

Aspirate medium from the flask. Rinse the flask using 10-mL RM02 Refeed Medium and add the 10-mL of diluted virus from step 2.

Place into a humidified 35° to 37° C. incubator with 5% $CO_2$ for 2 hours. Rock the flask every 10 to 15 minutes.

Add 20 mL of SR120 Refeed Medium to the flask and return it to the incubator.

Monitor daily for CPE. When the monolayer reaches ~80% to 100% CPE, process the HSV and CMV as follows:

For HSV only:

Place HSV-infected flask in a −80° C. freezer for at least 24 hours.

Rapidly thaw flask in a 35° to 37° C. water bath.

For CMV only:

Scrape cells into medium in the flask.

Transfer to a syringe and pressure lyse through a 26-gauge syringe needle into a 50-mL centrifuge tube.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

2. Determination of HSV/CMV Concentrations

The stocks are titered by the following procedure:

One vial of each strain of HSV/CMV is thawed in a 35° to 37° C. water block.

Vortex each vial and remove and transfer 0.5-mL to 4.5-mL of ELVIS® Replacement Medium (DHI catalog number 10-220100) for HSV and RM-02 Refeed Medium (DHI catalog number 10-320100) for CMV for a 1:10 dilution.

Continue making 1:10 serial dilutions to yield: 1:100, 1:1,000, 1:10,000, 1:100,000, and 1:1,000,000 dilutions.

Aspirate the culture medium from the ELVIS®/MRC-5 cultures and add 1-mL of each dilution to duplicate monolayers.

Centrifuge at 700×g for 60 minutes.

Place cultures in a 35° to 37° C. incubator for 24 hours.

Aspirate medium and fix cells in 80% acetone for 5-10 minutes. Remove acetone and add PBS to prevent monolayers from drying out.

Stain HSV with the ELVIS Typing System and CMV with an antibody specific to the Immediate Early CMV Antigen and examine for fluorescence.

Count fluorescent foci for both CMV and HSV and note the dilution counted. Calculate the titer as follows: average count×the reciprocal of the dilution factor=virus/mL.

These stocks may be cultured and sub-cultured on a routine basis.

Example: 250 fluorescent foci counted at a 1:10,000 dilution in a 1 mL inoculum would yield (250 foci with a 1 mL inoculum×10,000=2.5e6 virus/mL). This is converted to $TCID_{50}$ by dividing the foci per mL by 0.7 as stated by the ATCC. atcc.org/common/technicalInfo/faqAnimalVirology.cfm 3. Cross-Reactivity Testing For the cross-reactivity studies, HSV and CMV strains are inoculated into H&V Mix (MRC-5+CV1 mix) shell vial cultures:

Each virus stock is rapidly thawed in a 35° to 37° C. water block.

Dilute each HSV and CMV virus stock to be tested at a 140 $TCID_{50}$ per 1-mL inoculum in RM02 Refeed Medium.

Aspirate culture medium from each H&V Mix shell vial and add 1-mL of inoculum.

Centrifuge at 700×g for 60 minutes.

Place monolayer in a 35° to 37° C. incubator for 24 hours.

Remove from incubator, aspirate inoculum and rinse with 1-mL of PBS.

Aspirate PBS then fix monolayers with 1-mL of acetone for 5 minutes. Aspirate then add 1-mL of PBS.

Remove PBS and add 0.2-mL of the CMV MAb test reagent to duplicate shell vials of both HSV and CMV infected monolayers. For the HSV infected monolayers, add 0.2 mL of the HSV-1 and HSV-2 Positive Control Reagents (DHI catalog numbers 03-09510 and 03-09520) to each in duplicate. For the CMV infected shell vials, add 0.2 mL of the CMV IE Ag Positive Control Reagent (DHI catalog number 03-07300) to duplicate shell vials.

Place cultures in a 35° to 37° C. incubator for 30 minutes.

For the shell vials staining with the CMV IE Ag Positive Control, rinse each vial 2 to 3 times then add 0.2-mL of CMV IE Ag Goat Anti-Mouse Reagent (DHI catalog number 03-07400) and incubate again for 30 more minutes.

Rinse 2 to 3 times with PBS. Remove each coverslip using a bent tip needle and place on to a drop of Mounting Fluid cell-side down.

Examine for fluorescence at 100-200× total magnification and note wells where fluorescent staining cells or background staining is visible. Only the specific positive control reagents should exhibit fluorescence; there should be no fluorescence from the CMV MAb test reagent on HSV-1 and HSV-2 infected monolayers. For the CMV infected monolayers, the CMV MAb test reagent and positive control should both show fluorescence.

C. Varicella-Zoster Virus (VZV)

1. Preparation of Frozen Stocks:

Amplify VZV in a CV-1 T-75 $cm^2$ flask from the original ATCC culture as follows:

Thaw VZV and vortex 5 to 10 seconds.

Remove 0.250-mL and add to 10-mL SR120 Refeed Medium (DHI catalog number 10-200100). Vortex 5 to 10 seconds.

Aspirate medium from the flask. Rinse the flask using 10-mL RM02 Refeed Medium and add the 10-mL of diluted virus from step 2.

Place into a humidified 35° to 37° C. incubator with 5% $CO_2$ for 2 hours. Rock the flask every 10 to 15 minutes.

Add 20-mL of SR120 Refeed Medium to the flask and return it to the incubator.

Monitor daily for CPE. When the monolayer reaches ~50% CPE, trypsinize cells and transfer to a CV-1 T-225 $cm^2$ flask and monitor daily for CPE. When the monolayer reaches 80% to 100% CPE, scrape cells and pressure lyse through a 26-gauge syringe needle into 50-mL centrifuge tubes.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

2. Determination of VZV Concentrations

The stocks are titered in the following manner on MRC-5 monolayers:

Rapidly thaw one vial of each VZV strain in a 35° to 37° C. water block.

Vortex each vial and transfer 0.5-mL into 4.5-mL of RM-02 for a 1:10 dilution.

Continue making 1:10 serial dilutions to yield: 1:100, 1:1,000, 1:10,000, 1:100,000, and 1:1,000,000 dilutions.

Aspirate culture medium from MRC-5 monolayers and add 1-mL of each dilution to duplicate monolayers.

Centrifuge at 700×g for 60 minutes.

Place monolayer in a 35° to 37° C. incubator for 72 hours.

Aspirate medium and fix cells in 80% acetone for 5-10 minutes. Remove acetone and add PBS to prevent monolayers from drying out.

Stain with a MAb specific for VZV and examine for fluorescence.

Count fluorescent foci and note the dilution counted. Calculate the titer as follows: average count×the reciprocal of the dilution factor=virus/mL.

These stocks may be used and sub-cultured on a routine basis.

Example: 250 fluorescent foci counted at a 1:10,000 dilution in a 1-mL inoculum would yield (250 foci with a 1-mL inoculum×10,000=2.5e6 virus/mL). This is converted to $TCID_{50}$ by dividing the foci per mL by 0.7 as stated by the ATCC. atcc.org/common/technicalInfo/faqAnimalVirology.cfm 3. Cross-Reactivity Testing:

For cross-reactivity studies, the VZV strains are inoculated into H&V Mix (MRC-5+CV-1 mix) shell vial cultures:

Each virus stock is rapidly thawed in a 35° to 37° C. water block.

Dilute each VZV strain in RM-02 Refeed Medium to yield a 140 $TCID_{50}$ per 1-mL inoculum.

Aspirate culture medium from each H&V Mix multiwell plate and add 0.2-mL of inoculum.

Centrifuge at 700×g for 60 minutes.

Place plates in a 35° to 37° C. incubator for 72 hours.

Remove from incubator, aspirate inoculum and rinse with 0.2-mL of PBS.

Aspirate PBS then fix monolayers with 0.2-mL of 80% acetone for 5 minutes. Aspirate then add 0.2-mL of PBS.

Aspirate PBS then add 0.05-mL of the subject reagent to duplicate shell vials. Add 0.2-mL of the VZV Positive Control Reagent (DHI Catalog number 01-025005) to duplicate wells.

Place cultures in a 35° to 37° C. incubator for 30 minutes.

Rinse 2 to 3 times with PBS. Add one drop of Mounting Fluid to each well.

Examine for fluorescence at 100-200× total magnification and note wells where fluorescent staining cells or background staining is visible. Only the specific positive control reagents should exhibit fluorescence; there should be no fluorescence from the test MAbs.

D. Rhinovirus 39

1. Preparation of Frozen Stocks:

Amplify Rhinovirus in a MRC-5 T-75 $cm^2$ flask from the original ATCC culture as follows:

Thaw Rhinovirus and vortex 5 to 10 seconds.

Remove 0.250-mL and add to 10-mL SR120 Refeed Medium (DHI catalog number 10-200100). Vortex 5 to 10 seconds.

Aspirate medium from the flask. Rinse the flask using 10-mL RM02 Refeed Medium and add the 10-mL of diluted virus from step b.

Place into a humidified 33°-35° C. incubator with 5% $CO_2$ for 2 hours. Rock the flask every 10 to 15 minutes.

Add 20-mL of SR120 Refeed Medium to the flask and return it to the incubator.

Monitor daily for CPE (cytopathic effect). When the monolayer reaches ~80-100% CPE, freeze flask in a −80° C. freezer for at least 24 hours.

Thaw flask in a 35°-37° C. water bath until just thawed.

Transfer virus-infected medium from the flask to 50-mL polypropylene conical centrifuge tubes and vortex.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

2. Determination of Rhinovirus Concentrations:

The stocks are titered in the following manner on MRC-5 monolayers:

Rapidly thaw one vial of Rhinovirus 39 in a 35°-37° C. water block.
Vortex each vial and transfer 0.5-mL into 4.5-mL of RM-02 for a 1:10 dilution.
Continue making 1:10 serial dilutions to yield: 1:100, 1:1,000, 1:10,000, 1:100,000, and 1:1,000,000 dilutions.
Aspirate culture medium from MRC-5 monolayers and add 1-mL of each dilution to duplicate monolayers.
Centrifuge at 700×g for 60 minutes.
Place monolayer in a 33°-35° C. incubator until CPE is observed. Note Day and dilution.

These stocks may be cultured and sub-cultured on a routine basis.

3. Cross Reactivity Testing:

For cross reactivity studies, the Rhinovirus is inoculated in to MRC-5 cell cultures:

Thaw virus stock rapidly in a 35°-37° C. water block.
Dilute the Rhinovirus in RM-02 Refeed Medium to yield a 1,400 $TCID_{50}$ per 1-mL inoculum.
Aspirate culture medium from each MRC-5 shell vial and add 1-mL of inoculum.
Centrifuge at 700×g for 60 minutes.
Place plates in a 33°-35° C. incubator for 24 hours.
Remove from incubator, aspirate inoculum and rinse with 1-mL of PBS.
Aspirate PBS then fix monolayers with 1-mL of 80% acetone for 5 minutes. Aspirate then add 1-mL of PBS.
Aspirate PBS then add 0.2-mL of the subject reagent to duplicate wells.
Place cultures in a 35°-37° C. incubator for 30 minutes
Rinse 2 to 3 times with PBS. Remove coverslip using a bent-tip needle and place, cell-side down, on to one drop of Mounting Fluid.
Examine for fluorescence at 100× total magnification. The viral plaques should not exhibit any fluorescent staining nor should there be an excess of background staining E. Coronaviruses 1. Preparation of Frozen Stocks:

Amplify Coronaviruses in MRC-5 T-75 $cm^2$ flasks from the original ATCC cultures as follows:

Thaw Coronaviruses and vortex 5 to 10 seconds.

Remove 0.250-mL and add to 10-mL SR120 Refeed Medium (DHI catalog number 10-200100). Vortex 5 to 10 seconds.

Aspirate medium from the flask. Rinse the flask using 10-mL RM02 Refeed Medium and add the 10-mL of diluted virus from step b.

Place into a humidified 33°-35° C. incubator with 5% $CO_2$ for 2 hours. Rock the flask every 10 to 15 minutes.

Add 20-mL of SR120 Refeed Medium to the flask and return it to the incubator.

Monitor daily for CPE (cytopathic effect). When the monolayer reaches ~80-100% CPE, freeze flask in a −80° C. freezer for at least 24 hours.

Thaw flask in a 35°-37° C. water bath until just thawed.

Transfer virus infected-medium from the flask to 50-mL polypropylene conical centrifuge tubes and vortex.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

2. Determination of Coronavirus Concentrations:

The Coronavirus stocks are titered in the following manner on MRC-5 monolayers:

Rapidly thaw one vial of each Coronavirus in a 35°-37° C. water block.

Vortex each vial and transfer 0.5-mL into 4.5-mL of RM-02 for a 1:10 dilution.

Continue making 1:10 serial dilutions to yield: 1:100, 1:1,000, 1:10,000, 1:100,000, and 1:1,000,000 dilutions.

Aspirate culture medium from MRC-5 monolayers and add 1-mL of each dilution to duplicate monolayers.

Centrifuge at 700×g for 60 minutes.

Place monolayers in a 33°-35° C. incubator for 16-24 hours.

Aspirate medium and fix cells in 80% acetone for 5-10 minutes. Remove acetone and add PBS to prevent monolayers from drying out.

Stain with a research use only monoclonal antibody for Coronaviruses and examine for fluorescence.

Count fluorescent foci and note the dilution counted. Calculate the titer as follows: average count×the reciprocal of the dilution factor=virus/mL.

These stocks may be cultured and subcultured on a routine basis.

Example: 250 fluorescent foci counted at a 1:10,000 dilution in a 1-mL inoculum would yield (250 foci with a 1-mL inoculum×10,000=2.5e6 virus/mL). This is converted to $TCID_{50}$ by dividing the foci per mL by 0.7 as stated by the ATCC. atcc.org/common/technicalInfo/faqAnimalVirology.cfm 3. Cross Reactivity Testing For cross reactivity studies, the Coronaviruses are inoculated in to MRC-5 cell cultures:

Thaw virus stock rapidly in a 35°-37° C. water block.

Dilute the Coronaviruses in RM-02 Refeed Medium to yield a 1,400 $TCID_{50}$ per 1-mL inoculum.

Aspirate culture medium from each MRC-5 shell vial and add 1-mL of inoculum.

Centrifuge at 700×g for 60 minutes.

Place plates in a 33°-35° C. incubator for 24 hours.

Remove from incubator, aspirate inoculum and rinse with 1-mL of PBS.

Aspirate PBS then fix monolayers with 1-mL of 80% acetone for 5 minutes. Aspirate then add 1-mL of PBS.

Aspirate PBS then add 0.2-mL of the subject reagent to duplicate wells. Add 0.2-mL of the research use only monoclonal antibody reagent in duplicate.

Place cultures in a 35°-37° C. incubator for 30 minutes

Rinse 2 to 3 times with PBS. Remove coverslip using a bent-tip needle and place, cell-side down, on to one drop of Mounting Fluid.

Examine for fluorescence at 100× total magnification. The subject reagent should not exhibit any fluorescent staining or excessive background staining. The positive controls should exhibit bright apple-green fluorescence.

F. Metapneumovirus

1. Preparation of Frozen Stocks

Amplify Metapneumovirus (MPV) subgroups in LLC-MK2 T-75 $cm^2$ flasks from stocks obtained from the University of Pavia, Italy:

Thaw all MPV subgroup vials and vortex 5 to 10 seconds.

Remove 0.250-mL and add to 10-mL SR120 Refeed Medium (DHI catalog number 10-200100). Vortex 5 to 10 seconds.

Aspirate medium from the flask. Rinse the flask using 10-mL RM02 Refeed Medium and add the 10-mL of diluted virus from step 2.

Place into a humidified 35°-37° C. incubator with 5% $CO_2$ for 2 hours. Rock the flask every 10 to 15 minutes.

Add 20-mL of SR120 Refeed Medium to the flask and return it to the incubator.

Monitor daily for CPE (cytopathic effect). When the monolayer reaches ~80-100% CPE, scrape cells from the flask into suspension.

Pressure-lyse each virus suspension separately through a 26-gauge needle.

Transfer lysed virus/cell suspension to 50-mL polypropylene conical centrifuge tubes and vortex.

Centrifuge at 300×g for 10 minutes to pellet cell debris.

Remove supernatant, taking care not to disturb pellet, transfer to another centrifuge tube and vortex.

Dispense 1-mL of the virus suspension into labeled 1-mL cryo-vials and freeze at −80° C. or lower.

2. Determination of Metapneumovirus Concentrations

The stocks are titered in the following manner on R-Mix monolayers:

Rapidly thaw one vial of each MPV subgroup in a 35°-37° C. water block.

Vortex each vial and transfer 0.5-mL into 4.5-mL of RM-03T for a 1:10 dilution.

Continue making 1:10 serial dilutions to yield: 1:100, 1:1,000, 1:10,000, 1:100,000, and 1:1,000,000 dilutions.

Aspirate culture medium from R-Mix monolayers and add 1-mL of each dilution to duplicate monolayers.

Centrifuge at 700×g for 60 minutes.

Place monolayers in a 35°-37° C. incubator for 24 hours.

Aspirate medium and fix cells in 80% acetone for 5-10 minutes. Remove acetone and add PBS Wash Solution (DHI catalog number 01-001025) to prevent monolayers from drying out.

Stain with MPV monoclonal antibody reagent and examine for fluorescence.

Count fluorescent foci and note the dilution counted. Calculate the titer as follows: average count×the reciprocal of the dilution factor=virus/mL.

These stocks may be cultured and subcultured on a routine basis.

Example: 250 fluorescent foci counted at a 1:10,000 dilution in a 1-mL inoculum would yield (250 foci with a 1-mL inoculum×10,000=2.5e6 virus/mL). This is converted to $TCID_{50}$ by dividing the foci per mL by 0.7 as stated by the ATCC. atcc.org/common/technicalInfo/faqAnimalVirology.cfm 3. Cross Reactivity Testing:

For cross reactivity studies, the MPV subgroups are inoculated in to R-Mix cell cultures:

Rapidly thaw 1 vial of appropriate virus in a 35°-37° C. water bath or heating block.

Vortex freezer vial then dilute each MPV subgroup in RM03T Refeed Medium at a 1,400 $TCID_{50}$ per 0.2-mL inoculum.

Aspirate culture medium from each 96-well plate and add 0.2-mL of inoculum.

Centrifuge at 700×g for 60 minutes.

Place monolayer in a 35°-37° C. incubator for 24 hours.

Remove from incubator, aspirate medium and rinse with 0.2-mL of PBS.

Aspirate PBS then fix monolayers with 0.2-mL of 80% acetone for 5 minutes. Aspirate then add 0.2-mL of PBS.

Remove PBS and add 0.05-mL of the subject reagent to duplicate monolayers. Also add 0.05-mL of the DHI MPV ASR as a positive control.

Place cultures in a 35°-37° C. incubator for 30 minutes.

Rinse 2 to 3 times with PBS Wash Solution. Add 1 drop of Mounting Fluid to each stained well.

Examine for fluorescence at 100× total magnification and note wells where fluorescent staining cells or background staining is visible. Fluorescence should not be observed in monolayers stained with the subject reagent. All 4 MPV subgroups should exhibit fluorescent staining cells using the MPV positive control reagent.

G. Echovirus, Coxsackie Virus, Measles, and Mumps

The following control slides were purchased from Bion Enterprises for the purpose of MAb screening and cross-reactivity studies. Each slide is individually foil-wrapped with wells containing microorganisms of tissue culture cells infected with a specific viral agent in addition to wells containing only the uninfected tissue culture cells. The infected tissue culture cells serve as a positive control and the uninfected tissue culture cells serve as a negative control. The specific microbial antigen is identified on the product label.

The Echovirus Panel (catalog number QEC-6506) contains six wells, each containing a mix of infected and uninfected cells. Each slide is comprised separately of Echovirus types 4, 6, 9, 11, 30, and 34.

The Coxsackie Virus Panel (catalog number QCB-2506) contains six wells, each containing a mix of infected and uninfected cells. Each slide is comprised separately of Coxsackie Virus types B1, B2, B3, B4, B5, and B6.

The Mumps Antigen Control Slides (catalog number QMU-8002) contain one well of Mumps infected cells and one well of uninfected cells.

The Measles Antigen Control Slides (catalog number QME-0424) contain one well of Measles infected cells and one well of uninfected cells.

The procedure for testing and staining of the antigen control slides is:

Stain each slide in duplicate with 0.03-mL per well of the subject test reagent.

Place the slides into a 35°-37° C. incubator for 30 minutes.

Remove from the incubator and gently rinse slides with PBS. Blot each slide dry while trying not to touch or disturb the cell spots.

Add one drop of Mounting Fluid to each well and place a coverglass on each slide.

Examine for fluorescence at 100× total magnification and note wells where fluorescent staining cells or background staining is visible.

H. Uninfected Cell Cultures

Uninfected cell cultures in shell vial format and glass, round-bottom tubes are tested for cross reactivity by the following procedures. Table 20.

TABLE 20

Cell Culture Formats Used in Cross Reactivity Studies

| Cell Lines | Medium/Format |
|---|---|
| RD (Human Rhabdomyosarcoma) | Shell Vial |
| Mv1Lu (Mink Lung) | Shell Vial |
| LLC-MK2 (Rhesus Monkey Kidney) | Shell Vial |
| MRHF (Human Foreskin Fibroblast) | Shell Vial |

TABLE 20-continued

Cell Culture Formats Used in Cross Reactivity Studies

| Cell Lines | Medium/Format |
|---|---|
| NCI-H292 (Human Pulmonary Muco-epidermoid carcinoma) | Shell Vial |
| BGMK (Buffalo Green Monkey Kidney) | Shell Vial |
| MDCK (Madin-Darby Canine Kidney) | Shell Vial |
| pRHMK (Primary Rhesus Monkey Kidney) | Glass Round Tube |
| pRHMK II (pRHMK less than 3 years old) | Glass Round Tube |
| MRC-5 (Human Embryonic Lung Fibroblast) | Shell Vial |
| HEp-2 (Human Epidermoid Carcinoma) | Shell Vial |
| pRK (Primary Rabbit Kidney) | Shell Vial |
| pCMK (Primary Cynomolgus Monkey Kidney) | Glass Round Tube |
| A549 (Human Lung Carcinoma) | Shell Vial |
| R-Mix (Mv1Lu and A549 mixed cells) | Shell Vial |
| WI-38 (Human Embryonic Lung Fibroblasts) | Glass Round Tube |
| Vero (African Green Monkey Kidney) | Shell Vial |

1. Shell Vial Procedure

Aspirate culture medium and rinse once using PBS.
Aspirate PBS and add 1-mL of 100% acetone fixative for 10 minutes.
Aspirate the fixative and add 1-mL of PBS.
Aspirate the PBS then add 0.2-mL of the subject reagent in duplicate then place into a 35°-37° C. incubator for 30 minutes.
Remove from incubator then rinse 2-3 times with PBS.
Using forceps and a bent-tip needle, remove each coverslip and place on to a drop of Mounting Fluid on a glass specimen slide.
Examine for fluorescence at 100× total magnification and note if fluorescent staining cells or background staining is visible.

2. Glass Round-Bottom Tube Procedure:

Use a 2-mL serological pipette and scrape the cell monolayer into the culture medium.
Transfer to 1.5-mL Eppendorf tube and centrifuge at 300×g for 10 minutes.
Aspirate supernatant and resuspend pellet in 1-mL of PBS.
Spot 8-well specimen slides with 0.01-mL. Allow to air dry for ~20 minutes.
Fix the specimen slides for 10 minutes in 100% acetone.
Add 0.03-mL of the subject reagent in duplicate wells of each cell line.
Place into a 35°-37° C. incubator for 30 minutes.
Remove from incubator then rinse 2-3 times with PBS.
Add one drop of Mounting Medium to each well and examine for fluorescence at 100× total magnification. Note if fluorescent staining cells or background staining is visible.

Example V

Bacterial Cross Reactivity Testing

A. *Mycoplasma* sp., *Ureaplasma* sp., and *Acholeplasma laidlawii*

1. Preparation of Frozen Stocks:

Thaw and reconstitute cultures from the ATCC.
Dilute cultures 1:10 and 1:100 with the broth supplied in MYCOTRIM® TC Triphasic Culture System (Irvine Scientific catalog number T500-000) for the detection of cultivatable *mycoplasma*.
Inoculate with 1-mL of the diluted bacteria by scoring the agar on the top of the flask and then releasing the remaining inoculum into the broth in the bottom of the flask. Note: An undiluted sample is not inoculated because it may contain preservatives that inhibit growth of the bacteria.
Place flasks at 35° to 37° C. Examine flasks daily for the appearance of "fried egg" colonies in the agar and turbidity in the medium.
When colonies are observed (about 6 to 7 days post-inoculation), scrape the bottom of the flask into the broth and transfer to a 1.5-mL Eppendorf centrifuge vial. Also add 0.2-mL of Dienes Stain to the agar side of the flask and stain for 30 minutes at 35° to 37° C. This stain will aid in viewing the colonies.
Centrifuge at 9,000×g in a microcentrifuge for 30 minutes. Aspirate off supernatant and resuspend pellet in 50% glycerol and freeze at −80° C.

2. Cross-Reactivity Testing:

Each bacterium is grown for cross-reactivity studies, prepared on slides, and concentrations concurrently verified using the following procedure:
Each bacteria stock vial is rapidly thawed in a 35° to 37° C. water block.
Vortex each vial and transfer into a 1.5-mL Eppendorf tube.
Centrifuge at 9,000×g for 30 minutes.
Aspirate the supernatant and resuspend the pellet in 1-mL of PBS.
Dilute cultures 1:100 and 1:1000 with the broth supplied in MYCOTRIM® TC Triphasic Culture System.
Inoculate with 1-mL of the diluted bacteria by scoring the agar on the top of the flask and then releasing the remaining inoculum into the broth in the bottom of the flask.
Place flasks at 35° to 37° C. Examine flasks daily for the appearance of "fried egg" colonies in the agar and turbidity in the medium.
When colonies are observed, scrape the bottom of the flask into the broth and transfer to a 1.5-mL Eppendorf centrifuge vial. Also add 0.2-mL of Dienes Stain to the agar side of the flask and stain for 30 minutes at 35° to 37° C. This stain will aid in viewing the colonies.
Centrifuge at 9,000×g for 30 minutes.
Aspirate the supernatant and resuspend the pellet in 1-mL of PBS.
Using a spectrophotometer, read 0.1-mL of each suspension in a 96-well microtiter plate at 600 nm. Include McFarland Turbidity Standards (Scientific Device Laboratory catalog number 2350) ranging from 0.5 to 4.0 on the same plate.
Based on the O.D. values, dilute each bacteria suspension in PBS to closely match the McFarland standard of 2.0 equaling approximately 6.0e6 CFU per mL.
Vortex suspensions then add 0.01-mL per well to 8-well glass slides at both McFarland adjusted concentrations.
Let each slide air dry then fix in acetone for 10 minutes.
Store unused slides in an air tight pouch with a desiccant pouch.
Each suspension adjusted to a McFarland Standard of 2.0 used to make slides is diluted 1:1000, 1:1,000,000, and 100,000,000 in broth supplied with the MYCOTRIM® TC Triphasic Culture System.
Inoculate with each 1-mL of the dilution series of bacteria by scoring the agar on the top of the flask and then releasing the remaining inoculum into the broth in the bottom of the flask.
Place flasks at 35° to 37° C. Examine flasks daily for the appearance of "fried egg" colonies in the agar and turbidity in the medium.

Note at which dilution series, colonies are still visible in the flask.

Each 8-well slide is stained with the subject reagent by the following procedure:

Stain duplicate wells of each bacteria slide with 30-4, per well of the CMV MAb test reagent.

Place the slides into a 35° to 37° C. incubator for 60 minutes.

Remove from incubator then gently rinse slides with PBS. Blot dry trying not to touch or disturb the cell spots.

Add a drop of Mounting Fluid to each well and place a coverglass upon each slide.

Examine for fluorescence at 200 and 400× total magnification and note wells where fluorescent staining cells or background staining is visible.

B. *Bordetella* sp., *Legionella* p., *Moraxella* sp., *Corynebacterium* sp., *Haemophilis* sp., *Klebsiella* sp., *Pseudomonas* sp., *Streptococcus* sp., *Neisseria gonorrhoeae, Staphylococcus aureus*

1. Preparation of Frozen Stocks:

Stocks of each were obtained from the ATCC and grown on the appropriate agar listed below:

Buffered Charcoal Yeast Extract: *Bordetella* sp. and *Legionella pneumophilia*

Blood Agar: *Moraxella cartarrhalis, Corynebacterium diphtheriae*, and *Streptococcus pneumoniae.*

Trypticase Soy Agar: *Neisseria gonorrhoeae, Klebsiella pneumoniae, Pseudomonas aeruginosa, Staphylococcus aureus*

Chocolate Agar: *Haemophilis influenzae* type A

These microorganisms are grown using the following procedure:

Dilute bacteria in Trypticase Soy Broth at 1:10 and 1:100 dilutions and absorb 1-mL of the suspension on the appropriate agar.

Place agar plates face down in a 35° to 37° C. humidified incubator. Check daily for colonies.

When colonies are observed, use a sterile 0.01-mL loop and transfer colonies to a 1.5-mL Eppendorf microcentrifuge tube containing 1-mL of PBS. Remove enough colonies to make the PBS turbid.

Centrifuge at 9,000×g for 30 minutes. Aspirate off supernatant and resuspend pellet in 50% glycerol and freeze at −80° C.

2. Cross-Reactivity Testing

Each bacterium is grown for cross-reactivity studies, prepared on slides, and concentrations concurrently verified using the following procedure:

Rapidly thaw each bacteria stock in a 35° to 37° C. water block.

Dilute bacteria in Trypticase Soy Broth at 1:10 and 1:100 dilutions and absorb 1-mL of the suspension on the appropriate agar.

Place agar plates face down in a 35° to 37° C. humidified incubator. Check daily for colonies.

When colonies are observed, use a sterile 0.01-mL loop and transfer individual colonies to an Eppendorf microcentrifuge tube containing 1-mL of PBS. Remove enough colonies to make the PBS turbid.

Use a sterile 0.01-mL loop and streak each specimen on a suitable agar.

Place agar plates face down in a 35° to 37° C. humidified incubator. Check daily for colonies.

When colonies are observed, use a sterile 0.01-mL loop and transfer colonies to a 1.5-mL Eppendorf centrifuge tube containing 1 mL of PBS. Remove enough colonies to make the PBS turbid.

Using a spectrophotometer, read 0.1-mL of each suspension in a 96-well microtiter plate at 600 nm. Include McFarland Turbidity Standards (Scientific Device Laboratory catalog number 2350) ranging from 0.5 to 4.0 on the same plate.

Based on the O.D. values, dilute each bacteria suspension in PBS to closely match the McFarland standard of 1.0 and 2.0 equaling approximately 3.0e6 and 6.0e6 CFU per mL.

Vortex suspensions then add 0.01-mL per well to 8-well glass slides at both McFarland adjusted concentrations.

Let each slide air dry then fix in acetone for 10 minutes.

Store unused slides in an air tight pouch with a desiccant pouch.

Each suspension at a McFarland Standard of 1.0 used to make slides is diluted 1:100, 1:10,000, 1:1,000,000, 1:10,000,000 and 100,000,000. 1-mL of each dilution from each bacterium is absorbed on to the appropriate agar plate for colony confirmation.

Place agar plates face down in a 35° to 37° C. humidified incubator. Check daily for colonies.

Count the colonies of the dilution plates with approximately 30-300 colonies. Multiply the count by the reciprocal of the dilution factor to calculate the CFU per mL.

Each 8-well slide is stained with the CMV MAb test reagent by the following procedure:

Stain duplicate wells of each bacteria slide with 30-µL per well of the CMV MAb test reagent.

Place the slides into a 35° to 37° C. incubator for 60 minutes.

Remove from incubator then gently rinse slides with PBS. Blot dry trying not to touch or disturb the cell spots.

Add a drop of Mounting Fluid to each well and place a coverglass upon each slide.

Examine for fluorescence at 200 and 400× total magnification and note wells where fluorescent staining cells or background staining is visible.

C. *Gardnerella vaginalis, Salmonella* sp., *Acinetobacter calcoaceticus, Candida Glabrata, Escherichia Coli, Proteus Mirabilis, Streptococcus Agalactiae*

1. Preparation of Frozen Stocks:

Lyophilized discs of each were obtained from Hardy Diagnostics and grown on the appropriate agar:

BG Sulfa agar: *Salmonella* sp.

Blood agar: *Streptococcus agalactiae*

RTF Casman agar: *Gardnerella vaginalis*

MacConkey agar: *Proteus mirabilis, Acinetobacter calcoaceticus, Escherichia coli*

Nickerson's agar: *Candida glabrata*

These microorganisms were reconstituted and grown in the following manner:

Remove the LYFO DISK vial from 4-8° C. storage and allow the unopened vial to equilibrate to room temperature.

Aseptically remove one gelatin pellet from the vial. Place the pellet in 0.5-mL of sterile Brain Heart Infusion Broth (Hardy Diagnostics catalog number R10).

Emulsify and crush pellet with a sterile swab or pipette until the pellet particles are uniform in size and the suspension is homogenous in appearance.

Saturate the swab immediately with the hydrated material and transfer the material to an appropriate, non-selective, nutrient or enriched agar medium. With pressure, rotate the swab, and inoculate a circular area (i.e., one inch or 25 mm in diameter) of the agar medium. Using the same swab or a sterile loop, repeatedly (about 10 to 20 times) streak through the inoculated area and then continue to streak the remainder of the agar surface.

When colonies are observed, use a sterile 0.01-mL loop and transfer colonies to a 1.5-mL Eppendorf microcentrifuge tube containing 1-mL of PBS. Remove enough colonies to make the PBS turbid.

Centrifuge at 9,000×g for 30 minutes. Aspirate off supernatant and resuspend pellet in 50% glycerol and freeze at −80° C.

2. Cross-Reactivity Testing

Each bacterium is grown for cross-reactivity studies, prepared on slides, and concentrations concurrently verified using the following procedure:

Rapidly thaw each bacteria stock in a 35° to 37° C. water block.

Dilute bacteria in Trypticase Soy Broth at 1:10 and 1:100 dilutions and absorb 1-mL of the suspension on the appropriate agar.

Place agar plates face down in a 35° to 37° C. humidified incubator. Check daily for colonies.

When colonies are observed, use a sterile 0.01-mL loop and transfer individual colonies to an Eppendorf microcentrifuge tube containing 1-mL of PBS. Remove enough colonies to make the PBS turbid.

Use a sterile 0.01-mL loop and streak each specimen on a suitable agar.

Place agar plates face down in a 35° to 37° C. humidified incubator. Check daily for colonies.

When colonies are observed, use a sterile 0.01-mL loop and transfer colonies to a 1.5-mL Eppendorf centrifuge tube containing 1-mL of PBS. Remove enough colonies to make the PBS turbid.

Using a spectrophotometer, read 0.1-mL of each suspension in a 96-well microtiter plate at 600 nm. Include McFarland Turbidity Standards (Scientific Device Laboratory catalog number 2350) ranging from 0.5 to 4.0 on the same plate.

Based on the O.D. values, dilute each bacteria suspension in PBS to closely match the McFarland standard of 1.0 and 2.0 equaling approximately 3.0e6 and 6.0e6 CFU per mL.

Vortex suspensions then add 0.01-mL per well to 8-well glass slides at both McFarland adjusted concentrations.

Let each slide air dry then fix in acetone for 10 minutes.

Store unused slides in an air tight pouch with a desiccant pouch.

Each suspension at a McFarland Standard of 1.0 used to make slides is diluted 1:100, 1:10,000, 1:100,000, 1:1,000,000, 1:10,000,000 and 100,000,000. 1-mL of each dilution from each bacterium is absorbed on to the appropriate agar plate for colony confirmation.

Place agar plates face down in a 35° to 37° C. humidified incubator. Check daily for colonies.

Count the colonies of the dilution plates with approximately 30-300 colonies. Multiply the count by the reciprocal of the dilution factor to calculate the CFU per mL.

Each 8-well slide is stained with the CMV MAb test reagent by the following:

Stain duplicate wells of each bacteria slide with 30-µL per well of the CMV MAb test reagent.

Place the slides into a 35° to 37° C. incubator for 60 minutes.

Remove from incubator then gently rinse slides with PBS. Blot dry trying not to touch or disturb the cell spots.

Add a drop of Mounting Fluid to each well and place a coverglass upon each slide.

Examine for fluorescence at 200 and 400× total magnification and note wells where fluorescent staining cells or background staining is visible.

D. *Trichomonas vaginalis, Chlamydia psittaci, Chlamydia trachomatis:*

These microorganisms are fixed antigen control slides. The *Trichomonas. vaginalis* (catalog number 5073-5) and *Chlamydia pneumoniae* Control Slides (catalog number CP-4212) were obtained from Chemicon/Light Diagnostics.

The *Chlamydia psittaci* (catalog number 210-88-12-FC) were purchased from VMRD, Inc.

The *Chlamydia trachomatis* (catalog number 01-00011) slides are manufactured by Diagnostic Hybrids as a commercial product.

Each slide is stained with the CMV MAb test reagent by the following procedure:

Stain duplicate slides of each bacteria with 30-µL per well of the CMV MAb test reagent.

Place the slides into a 35° to 37° C. incubator for 60 minutes.

Remove from incubator then gently rinse slides with PBS. Blot dry trying not to touch or disturb the cell spots.

Add a drop of Mounting Fluid to each well and place a coverglass upon each slide.

Examine for fluorescence at 200 and 400× total magnification and note wells where fluorescent staining cells or background staining is visible.

The invention claimed is:

1. A method for detection of an intracellular antigen comprising:
   incubating a suspension comprising a biological sample, at least two differentially fluorescently labeled antibodies and a staining reagent to generate a liquid cell suspension, wherein said biological sample is suspected of comprising at least one intracellular respiratory viral antigen and wherein said liquid cell suspension comprises unfixed cells, wherein during the incubating, the at least one intracellular viral antigen binds to one of the at least two differentially fluorescently labeled antibodies to form an intracellular antigen-antibody complex, wherein said respiratory viral antigen is selected from the group consisting of a respiratory syncytial viral antigen, an influenza A viral antigen, an influenza B viral antigen, an adenovirus viral antigen, a parainfluenza viral antigen and a metapneumovirus viral antigen;
   detecting the intracellular antigen-antibody complex within the liquid cell suspension by identifying the one of the at least two differentially fluorescently labeled antibodies.

2. The method of claim 1, wherein each of the at least two differentially fluorescently labeled antibodies comprises a R-phycoerythrin fluorescent label or a fluorescein isothiocyanate fluorescent label.

3. The method of claim 1, wherein each of the at least two differentially fluorescently labeled antibodies is a monoclonal antibody.

4. The method of claim 1, wherein the staining reagent is detectable by fluorescent microscopy.

5. The method of claim 1, wherein the staining reagent is selected from the group consisting of Evans blue, propidium iodide, acridine orange and combinations thereof.

6. The method of claim 1, wherein at least one of the antibodies comprises specific affinity for said respiratory syncytial viral antigen.

7. The method of claim 1, wherein at least one of the antibodies comprises a specific affinity for said influenza A viral antigen.

8. The method of claim 1, wherein at least one of the antibodies comprises a specific affinity for said influenza B viral antigen.

9. The method of claim 1, wherein at least one of the antibodies comprises a specific affinity for said adenovirus viral antigen.

10. The method of claim 1, wherein at least one of the labeled antibodies comprises a specific affinity for said parainfluenza viral antigen.

11. The method of claim 1, wherein at least one of the labeled antibodies comprises a specific affinity for said metapneumovirus viral antigen.

12. The method of claim 1, wherein said suspension further comprises a permeabilization agent.

13. The method of claim 12, wherein said permeabilizaton agent comprises a detergent.

14. The method of claim 13, wherein said detergent is sapogenin.

* * * * *